(12) United States Patent
Myers et al.

(10) Patent No.: US 6,479,510 B2
(45) Date of Patent: Nov. 12, 2002

(54) QUINUCLIDINE-SUBSTITUTED ARYL COMPOUNDS FOR TREATMENT OF DISEASE

(75) Inventors: Jason K. Myers, Kalamazoo, MI (US); Vincent E. Groppi, Jr., Kalamazoo, MI (US); David W. Piotrowski, Portage, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/932,598

(22) Filed: Aug. 17, 2001

(65) Prior Publication Data

US 2002/0049225 A1 Apr. 25, 2002

Related U.S. Application Data

(60) Provisional application No. 60/284,966, filed on Apr. 19, 2001, and provisional application No. 60/226,164, filed on Aug. 18, 2000.

(51) Int. Cl.$^7$ .................. A61K 31/439; C07D 453/02
(52) U.S. Cl. .................. 514/305; 546/133; 544/127; 514/233.2
(58) Field of Search ............... 514/305, 233.2; 546/133; 544/127

(56) References Cited

U.S. PATENT DOCUMENTS

| | | | |
|---|---|---|---|
| 3,702,324 A | 11/1972 | Skinner et al. | 260/293.53 |
| 4,093,734 A | 6/1978 | Kruger et al. | 424/274 |
| 4,593,034 A | 6/1986 | Munson, Jr. et al. | 514/305 |
| 4,605,652 A | 8/1986 | Welstead, Jr. | 514/214 |
| 4,657,911 A | 4/1987 | Imbert et al. | 514/272 |
| 4,717,563 A | 1/1988 | Alphin et al. | 424/10 |
| 4,721,720 A | 1/1988 | Wootton et al. | 514/304 |
| 4,798,829 A | 1/1989 | King et al. | 514/214 |
| 4,803,199 A | 2/1989 | Donatsch et al. | 514/214 |
| 4,820,715 A | 4/1989 | Monkovic et al. | 514/305 |
| 4,835,162 A | 5/1989 | Abood | 514/305 |
| 4,863,919 A | * 9/1989 | Smith | 514/214 |
| 4,870,181 A | 9/1989 | Lo | 546/133 |
| 4,877,780 A | 10/1989 | Vega-Noverola et al. | 514/161 |
| 4,877,794 A | 10/1989 | Naylor et al. | 514/305 |
| 4,908,370 A | 3/1990 | Naylor et al. | 514/305 |
| 4,921,982 A | 5/1990 | Cohen et al. | 549/462 |
| 5,017,580 A | 5/1991 | Naylor et al. | 514/299 |
| 5,025,022 A | 6/1991 | Naylor et al. | 514/305 |
| 5,039,680 A | 8/1991 | Impoerato et al. | 514/304 |
| 5,057,519 A | 10/1991 | Suberg | 514/282 |
| 5,070,095 A | 12/1991 | Jagdmann, Jr. et al. | 514/305 |
| 5,084,460 A | 1/1992 | Munson, Jr. et al. | 514/282 |
| 5,106,843 A | 4/1992 | Ward et al. | 514/213 |
| 5,175,173 A | 12/1992 | Sun | 514/305 |
| 5,183,822 A | 2/1993 | Wijngaarden et al. | 514/305 |
| 5,206,246 A | 4/1993 | Langlois et al. | 514/272 |
| 5,236,931 A | 8/1993 | Jagdmann et al. | 514/305 |
| 5,237,066 A | 8/1993 | Dorme et al. | 546/133 |
| 5,246,942 A | 9/1993 | Youssefyeh et al. | 514/305 |
| 5,273,972 A | 12/1993 | Jagdmann et al. | 514/210 |
| 5,290,938 A | 3/1994 | Johansen | 546/133 |
| 5,491,148 A | 2/1996 | Berger et al. | 514/305 |
| 5,561,149 A | 10/1996 | Azria et al. | 514/397 |
| 5,723,103 A | 3/1998 | de Paulis et al. | 424/1.85 |
| 5,741,819 A | 4/1998 | Illig et al. | 514/602 |
| 5,837,489 A | 11/1998 | Elliott et al. | 435/69.1 |
| 5,919,793 A | 7/1999 | Brown et al. | 514/305 |
| 5,977,144 A | 11/1999 | Meyer et al. | 514/334 |

FOREIGN PATENT DOCUMENTS

| | | | |
|---|---|---|---|
| DE | 3810552 A1 | 10/1989 | C07D/451/12 |
| EP | 327335 A1 | 2/1988 | A61K/31/435 |
| EP | 353371 A1 | 2/1990 | A61K/31/505 |
| EP | 512350 A2 | 11/1992 | C07D/453/02 |
| FR | 2625678 | 1/1988 | A61K/31/435 |
| WO | WO 90/14347 | 11/1990 | C07D/453/02 |
| WO | WO 92/11259 | 6/1992 | C07D/451/04 |
| WO | WO 92/15579 | 9/1992 | C07D/451/00 |
| WO | WO96/40100 | 12/1996 | A61K/31/165 |
| WO | WO97/30998 | 8/1997 | C07D/453/02 |
| WO | WO 00/73431 A2 | 12/2000 | C12N/15/00 |
| WO | WO01/29034 | 4/2001 | C07D/453/02 |
| WO | WO 01/36417 A1 | 5/2001 | C07D/451/04 |
| WO | WO01/60821 | 8/2001 | C07D/453/02 |

OTHER PUBLICATIONS

Bannon, A.W., *American Association for the Advancement of Science*. Broad–Spectrum, Non–Opiodid Analgesic Activity by Selective Modulation of Neuronal Nicotinic Acetylcholine Receptors. vol. 279, No. 5347, pp. 77–81, 1998.

Dineley, K.T., and James W. Patrick, *The Journal of Biological Chemistry*. Amino Acid Determinants of •7 Nicotinic Acetylcholine Receptor Surface Expression. vol. 275, No. 18, pp. 13974–13985, May 5, 2000.

(List continued on next page.)

Primary Examiner—Charanjit S. Aulakh
(74) Attorney, Agent, or Firm—Mary J. Hosley

(57) ABSTRACT

The invention provides compounds of Formula I:

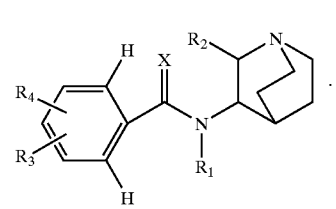

Formula I

These compounds may be in the form of pharmaceutical salts or compositions, and racemic mixtures or pure enantiomers thereof. The compounds of Formula I are useful in pharmaceuticals in which α7 is known to be involved.

118 Claims, No Drawings

OTHER PUBLICATIONS

Eisele, Jean–Luc. *Letters to Nature*. Chimaeric nicotinic–serotonergic receptor combines distinct ligand binding and channel specificities. vol. 366, pp. 479–483, Dec. 2, 1993.

Holladay, Mark W., et. al., *Journal of Medicinal Chemistry*. Neuronal Nicotinic Acetylcholine Receptors as Targets for Drug Discovery. Dec. 19, 1997.

Kem, William R. *Behavioral Brain Research*. "The brain α7 nicotinic receptor may be an important therapeutic target for the treatment of Alzheimer's disease: studies with DMXBA (GTS–21)." 113(2000) 169–181.

Kuntzweiler, Theresa A., et. al. *Drug Development Research*. "Rapid Assessment of Ligand Actions with Nicotinic Acetylcholine Receptors Using Calcium Dynamics and FLIPR." vol. 44, No. 1, pp. 14–20, May 1998.

Macor, JE. *Bioorganic & Medicinal Chemistry Letters*. "The 5-$HT_3$ Antagonist Tropisetron ( ICS 205–930) is a Potent and Selective α7 Nicotinic Receptor Partial Agonist." 11 (2001) 319–321.

\* cited by examiner

QUINUCLIDINE-SUBSTITUTED ARYL COMPOUNDS FOR TREATMENT OF DISEASE

CROSS REFERENCE TO RELATED APPLICATIONS

This application claims the benefit of U.S. provisional application Serial No. 60/226,164 filed on Aug. 18, 2000, under 35 USC 119(e)(i) and U.S. provisional application Serial No. 60/284,966 filed on Apr. 19, 2001, under 35 USC 119(e)(i), which are incorporated herein by reference in their entirety.

FIELD OF INVENTION

Nicotinic acetylcholine receptors (nAChRs) play a large role in central nervous system (CNS) activity. Particularly, they are known to be involved in cognition, learning, mood, emotion, and neuroprotection. There are several types of nicotinic acetylcholine receptors, and each one appears to have a different role in regulating CNS function. Nicotine affects all such receptors, and has a variety of activities. Unfortunately, not all of the activities are desirable. In fact, one of the least desirable properties of nicotine is its addictive nature and the low ratio between efficacy and safety. The present invention relates to molecules that have a greater effect upon the α7 nAChRs as compared to other closely related members of this large ligand-gated receptor family. Thus, the invention provides compounds that are active drug molecules with fewer side effects.

BACKGROUND OF THE INVENTION

U.S. Pat. No. 5,977,144 discloses compositions for benzylidene- and cinnamylidene-anabaseines and methods for using these compositions for treating conditions associated with defects or malfunctioning of nicotinic subtypes brain receptors. These compositions target the α7 receptor subtype with little or no activation of the α4β2 or other receptor subtypes.

U.S. Pat. No. 5,919,793 discloses heterocyclic derivatives useful in lowering cholesterol levels in blood plasma.

U.S. Pat. No. 5,837,489 discloses human neuronal nicotinic acetylcholine receptor and cells transformed with same DNA and mRNA encoding subunits.

U.S. Pat. No. 5,741,819 discloses arylsulfonylbenzene derivatives and their use as factor Xa inhibitors as being useful for the treatment of arterial and venous thrombotic occlusive disorders, inflammation, cancer, and neurodegenerative diseases.

U.S. Pat. No. 5,723,103 discloses substituted benzamides and radioligand analogs and methods of using the compounds for the identification of $5-HT_3$ receptors and the detection and treatment of abnormal conditions associated therewith.

U.S. Pat. No. 5,561,149 discloses the use of a mono or bicyclic carbocyclic, or heterocyclic carboxylic, acid ester or amide or an imidazolyl carbazol in the manufacture of a medicament suitable for the treatment of stress-related psychiatric disorders, for increasing vigilance, for the treatment of rhinitis or serotonin-induced disorders and/or coadministration with another active agent to increase the bioavailability thereof, or for nasal administration.

U.S. Pat. No. 5,491,148 discloses isoquinolinones and dihydroisoquinolinones which are $5-HT_3$ receptor antagonists.

U.S. Pat. No. 5,290,938 discloses optical active forms of the carboxylic acid amines of 3-aminoquinuclidine, generally N-(aminoquinuclidinyl-3)-alkylamides where alkyl is a linear or branched hydrocarbon chain of the general formula $C_nH_{(2n+1)}$, preferably $CH_3$ or $C_2H_5$, and the preparation thereof. These can be hydrolyzed to the optical active forms of 3-aminoquinuclidine.

U.S. Pat. No. 5,273,972 discloses novel 2-substituted-3-quinuclidinyl arylcarboxamides and arylthiocarboxamides and corresponding arylcarboxylates which have utility as therapeutic agents which exhibit gastric prokinetic, antiemetic, anxiolytic and 5-HT (serotonin) antagonist effects in warm blooded animals.

U.S. Pat. No. 5,246,942 discloses certain dibenzofurancarboxamides and their use as $5-HT_3$ antagonists having unique CNS, anti-emetic and gastric prokinetic activity void of any significant $D_2$ receptor binding properties.

U.S. Pat. No. 5,237,066 discloses enantiomers of absolute configuration S of amide derivatives of 3-aminoquinuclidine, the process for preparing them and their use as medicinal products having activity in respect of gastric movements and antiemetic activity.

U.S. Pat. No. 5,236,931 discloses novel 3-quinuclidinyl benzamides and benzoates which have utility as therapeutical agents which exhibit anxiolytic, antipsychotic, cognition improvement, antiemetic and gastric prokinetic effects in warm blooded animals.

U.S. Pat. No. 5,206,246 discloses anxiolytic-R-N-(1-azabicyclo[2.2.2]oct-3-yl) benzamides and thiobenzamides, their N-oxides and pharmaceutically acceptable salts thereof. A preferred compound is R-(+)-4-amino-N-(1-azabicyclo[2.2.2]oct-3-yl)-5-chloro-2-methoxybenzamide.

U.S. Pat. No. 5,183,822 discloses new heterocyclic compounds (3,4-annelated benzimidazole-2(1H)-ones) having an antagonistic activity on 5-hydroxytryptamine (5-HT) receptors.

U.S. Pat. No. 5,175,173 discloses carboxamides useful as antiemetic or antipsychotic agents.

U.S. Pat. No. 5,106,843 discloses heterocyclic compounds useful as $5-HT_3$ antagonists.

U.S. Pat. No. 5,084,460 discloses methods of therapeutic treatment with N-(3-quinuclidinyl)-2-hydroxybenzamides and thiobenzamides. The therapeutic agents are disclosed as exhibiting anxiolytic antipsychotic and cognitive improving effects in warm blooded animals.

U.S. Pat. No. 5,070,095 discloses novel 1-(azabicyclo[2.2.2]oct-3- or -4-yl)benzamides substituted on the benzene ring with the basic substituted aminomethyleneamino group which has been found to be useful in treating emesis, including emesis due to chemical and radiation anticancer therapy, anxiety, and impaired gastric emptying.

U.S. Pat. No. 5,057,519 discloses $5-HT_3$ antagonists as being useful in reducing opiate tolerance.

U.S. Pat. No. 5,039,680 disclose $5-HT_3$ antagonists in preventing or reducing dependency on dependency-inducing agents.

U.S. Pat. No. 5,025,022 discloses a method of treating or preventing schizophrenia and/or psychosis using S-N-(1-azabicyclo[2.2.2]oct-3-yl)benzamides and thiobenzamides, their N-oxides and pharmaceutically acceptable salts thereof. A preferred compound is S(−)-4-amino-N-(1-azabicyclo[2.2.2]oct-3-yl)-5-chloro-2-methoxybenzamide.

U.S. Pat. No. 5,017,580 discloses memory enhancing-R-N-(1-azabicyclo[2.2.2.]oct-3-yl)benzamides and thiobenzamides, their N-oxides and pharmaceutically acceptable salts thereof. A preferred compound is R-(+)-4-amino-N-(1-azabicyclo[2.2.2]oct-3-yl)-5-chloro-2-methoxybenzamide.

U.S. Pat. No. 4,921,982 discloses 5-halo-2,3-dihydro-2,2-dimethylbenzofuran-7-carboxylic acids which are useful as intermediates for 5-HT$_3$ antagonists.

U.S. Pat. No. 4,908,370 discloses anxiolytic-N-(1-azabicyclo[2.2.2]oct-3-yl) benzamides and thiobenzamides as having anxiolytic activity, in particular, activity against anxiety induced by the withdrawal from ingested substances such as narcotics.

U.S. Pat. No. 4,877,794 discloses 2-alkoxy-N-(1-azabicyclo[2.2.2]oct-3-yl) benzamide and thiobenzamide compositions and the use thereof to treat schizophrenia.

U.S. Pat. No. 4,877,780 discloses antiemetic N-substituted benzamides having pharmaceutical properties rendering them useful as antiemetic agents with reduced undesirable side effects.

U.S. Pat. No. 4,870,181 discloses a process for the preparation of 2-alkoxy-N-(1-azabicyclo[2.2.2]octan-3-yl) aminobenzamide.

U.S. Pat. No. 4,835,162 discloses agonists and antagonists to nicotine as smoking deterrents.

U.S. Pat. No. 4,820,715 discloses anti-emetic quinuclidinyl benzamides. The compounds are particularly useful in the treatment of chemotherapy-induced emesis in cancer patients. Some of the compounds are also useful in disorders relating to impaired gastric motility.

U.S. Pat. No. 4,803,199 discloses pharmaceutically useful heterocyclic acid esters and amides or alkylene bridged peperidines as serotonin M antagonists.

U.S. Pat. No. 4,798,829 discloses 1-azabicyclo[3.2.2] nonane derivatives having gastric motility enhancing activity and/or anti-emetic activity and/or 5-HT receptor antagonist activity.

U.S. Pat. No. 4,721,720 discloses a method of treating emesis, anxiety and/or irritable bowel syndrome.

U.S. Pat. No. 4,717,563 discloses 2-alkoxy-N-(1-azabicyclo[2.2.2]oct-3-yl) benzamides and thiobenzamides in a method for alleviating emesis caused by non-platinum anticancer drugs.

U.S. Pat. No. 4,657,911 discloses 3-amino quinuclidine derivatives and the application thereof as accelerators of gastro-intestinal motor function and as medicament potentiators.

U.S. Pat. No. 4,605,652 discloses a method of enhancing memory or correcting memory deficiency with arylamido (and arylthioamido)-azabicycloalkanes, and the pharmaceutically acceptable acid addition salts, hydrates and alcoholates thereof.

U.S. Pat. No. 4,593,034 discloses 2-alkoxy-N-(1-azabicyclo[2.2.2]oct-3-yl)benzamides and thiobenzamides having gastrokinetic and anti-emetic activity.

U.S. Pat. No. 4,093,734 discloses amino-benzoic acid amides useful as anxiolytics, anticonvulsives, antiemetics and antiulcerogenics.

U.S. Pat. No. 3,702,324 discloses 3,4,5-trimethoxybenzamides of substituted anilines and of alkylpiperidines which exert a specific effect on the central nervous system and a somewhat lesser effect on muscle function, and thus have utility as tranquilizers.

WO 01/36417 A1 discloses novel N-azabicyclo-amide derivatives and use in therapy, especially in the treatment of prophylaxis of psychotic disorders and intellectual impairment disorders.

WO 00/73431 A2 discloses two binding assays to directly measure the affinity and selectivity of compounds at the α7 nAChR and the 5-HT$_3$R. The combined use of these functional and binding assays may be used to identify compounds that are selective agonists of the α7 nAChR.

WO 92/15579 discloses multicyclic tertiary amine polyaromatic squalene synthase inhibitors and method of treatment for lowering serum cholesterol levels using the compounds.

WO 92/11259 discloses azabicyclic amides or esters of halogenated benzoic acids having 5-HT$_3$ receptor antagonist activity.

EP 512 350 A2 discloses 3-(indolyl-2-carboxamido) quinuclidines useful for treating diseases characterized by an excess or enhanced sensitivity to serotonin, e.g., psychosis, nausea, vomiting, dementia or other cognitive diseases, migraine, diabetes. The compound may be used to control anxiety, aggression, depression, and pain. The compounds are disclosed as serotonin 5-HT$_3$ antagonists.

FR 2 625 678 discloses N-(quinuclidin-3-yl)-benzamides and thiobenzamides useful as diet-control agents.

In *Bioorg. & Med. Chem. Lett.* 11 (2001) 319–321, the 5-HT$_3$ antagonist tropisetron (ICS 205–930) is discussed as a potent and selective (α7 nicotinic receptor partial agonist.

In *Behavioral Brain Res.*, 113 (2000) 169–181, it is discussed that the brain α7 nicotinic receptor may be an important therapeutic target for the treatment of Alzheimer's disease using DMXBA which is known as GTS-21.

Cell surface receptors are, in general, excellent and validated drug targets. nAChRs comprise a large family of ligand-gated ion channels that control neuronal activity and brain function. These receptors have a pentameric structure. In mammals, this gene family is composed of nine alpha and four beta subunits that co-assemble to form multiple subtypes of receptors that have a distinctive pharmacology. Acetylcholine is the endogenous regulator of all of the subtypes, while nicotine non-selectively activates all nAChRs.

The α7 nAChR is one receptor system that has proved to be a difficult target for testing. Native α7 nAChR is not routinely able to be stably expressed in most mammalian cell lines (Cooper and Millar, *Nature*, 366(6454), p.360–4, 1997). Another feature that makes functional assays of α7 nAChR challenging is that the receptor is rapidly (100 milliseconds) inactivated. This rapid inactivation greatly limits the functional assays that can be used to measure channel activity.

Recently, Eisele et al. has indicated that a chimeric receptor formed between the N-terminal ligand binding domain of the α7 nAChR (Eisele et al., *Nature*, 366(6454), p 479–83, 1993), and the pore forming C-terminal domain of the 5-HT$_3$ receptor expressed well in Xenopus oocytes while retaining nicotinic agonist sensitivity. Eisele et al. used the N-terminus of the avian (chick) form of the α7 nAChR receptor and the C-terminus of the mouse form of the 5-HT$_3$ gene. However, under physiological conditions the α7 nAChR is a calcium channel while the 5-HT$_3$R is a sodium and potassium channel. Indeed, Eisele et al. teaches that the chicken α7 nAChR/mouse 5-HT$_3$R behaves quite differently than the native α7 nAChR with the pore element not conducting calcium but actually being blocked by calcium ions. WO 00/73431 A2 reports on assay conditions under which the 5-HT$_3$R can be made to conduct calcium. This assay may be used to screen for agonist activity at this receptor.

SUMMARY OF THE INVENTION

The present invention discloses compounds of the Formula I:

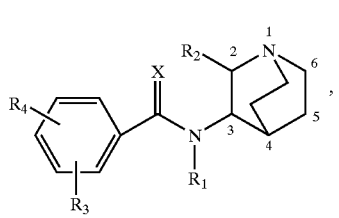

Formula I wherein

X is O or S;

R$_1$ is independently selected from the group consisting of —H, alkyl, cycloalkyl, halogenated alkyl, and aryl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from —R$_{12}$ and 0–3 substituents independently selected from —F, —Cl, —Br, or —I;

Substituted naphthyl is a naphthalene moiety either having 1–4 substituents independently selected from —F, —Cl, —Br, or —I, or having 1 substituent selected from —R$_{12}$ and 0–3 substituents independently selected from —F, —Cl, —Br, or —I, where the substitution can be independently on either only one ring or both rings of said naphthalene moiety;

R$_2$ is —H, alkyl, halogenated alkyl, substituted alkyl, cycloalkyl, benzyl, substituted benzyl, or aryl;

Substituted alkyl is an alkyl moiety from 1–6 carbon atoms and having 0–3 substituents independently selected from —F, —Cl, —Br, or —I and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, —NO$_2$, —R$_7$, —R$_9$, phenyl, or substituted phenyl;

Substituted benzyl is a benzyl either having 1–4 substituents independently selected from —F, —Cl, —Br, or —I, or having 1 substituent selected from —R$_{12}$ and 0–3 substituents independently selected from —F, —Cl, —Br, or —I, provided that all substitution is on the phenyl ring of the benzyl;

R$_3$ is selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —R$_7$, —R$_9$, —OR$_8$, —OR$_{17}$, —SR$_8$, —F, —Cl, —Br, —I, —NR$_8$R$_8$, —NR$_{16}$R$_{16}$, —C(O)R$_8$, —C(O)R$_{16}$, —CN, —C(O)NR$_8$R$_8$, —C(O)NR$_{15}$R$_{15}$, —NR$_8$C(O)R$_8$, —S(O)R$_8$, —OS(O)$_2$R$_8$, —NR$_8$S(O)$_2$R$_8$, —NO$_2$, and —N(H)C(O)N(H)R$_8$;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —R$_7$, —R$_9$, —OR$_{10}$, —SR$_{10}$, —NR$_{10}$R$_{10}$, —C(O)R$_{10}$, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —R$_7$, —R$_9$, —OR$_{10}$, —SR$_{10}$, —NR$_{10}$R$_{10}$, —C(O)R$_{10}$, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —CN, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —OR$_{10}$, —SR$_{10}$, —NR$_{10}$R$_{10}$, —C(O)R$_{10}$, —CN, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, —NO$_2$, phenyl, or substituted phenyl;

Heterocycloalkyl is a cyclic moiety having 4–7 atoms with 1–2 atoms within the ring being —S—, —N(R$_3$)—, or —O—;

Halogenated heterocycloalkyl is a cyclic moiety having from 4–7 atoms with 1–2 atoms within the ring being —S—, —N(R$_3$)—, or —O—, and having 1–4 substituents independently selected from —F, or —Cl;

Substituted heterocycloalkyl is a cyclic moiety having from 4–7 atoms with 1–2 atoms within the ring being —S—, —N(R$_3$)—, or —O— and having 0–3 substituents independently selected from —F, or —Cl, and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —NO$_2$, —S(O)$_2$NR$_{10}$R$_{10}$, —NR$_{10}$S(O)$_2$R$_{10}$, phenyl, or substituted phenyl;

R$_4$ is selected from the group consisting of —O—R$_5$, —S—R$_5$, —S(O)—R$_5$, —C(O)—R$_5$, and alkyl substituted on the ω carbon with R$_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is selected from aryl, $R_7$, or $R_9$;

$R_7$ is 5-membered heteroaromatic mono-cyclic moieties containing within the ring 1–3 heteroatoms independently selected from the group consisting of —O—, =N—, —N($R_{14}$)—, and —S—, and having 0–1 substituent selected from —$R_{12}$ and 0–3 substituents independently selected from —F, —Cl, —Br, or —I, or $R_7$ is a 9-membered fused-ring moiety having a 6-membered ring fused to a 5-membered ring and having the formula

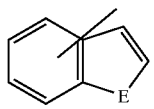

wherein E is O, S, or $NR_{14}$,

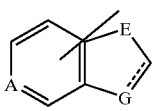

wherein E and G are independently selected from $CR_{18}$, O, S, or $NR_{14}$, and A is $CR_{18}$ or N, or

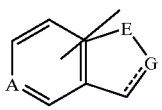

wherein E and G are independently selected from $CR_{18}$, O, S, or $NR_{14}$, and A is $CR_{18}$ or N, each 9-membered fused-ring moiety having 0–1 substituent selected from —$R_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each $R_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from —$R_{12}$ and 0–3 substituent(s) independently selected from —F, —Cl, —Br, or —I, or 10-membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from —$R_{12}$ and 0–3 substituent(s) independently selected from —F, —Cl, —Br, or —I and having a bond directly or indirectly attached to the core molecule where valency allows;

Each $R_{10}$ is independently selected from —H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently selected from —H, alkyl, cycloalkyl, heterocycloalkyl, halogenated alkyl, halogenated cycloalkyl, or halogenated heterocycloalkyl;

$R_{12}$ is selected from —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$;

$R_{13}$ is selected from —$OR_{11}$, —$SR_{11}$, —$NR_{11}R_{11}$, —$C(O)R_{11}$, —$C(O)NR_{11}R_{11}$, —CN, —$CF_3$, —$NR_{11}C(O)R_{11}$, —$S(O)_2NR_{11}R_{11}$, —$NR_{11}S(O)_2R_{11}$, or —$NO_2$;

$R_{14}$ is selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, or substituted phenyl;

Each $R_{15}$ is independently selected from alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{16}$ is independently selected from cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_{17}$ is selected from cycloalkyl, halogenated cycloalkyl, substituted cycloalkyl, heterocycloalkyl, halogenated heterocycloalkyl, or substituted heterocycloalkyl;

Each $R_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from —F, —Cl, —Br, or —I;

and pharmaceutically acceptable salts thereof. Compounds of Formula I are useful to treat any one of or combination of schizophrenia, or psychosis.

DETAILED DESCRIPTION OF THE INVENTION

Surprisingly, we have found that compounds of Formula I:

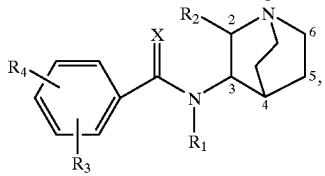

Formula I wherein

X is O or S;

$R_1$ is independently selected from the group consisting of —H, alkyl, cycloalkyl, halogenated alkyl, and aryl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from —$R_{12}$ and 0–3 substituents independently selected from —F, —Cl, —Br, or —I;

Substituted naphthyl is a naphthalene moiety either having 1–4 substituents independently selected from —F, —Cl, —Br, or —I, or having 1 substituent selected from —$R_{12}$ and 0–3 substituents independently selected from —F, —Cl, —Br, or —I, where the substitution can be independently on either only one ring or both rings of said naphthalene moiety;

$R_2$ is —H, alkyl, halogenated alkyl, substituted alkyl, cycloalkyl, benzyl, substituted benzyl, or aryl;

Substituted alkyl is an alkyl moiety from 1–6 carbon atoms and having 0–3 substituents independently selected from —F, —Cl, —Br, or —I and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, —$NO_2$, —$R_7$, —$R_9$, phenyl, or substituted phenyl;

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl;

$R_3$ is selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —$R_7$, —$R_9$, —$OR_8$, —$OR_{17}$, —$SR_8$, —F, —Cl, —Br, —I, —$NR_8R_8$, —$NR_{16}R_{16}$, —$C(O)R_8$, —$C(O)R_{16}$, —CN, —$C(O)NR_8R_8$, —$C(O)NR_{15}R_{15}$, —$NR_8C(O)R_8$, —$S(O)R_8$, —$OS(O)_2R_8$, —$NR_8S(O)_2R_8$, —$NO_2$, and —$N(H)C(O)N(H)R_8$;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n-1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —$NR_{10}C(O)R_{10}$, —$S(O)_2NR_{10}R_{10}$, —$NR_{10}S(O)_2R_{10}$, —CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n-3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —$NR_{10}C(O)R_{10}$, —$S(O)_2NR_{10}R_{10}$, —$NR_{10}S(O)_2R_{10}$, —CN, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_{10}$, —$NO_2$, phenyl, or substituted phenyl;

Heterocycloalkyl is a cyclic moiety having 4–7 atoms with 1–2 atoms within the ring being —S—, —$N(R_3)$—, or —O—;

Halogenated heterocycloalkyl is a cyclic moiety having from 4–7 atoms with 1–2 atoms within the ring being —S—, —$N(R_3)$—, or —O—, and having 1–4 substituents independently selected from —F, or —Cl;

Substituted heterocycloalkyl is a cyclic moiety having from 4–7 atoms with 1–2 atoms within the ring being —S—, —$N(R_3)$—, or —O— and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10R10}$, —$NR_{10}S(O)_2R_{10}$, phenyl, or substituted phenyl;

$R_4$ is selected from the group consisting of —O—$R_5$, —S—$R_5$, —S(O)—$R_5$, —C(O)—$R_5$, and alkyl substituted on the ω carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is selected from aryl, $R_7$, or $R_9$;

$R_7$ is 5-membered heteroaromatic mono-cyclic moieties containing within the ring 1–3 heteroatoms independently selected from the group consisting of —O—, =N—, —N($R_{14}$)—, and —S—, and having 0–1 substituent selected from —$R_{12}$ and 0–3 substituents independently selected from —F, —Cl, —Br, or —I, or $R_7$ is a 9-membered fused-ring moiety having a 6-membered ring fused to a 5-membered ring and having the formula

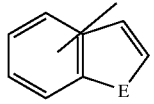

wherein E is O, S, or $NR_{14}$,

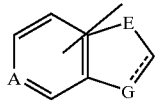

wherein E and G are independently selected from $CR_{18}$, O, S, or $NR_{14}$, and A is $CR_{18}$ or N, or

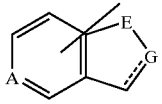

wherein E and G are independently selected from $CR_{18}$, O, S, or $NR_{14}$, and A is $CR_{18}$ or N, each 9-membered fused-ring moiety having 0–1 substituent selected from —$R_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each $R_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from —$R_{22}$ and 0–3 substituent(s) independently selected from —F, —Cl, —Br, or —I, or 10membered heteroaromatic bi-cyclic moieties containing within one or both rings 1–3 heteroatoms selected from =N—, including, but not limited to, quinolinyl or isoquinolinyl, each 10-membered fused-ring moiety having 0–1 substituent selected from —$R_{12}$ and 0–3 substituent(s) independently selected from —F, —Cl, —Br, or —I and having a bond directly or indirectly attached to the core molecule where valency allows;

Each $R_{10}$ is independently selected from —H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_{13}$, halogenated alkyl, halogenated cycloalkyl, halogenated heterocycloalkyl, phenyl, or substituted phenyl;

Each $R_{11}$ is independently selected from —H, alkyl, cycloalkyl, heterocycloalkyl, halogenated alkyl, halogenated cycloalkyl, or halogenated heterocycloalkyl;

$R_{12}$ is selected from —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$;

$R_{13}$ is selected from —$OR_{11}$, —$SR_{11}$, —$NR_{11}R_{11}$, —$C(O)R_{11}$, —$C(O)NR_{11}R_{11}$, —CN, —$CF_3$, —$NR_{11}C(O)R_{11}$, —$S(O)_2NR_{11}R_{11}$, —$NR_{11}S(O)_2R_{11}$, or —$NO_2$;

$R_{14}$ is selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, or substituted phenyl;

Each $R_{15}$ is independently selected from alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{16}$ is independently selected from cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_{17}$ is selected from cycloalkyl, halogenated cycloalkyl, substituted cycloalkyl, heterocycloalkyl, halogenated heterocycloalkyl, or substituted heterocycloalkyl;

Each $R_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring moiety has 0–3 substituent(s) selected from —F, —Cl, —Br, or —I;

and pharmaceutically acceptable salts thereof are useful to treat any one of or combination of schizophrenia, or psychosis.

Abbreviations which are well known to one of ordinary skill in the art may be used (e.g., "Ph" for phenyl, "Me" for methyl, "Et" for ethyl, "h" for hour or hours, "rt" for room temperature, and min for minute or minutes).

All temperatures are in degrees Centigrade.

Room temperature is within the range of 15–25 degrees Celsius.

Eq refers to equivalents.

AChR refers to acetylcholine receptor.

nAChR refers to nicotinic acetylcholine receptor.

5HT$_3$R refers to the serotonin-type 3 receptor.

α-btx refers to α-bungarotoxin.

FLIPR refers to a device marketed by Molecular Devices, Inc. designed to precisely measure cellular fluorescence in a high throughput whole-cell assay. (Schroeder et. al., *J. Biomolecular Screening,* 1(2), p 75–80, 1996).

TLC refers to thin-layer chromatography.

HPLC refers to high pressure liquid chromatography.

MeOH refers to methanol.

EtOH refers to ethanol.

IPA refers to isopropyl alcohol.

THF refers to tetrahydrofuran.

DMSO refers to dimethylsulfoxide.

DMF refers to dimethylformamide.

EtOAc refers to ethyl acetate.

TMS refers to tetramethylsilane.

TEA refers to triethylamine.

DIEA refers to diisopropylethylamine.

MLA refers to methyllycaconitine.

Ether refers to diethyl ether.

MgSO$_4$ refers magnesium sulfate.

NaHCO$_3$ refers to sodium bicarbonate.

KHCO$_3$ refers to potassium bicarbonate.

CH$_3$CN refers to acetonitrile.

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-6}$ alkyl refers to alkyl of one to six carbon atoms.

Halogen is F, Cl, Br, or I.

Alkyl denotes both straight- and branched-chained hydrocarbyl radicals having from 1–6 carbon atoms. For example, $C_{1-6}$ alkyl includes methyl, ethyl, propyl, isopropyl, butyl, iso-butyl, sec-butyl, pentyl, 3-pentyl, hexyl, and their isomeric forms thereof.

Halogenated alkyl is an alkyl moiety having from 1–6 carbon atoms and having 1 to (2n+1) halogen atom(s) where n is the maximum number of carbon atoms in the moiety.

Substituted alkyl is an alkyl moiety having from 1–6 carbon atoms and having 0–3 substituents independently selected from —F, —Cl, —Br, or —I, and further having 1 substituent selected from —R$_7$, —R$_9$, —OR$_{10}$, —SR$_{10}$, —NR$_{10}$R$_{10}$, —C(O)R$_{10}$, —NO$_2$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, phenyl, or substituted phenyl.

Alkenyl is straight- and branched-chained hydrocarbyl radicals having from 2–6 carbon atoms and having at least one carbon-carbon double bond.

Halogenated alkenyl is an unsaturated alkenyl moiety having from 2–6 carbon atoms and having 1 to (2n−1) halogen atom(s) where n is the maximum number of carbon atoms in the moiety.

Substituted alkenyl is an unsaturated alkenyl moiety having from 2–6 carbon atoms and having 0–3 substituents independently selected from —F, or —Cl, and further having 1 substituent selected from —R$_7$, —R$_9$, —OR$_{10}$, —SR$_{10}$, —NR$_{10}$R$_{10}$, —C(O)R$_{10}$, —CN, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, phenyl, or substituted phenyl.

Alkynyl is straight- and branched-chained hydrocarbyl radicals having from 2–6 carbon atoms and having at least one carbon-carbon triple bond.

Halogenated alkynyl is an unsaturated alkynyl moiety having from 3–6 carbon atoms and having 1 to (2n−3) halogen atom(s) where n is the maximum number of carbon atoms in the moiety.

Substituted alkynyl is an unsaturated alkynyl moiety having from 3–6 carbon atoms and having 0–3 substituents independently selected from —F, or —Cl, and further having 1 substituent selected from —R$_7$, —R$_9$, —OR$_{10}$, —SR$_{10}$, —NR$_{10}$R$_{10}$, —C(O)R$_{10}$, —CN, —C(O)NR$_{10}$R$_{10}$, —NR$_{10}$C(O)R$_{10}$, —S(O)$_2$NR$_{10}$R$_{10}$, —NR$_{10}$S(O)$_2$R$_{10}$, phenyl, or substituted phenyl.

Cycloalkyl is a cyclic alkyl moiety having from 3–6 carbon atoms.

Halogenated cycloalkyl is a cyclic moiety having from 3–6 carbon atoms and having 1–4 substituents independently selected from —F, or —Cl.

Substituted cycloalkyl is a cyclic moiety having from 3–6 carbon atoms and having 0–3 substituents independently selected from —F, or —Cl, and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —S(O)$_2$NR$_{10}$R$_{10}$, —NR$_{10}$S(O)$_2$R$_{10}$, —NO$_2$, phenyl, or substituted phenyl.

Heterocycloalkyl is a cyclic moiety having 4–7 atoms with 1–2 atoms within the ring being —S—, —N(R$_3$)— or —O—.

Halogenated heterocycloalkyl is a cyclic moiety having from 4–7 atoms with 1–2 atoms within the ring being —S—, —N(R$_3$)—, or —O—, and having 1–4 substituents independently selected from —F, or —Cl.

Substituted heterocycloalkyl is a cyclic moiety having from 4–7 atoms with 1–2 atoms within the ring being —S—, —N(R$_3$)— or —O— and having 0–3 substituents independently selected from —F, or —Cl, and further having 1 substituent selected from —OR$_{10}$, —SR$_{10}$, —NR$_{10}$R$_{10}$, —C(O)R$_{10}$, —C(O)NR$_{10}$R$_{10}$, —CN, —NR$_{10}$C(O)R$_{10}$, —NO$_2$, —S(O)$_2$NR$_{10}$R$_{10}$, —NR$_{10}$S(O)$_2$R$_{10}$, phenyl, or substituted phenyl.

Substituted benzyl is a benzyl either having 1–4 substituents independently selected from —F, —Cl, —Br, or —I, or having 1 substituent selected from —R$_{12}$ and 0–3 substituents independently selected from —F, —Cl, —Br, or —I, provided that all substitution is on the phenyl ring of the benzyl.

Aryl is phenyl, substituted phenyl, naphthyl, or substituted naphthyl.

Substituted phenyl is a phenyl either having 1–4 substituents independently selected from —F, —Cl, —Br, or —I, or having 1 substituent selected from —R$_{12}$ and 0–3 substituents independently selected from —F, —Cl, —Br, or —I.

Substituted naphthyl is a naphthalene moiety either having 1–4 substituents independently selected from —F, —Cl, —Br, or —I, or having 1 substituent selected from —R$_{12}$ and 0–3 substituents independently selected from —F, —Cl, —Br, or —I, where the substitution can be independently on either only one ring or both rings of said naphthalene moiety.

The ω carbon is determined by counting the longest carbon chain of the alkyl-type moiety with the C-1 carbon being the carbon attached to the phenyl ring of the core molecule and the ω carbon being the carbon furthest, e.g., separated by the greatest number of carbon atoms in the chain, from said C-1 carbon.

The core molecule is the quinuclidinyl-(carboxamide-type moiety)-phenyl:

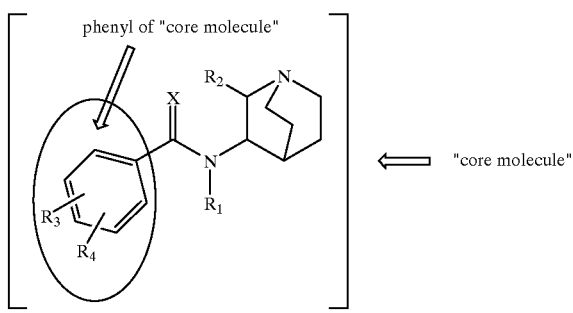

Therefore, when determining the ω carbon, the C-1 carbon will be the carbon attached to the phenyl ring of the core molecule and the ω carbon will be the carbon furthest from said C-1 carbon.

Mammal denotes human and other mammals.

Brine refers to an aqueous saturated sodium chloride solution.

IR refers to infrared spectroscopy.

Lv refers to leaving groups within a molecule, including Cl, OH, or mixed anhydride.

NMR refers to nuclear (proton) magnetic resonance spectroscopy, chemical shifts are reported in ppm (δ) downfield from TMS.

MS refers to mass spectrometry expressed as m/e or mass/charge unit. HRMS refers to high resolution mass spectrometry expressed as m/e or mass/charge unit. $M+H^+$ refers to the positive ion of a parent plus a hydrogen atom. $M-H^-$ refers to the negative ion of a parent minus a hydrogen atom. $M+Na^+$ refers to the positive ion of a parent plus a sodium atom. $M+K^+$ refers to the positive ion of a parent plus a potassium atom. EI refers to electron impact. ESI refers to electrospray ionization. CI refers to chemical ionization. FAB refers to fast atom bombardment.

Compounds of the present invention may be in the form of pharmaceutically acceptable salts. The term "pharmaceutically acceptable salts" refers to salts prepared from pharmaceutically acceptable non-toxic bases including inorganic bases and organic bases, and salts prepared from inorganic acids, and organic acids. Salts derived from inorganic bases include aluminum, ammonium, calcium, ferric, ferrous, lithium, magnesium, potassium, sodium, zinc, and the like. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N, N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, and the like. Salts derived from inorganic acids include salts of hydrochloric acid, hydrobromic acid, hydroiodic acid, sulfuric acid, phosphoric acid, phosphorous acid and the like. Salts derived from pharmaceutically acceptable organic non-toxic acids include salts of $C_{1-6}$ alkyl carboxylic acids, di-carboxylic acids, and tri-carboxylic acids such as acetic acid, propionic acid, fumaric acid, succinic acid, tartaric acid, maleic acid, adipic acid, and citric acid, and aryl and alkyl sulfonic acids such as toluene sulfonic acids and the like.

By the term "effective amount" of a compound as provided herein is meant a nontoxic but sufficient amount of the compound(s) to provide the desired effect. As pointed out below, the exact amount required will vary from subject to subject, depending on the species, age, and general condition of the subject, the severity of the disease that is being treated, the particular compound(s) used, the mode of administration, and the like. Thus, it is not possible to specify an exact "effective amount." However, an appropriate effective amount may be determined by one of ordinary skill in the art using only routine experimentation.

The compounds of Formula I have optically active center(s) on the quinuclidine ring. Although it is desirable that the stereochemical purity be as high as possible, absolute purity is not required. This invention involves racemic mixtures and compositions of varying degrees of strechemical purities. It is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

The preferred compounds of the present invention have the R configuration at the C3 position of the quinuclidine ring. It is also preferred for the compounds of the present invention that X is O. It is also preferred that $R_4$ is attached at the C4 position of the phenyl ring of the core molecule. Another group of compounds of Formula I includes compounds wherein X is O and $R_1$ is H. Another group of compounds of Formula I includes compounds wherein X is O and $R_2$ is H. Another group of compounds of Formula I includes compounds wherein X is O and $R_2$ is alkyl, halogenated alkyl, substituted alkyl, cycloalkyl, benzyl, substituted benzyl, or aryl.

The amount of therapeutically effective compound(s) that is administered and the dosage regimen for treating a disease condition with the compounds and/or compositions of this invention depends on a variety of factors, including the age, weight, sex and medical condition of the subject, the severity of the disease, the route and frequency of administration, and the particular compound(s) employed, and thus may vary widely. The compositions contain well know carriers and excipients in addition to a therapeutically effective amount of compounds of Formula I. The pharmaceutical compositions may contain active ingredient in the range of about 0.001–100 mg/kg/day for an adult, preferably in the range of about 0. 1–50 mg/kg/day for an adult. A total daily dose of about 1–1000 mg of active ingredient may be appropriate for an adult. The daily dose can be administered in 1–4 doses per day.

In addition to the compound(s) of Formula I, the composition for therapeutic use may also comprise one or more non-toxic, pharmaceutically acceptable carrier materials or excipients. The term "carrier" material or "excipient" herein means any substance, not itself a therapeutic agent, used as a carrier and/or diluent and/or adjuvant, or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients can include, by way of illustration and not limitation, diluents, disintegrants, binding agents, adhesives, wetting agents, polymers, lubricants, glidants, substances added to mask or counteract a disagreeable taste or odor, flavors, dyes, fragrances, and substances added to improve appearance of the composition. Acceptable excipients include lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl-pyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose, or other methods known to those skilled in the art. For oral administration, the pharmaceutical composition may be in the form of, for example, a tablet, capsule, suspension or liquid. If desired, other active ingredients may be included in the composition.

In addition to the oral dosing, noted above, the compositions of the present invention may be administered by any suitable route, in the form of a pharmaceutical composition adapted to such a route, and in a dose effective for the treatment intended. The compositions may, for example, be administered parenterally, e.g., intravascularly, intraperitoneally, subcutaneously, or intramuscularly. For parenteral administration, saline solution, dextrose solution, or water may be used as a suitable carrier. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

The serotonin type 3 receptor ($5HT_3R$) is a member of a superfamily of ligand-gated ion channels, which includes the muscle and neuronal nAChR, the glycine receptor, and the γ-aminobutyric acid type A receptor. Like the other members of this receptor superfamily, the $5HT_3R$ exhibits a large degree of sequence homology with α7 nAChR but functionally the two ligand-gated ion channels are very different. For example, α7 nAChR is rapidly inactivated, is highly permeable to calcium and is activated by acetylcholine and nicotine. On the other hand, $5HT_3R$ is inactivated slowly, is relatively impermeable to calcium and is activated by serotonin. These experiments suggest that the α7 nAChR and $5HT_3R$ proteins have some degree of homology, but function very differently. Indeed the pharmacology of the channels is very different. For example, Ondansetron, a highly selective $5HT_3R$ antagonist, has little activity at the α7 nAChR. The converse is also true. For example, GTS-21, a highly selective α7 nAChR agonist, has little activity at the $5HT_3R$.

α7 nAChR is a ligand-gated $Ca^{++}$ channel formed by a homopentamer of α7 subunits. Previous studies have established that α-bungarotoxin (α-btx) binds selectively to this homopetameric, α7 nAChR subtype, and that α7 nAChR has a high affinity binding site for both α-btx and methyllycaconitine (MLA). α7 nAChR is expressed at high levels in the hippocampus, ventral tegmental area and ascending cholinergic projections from nucleus basilis to thalamocortical areas. α7 nAChR agonists increase neurotransmitter release, and increase cognition, arousal, attention, learning and memory.

Data from human and animal pharmacological studies establish that nicotinic cholinergic neuronal pathways control many important aspects of cognitive function including attention, learning and memory (Levin, E. D., *Psychopharmacology*, 108:417–31, 1992; Levin, E. D. and Simon B. B., *Psychopharmacology*, 138:217–30, 1998). For example, it is well known that nicotine increases cognition and attention in humans. ABT418, a compound that activates (α4β2 and α7 nAChR, improves cognition and attention in clinical trials of Alzheimer's disease and attention-deficit disorders (Potter, A. et. al., *Psychopharmacology* (*Berl*)., 142(4):334–42, March 1999; Wilens, T. E. et. al., *Am. J. Psychiatry*, 156(12): 1931–7, December 1999). It is also clear that nicotine and selective but weak α7 nAChR agonists increase cognition and attention in rodents and non-human primates.

Schizophrenia is a complex multifactorial illness caused by genetic and non-genetic risk factors that produce a constellation of positive and negative symptoms. The positive symptoms include delusions and hallucinations and the negative symptoms include deficits in affect, attention, cognition and information processing. No single biological element has emerged as a dominant pathogenic factor in this disease. Indeed, it is likely that schizophrenia is a syndrome that is produced by the combination of many low penetrance risk factors. Pharmacological studies established that dopamine receptor antagonists are efficacious in treating the overt psychotic features (positive symptoms) of schizophrenia such as hallucinations and delusions. Clozapine, an "atypical" antipsychotic drug, is novel because it is effective in treating both the positive and some of the negative symptoms of this disease. Clozapine's utility as a drug is greatly limited because continued use leads to an increased risk of agranulocytosis and seizure. No other antipsychotic drug is effective in treating the negative symptoms of schizophrenia. This is significant because the restoration of cognitive functioning is the best predictor of a successful clinical and functional outcome of schizophrenic patients (Green, M. F., *Am J Psychiatry*, 153:321–30, 1996). By extension, it is clear that better drugs are needed to treat the cognitive disorders of schizophrenia in order to restore a better state of mental health to patients with this disorder.

One aspect of the cognitive deficit of schizophrenia can be measured by using the auditory event-related potential (P50) test of sensory gating. In this test, electroencepholographic (EEG) recordings of neuronal activity of the hippocampus are used to measure the subject's response to a series of auditory "clicks" (Adler, L. E. et. al., *Biol. Psychiatry*, 46:8–18, 1999). Normal individuals respond to the first click with greater degree than to the second click. In general, schizophrenics and schizotypal patients respond to both clicks nearly the same (Cullum, C. M. et. al., *Schizophr. Res.*, 10:131–41, 1993). These data reflect a schizophrenic's inability to "filter" or ignore unimportant information. The sensory gating deficit appears to be one of the key pathological features of this disease (Cadenhead, K. S. et. al.,*Am. J. Psychiatry*, 157:55–9, 2000). Multiple studies show that nicotine normalizes the sensory deficit of schizophrenia (Adler, L. E. et. al.,*Am. J. Psychiatry*, 150:1856–61, 1993). Pharmacological studies indicate that nicotine's effect on sensory gating is via the α7 nAChR (Adler, L. E. et. al., *Schizophr. Bull.*, 24:189–202, 1998). Indeed, the biochemical data indicate that schizophrenics have 50% fewer of α7 nAChR receptors in the hippocampus, thus giving a rationale to partial loss of α7 nAChR functionality (Freedman, R. et. al., *Biol. Psychiatry*, 38:22–33, 1995). Interestingly, genetic data indicate that a polymorphism in the promoter region of the α7 nAChR gene is strongly associated with the sensory gating deficit in schizophrenia (Freedman, R. et. al., Proc. Nat'l Acad. Sci. USA, 94(2):587–92, 1997; Myles-Worsley, M. et. al., Am. J. Med. Genet, 88(5):544–50, 1999). To date, no mutation in the coding region of the α7 nAChR has been identified. Thus, schizophrenics express the same α7 nAChR as non-schizophrenics.

Selective α7 nAChR agonists may be found using a functional assay on FLIPR (see WO 00/73431 A2). FLIPR is designed to read the fluorescent signal from each well of a 96 or 384 well plate as fast as twice a second for up to 30 minutes. This assay may be used to accurately measure the functional pharmacology of α7 nAChR and 5HT$_3$R. To conduct such an assay, one uses cell lines that expressed functional forms of the α7 nAChR using the α7/5-HT$_3$ channel as the drug target and cell lines that expressed functional 5HT$_3$R. In both cases, the ligand-gated ion channel was expressed in SH-EP1 cells. Both ion channels can produce robust signal in the FLIPR assay.

The compounds of the present invention are α7 nAChR agonists and may be used to treat a wide variety of diseases. For example, they may be used in treating schizophrenia, and psychosis.

Schizophrenia is a disease having multiple aspects. Currently available drugs are generally aimed at controlling the positive aspects of schizophrenia, such as delusions. One drug, Clozapine, is aimed at a broader spectrum of symptoms associated with schizophrenia. This drug has many side effects and is thus not suitable for many patients. Thus, there is a need for a drug to treat the cognitive and attention deficits associated with schizophrenia. Similarly, there is a need for a drug to treat the cognitive and attention deficits associated with schizoaffective disorders, or similar symptoms found in the relatives of schizophrenic patients.

Psychosis is a mental disorder characterized by gross impairment in the patient's perception of reality. The patient may suffer from delusions, and hallucinations, and may be incoherent in speech. His behavior may be agitated and is often incomprehensible to those around him. In the past, the term psychosis has been applied to many conditions that do not meet the stricter definition given above. For example, mood disorders were named as psychoses.

There are a variety of antipsychotic drugs. The conventional antipsychotic drugs include Chlorpromazine, Fluphenazine, Haloperidol, Loxapine, Mesoridazine, Molindone, Perphenazine, Pimozide, Thioridazine, Thiothixene, and Trifluoperazine. These drugs all have an affinity for the dopamine 2 receptor.

These conventional antipsychotic drugs have several side effects, including sedation, weight gain, tremors, elevated prolactin levels, akathisia (motor restlessness), dystonia and muscle stiffness. These drugs may also cause tardive dyskinesia. Unfortunately, only about 70% of patients with schizophrenia respond to conventional antipsychotic drugs. For these patients, atypical antipsychotic drugs are available.

Atypical antipsychotic drugs generally are able to alleviate positive symptoms of psychosis while also improving negative symptoms of the psychosis to a greater degree than conventional antipsychotics. These drugs may improve neurocognitive deficits. Extrapyramidal (motor) side effects are not as likely to occur with the atypical antipsychotic drugs, and thus, these atypical antipsychotic drugs have a lower risk of producing tardive dyskinesia. Finally these atypical antipsychotic drugs cause little or no elevation of prolactin. Unfortunately, these drugs are not free of side effects. Although these drugs each produce different side effects, as a group the side effects include: agranulocytosis; increased risk of seizures, weight gain, somnolence, dizziness, tachycardia, decreased ejaculatory volume, and mild prolongation of QTc interval.

Finally, the compounds of the present invention may be used in combination therapy with typical and atypical antipsychotic drugs. All compounds within the present invention are useful for and may also be used in combination with each other to prepare pharmaceutical compositions. Such combination therapy lowers the effective dose of the anti-psychotic drug and thereby reduces the side effects of the antipsychotic drugs. Some typical anti-psychotic drugs that may be used in the practice of the invention include Haldol. Some atypical anti-psychotic drugs include Ziprasidone, Olanzapine, Resperidone, and Quetiapine.

Compounds of the present invention can generally be prepared using the synthetic schemes illustrated in Schemes 1 and 2. Starting materials can be prepared by procedures described in these schemes or by procedures that would be well known to one of ordinary skill in organic chemistry. The variables used in the Schemes are defined herein.

Compounds of Formula I can be prepared as shown in Scheme 1. The key step in the preparation of this class of compounds is the coupling of commercially available 3-aminoquinuclidine (R$_2$=H) with the requisite activated carboxylic acid (Lv=OH), acid chloride (Lv=Cl), or mixed anhydride (e.g., Lv=diphenylphosphoryl, or acyloxy of the general formula of —O—C(O)—R$_{Lv}$, where R$_{Lv}$ includes phenyl or t-butyl). Suitable activating reagents are well known in the art, for examples see Kiso, Y.; Yajima, H. "Peptides" pp. 39–91, San Diego, Calif., Academic Press, (1995).

Scheme 1

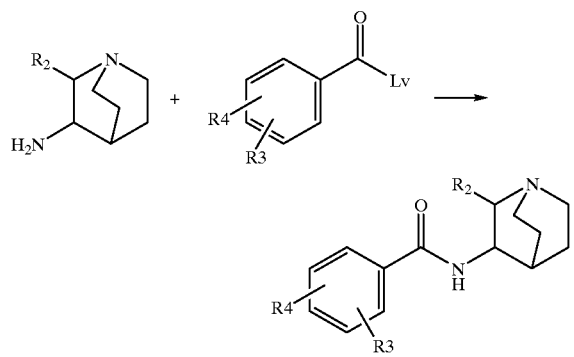

One of ordinary skill in the art will recognize that the methods described for the reaction of the unsubstituted 3-aminoquinuclidine (R$_2$=H) are equally applicable to substituted compounds (R$_2$≠H). Such compounds can be prepared by reduction of the oxime of the corresponding 3-quinuclidinone (see J. Labelled Compds. Radiopharm., 53–60 (1995) and J. Med. Chem. 988–995, (1998)). The oximes can be prepared by treatment of the 3-quinuclidinones with hydroxylamine hydrochloride in the presence of a base. The 3-quinuclidinones, where R$_2$=substituted alkyl, cycloalkyl, substituted benzyl, can be prepared by known procedures (see Tet. Lett. 1015–1018, (1972), J. Am. Chem. Soc. 1278–1291 (1994), J. Am. Chem. Soc. 4548–4552 (1989), Tetrahedron, 1139–1146 (2000)). The 3-quinuclidinones, where R$_2$=aryl, can be prepared by palladium catalyzed arylation as described in J. Am. Chem. Soc. 1473–1478 (1999) and J. Am. Chem. Soc. 1360–1370 (2000).

It will be apparent to those skilled in the art that the requisite carboxylic acids can be obtained commercially or can be synthesized by known procedures. The acid required in Example 1 is synthesized by acetylation of the corresponding phenol with acetylchloride. The acids in Examples 2, 8–16 are synthesized from the corresponding esters by hydrolysis. Typical hydrolysis procedures are well known in the art. Preferably, the ester is treated with aqueous lithium hydroxide in a solvent such as dioxane. The requisite esters are synthesized from the reaction of a phenol and arylboronic acid as described in *Tet. Lett.*, 2937–2940 (1998). The phenol and boronic acid are reacted in the presence of a copper salt like copper (II) acetate and a base like TEA (Scheme 2). The acids for Examples 3–7 are commercially available. The acids required for Examples 17–22 are synthesized from the corresponding esters by hydrolysis as described above. The esters are synthesized by the reaction of a thiophenol with an aryl halide as described in *Synlett*, 1579–1581 (1999). Namely, the thiophenol and aryl iodide are heated in the presence of a palladium (0) source such as tetrakis(triphenylphosphine)palladium (0) and a base, preferably sodium tert-butoxide.

Scheme 2

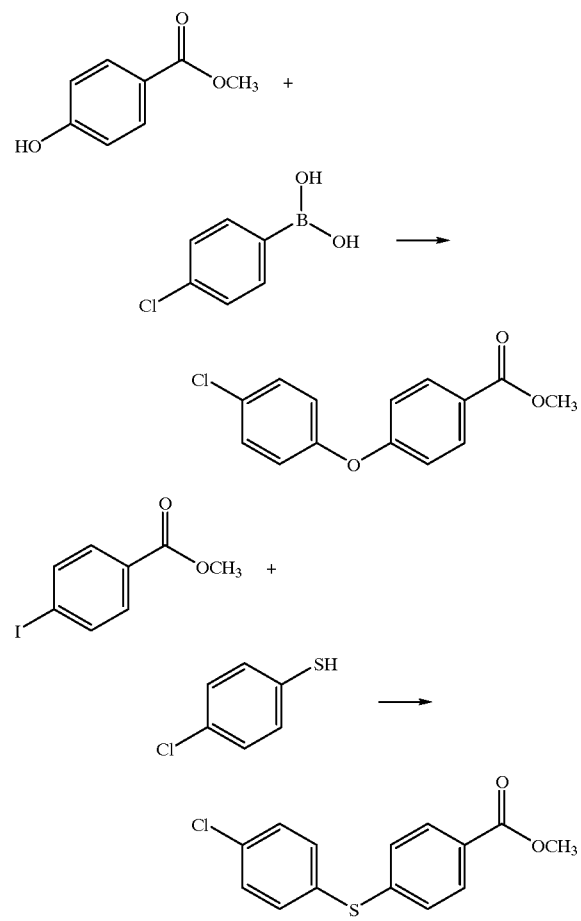

There are a variety of methods for constructing thioamides. One can treat the corresponding amide with a reagent such as Lawesson's reagent (2,4-bis(4-methoxyphenyl)-1,3-dithia-2,4-diphosphetane-2,4-disulfide), as shown in Scheme 3 (see Lawesson et. al. in *Bull. Soc. Chim. Belg.*, 229 (1978)), or $P_4S_{10}$ (see *Chem. Rev.*, 45 (1961)).

Scheme 3

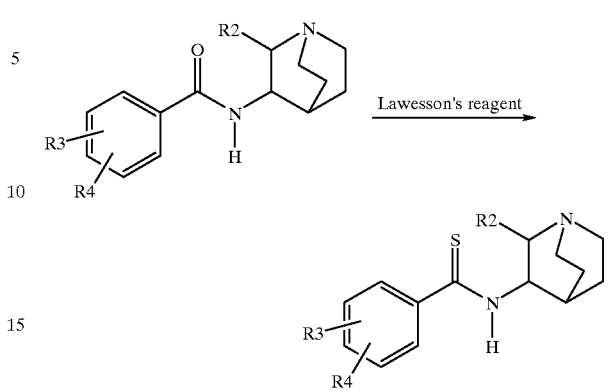

Alternatively one can react a dithiocarboxylic ester with the corresponding quinuclidine to form the same thioamide.

The following examples are provided as examples and are not intended to limit the scope of this invention to only those provided examples and named compounds. Also, the salts made in the examples are only exemplary and are not intended to limit the invention. Any pharmaceutically acceptable salt can be made by one of ordinary skill in the art. Further, the naming of specific stereoisomers is for exemplification, and is not intended to limit in anyway the scope of the invention. The invention includes the following examples in pure stereoisomeric form or as racemic mixtures.

EXAMPLE 1

N-[(3R)-1-azabicyclo[2.2.2]oct-3-yl]-4-(4-hydroxyphenoxy)benzamide

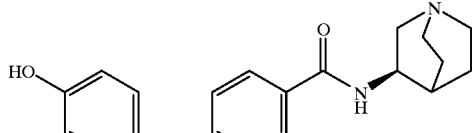

Step A. Preparation of 4-(4-acetoxyphenoxy) benzoic Acid

Acetylchloride (1.5 mL, 21 mmol) is added to a solution of 4-(4-hydroxyphenoxy)benzoic acid (2.3 g, 10 mmol) and TEA (2.9 mL, 21 mmol) in $CH_2Cl_2$ (50 mL). The reaction is stirred for 16 hours at room temperature. The reaction mixture is diluted with $CH_2Cl_2$ and washed three times with saturated $NaHCO_3$. The organic layer is dried over $MgSO_4$, filtered and concentrated in vacuo. The resulting material is dissolved in dioxane (6 mL). Aqueous LiOH (1N, 930 μL) is added, and the reaction is allowed to stir for one hour at room temperature. The reaction mixture is poured into $CH_2Cl_2$ and washed twice with $KHSO_4$. The organic layer is dried over $MgSO_4$, filtered and concentrated in vacuo to give the desired acid (1.5 g, 87%). $^1$H NMR (300 MHz, DMSO) δ12.80, 7.96, 7.23–7.13, 7.04, 2.29.

Step B. Preparation of N-[(3R)-1-azabicyclo[2.2.2] oct-3-yl]-4-(4-hydroxyphenoxy)benzamide TEA (830 μL, 6.0 mmol) is added to a suspension of the product of Step A (1.5 g, 5.7 mmnol) in $CH_2Cl_2$ (5 mL).

Diphenylchlorophosphate (1.2 mL, 5.7 mmol) is added and the resulting solution is stirred at room temperature for 30 minutes. This solution is added to a solution of (R)-3-aminoquinuclidine (680 mg, 5.4 mmol) in DMF (6 mL). The resulting solution is stirred overnight at room temperature. MeOH is added and the mixture is poured through a column of AG50W×2 ion exchange resin (H$^+$ form). The resin is washed with MeOH and then the product is eluted with 5% TEA in MeOH. The eluent is evaporated to dryness. The hydrochloride salt is formed and triturated with hot CH$_3$CN to yield the desired product (1.2 g, 60%). MS for C$_{20}$H$_{22}$N$_2$O$_3$ (ESI) (M+H)$^+$ m/z 339.

EXAMPLE 2

N-[(3R)-1-azabicyclo[2.2.2]oct-3-yl]-4-(4-acetamidophenoxy)benzamide

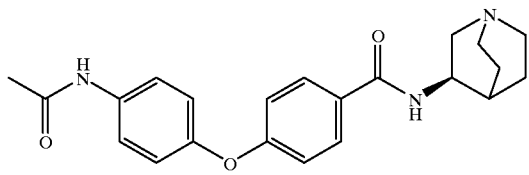

Step C. Preparation of Methyl 4-(4-acetamidophenoxy)benzoate

Dry air is bubbled through a solution of 4-acetamidophenol (320 mg, 2.1 mmol), copper(II) acetate (384 mg, 2.1 mmol), TEA (1.5 mL, 10.5 mol), (4-methoxycarbonylphenyl)boronic acid (760 mg, 4.2 mmol), and powdered molecular sieves (2 g) in CH$_2$Cl$_2$ (21 mL) for 16 hours at room temperature. The resulting material is concentrated and purified by flash column chromatography (25–50% EtOAc in heptane) to give the desired product (450 mg, 75%). $^1$H NMR (300 MHz, DMSO) δ8.01, 7.54, 7.27, 7.05, 6.98, 3.92, 2.22.

Step D. Preparation of 4-(4-acetamidophenoxy) benzoic Acid

Aqueous LiOH (1M, 3.12 mL) is added to a suspension of the product of Step C (445 mg, 1.6 mmol) in dioxane (6 mL). The reaction is stirred for 90 minutes at room temperature. Concentrated HCl (1.5 mL) is added to lower the pH to less than 6 and the resulting precipitate is collected by filtration. The filter cake is washed with water then dried to give the desired product (337 mg, 80%). MS for C$_{15}$H$_{13}$NO$_4$ (ESI) (M−H)$^-$ m/z 270.

Step E. Preparation of N-[(3R)-1-azabicyclo[2.2.2] oct-3-yl]-4-(4-acetamidophenoxy)benzamide TEA (130 μL, 1.0 mmol) is added to a suspension of the product of Step D (250 mg, 0.9 mmol) in CH$_2$Cl$_2$ (9 mL). Diphenylchlorophosphate (190 μL, 0.9 mmol) is added and the resulting solution is stirred at room temperature for 30 minutes. This solution is added to a solution of (R)-3-aminoquinuclidine (110 mg, 0.88 mmol) in DMF (1 mL). The resulting solution is stirred overnight at room temperature. MeOH is added and the mixture is poured through a column of AG50W×2 ion exchange resin (H$^+$ form). The resin is washed with MeOH and then the product is eluted with 5% TEA in MeOH. The eluent is evaporated to dryness. The product is crystallized from CH$_3$CN to yield the desired product (130 mg, 39%). MS for C$_{22}$H$_{25}$N$_3$O$_3$ (ESI) (M+H)$^+$ m/z 380.

EXAMPLE 3

N-[(3R)-1-azabicyclo[2.2.2]oct-3-yl]-4-phenoxybenzamide

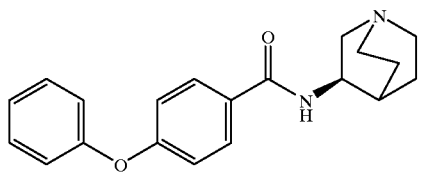

TEA (50 μL, 0.35 mmol) is added to a suspension of 4-phenoxybenzoic acid (75 mg, 0.35 mmol) in CH$_2$Cl$_2$ (1 mL). Diphenylchlorophosphate (62 μL, 0.3 mmol) is added and the resulting solution is stirred at room temperature for 30 minutes. A solution of (R)-3-aminoquinuclidine (1M in DMF, 0.2 mL, 0.2 mmol) is added and the resulting solution is stirred overnight at room temperature. MeOH is added and the mixture is poured through a column of AG50W×2 ion exchange resin (H$^+$ form). The resin is washed with MeOH and then the product is eluted with 5% TEA in MeOH. The eluent is evaporated to dryness to yield the desired product (49 mg, 76%). MS for C$_{20}$H$_{22}$N$_2$O$_2$ (ESI) (M+H)$^+$ m/z 323.

EXAMPLES 4–7

The following compounds are made from the corresponding carboxylic acids according to the procedure of Example 3, making non-critical variations.

Example 4. N-[(3R)-1-azabicyclo[2.2.2]oct-3-yl]-4-benzylbenzamide (from 4-benylbenzoic acid). MS for C$_{21}$H$_{24}$N$_2$O (ESI) (M+H)$^+$ m/z 323.

Example 5. N-[(3R)-1-azabicyclo[2.2.2]oct-3-yl]-4-(phenylsulfanyl)-benzamide, (from 4-(phenylsulfanyl) benzoic acid). MS for C$_{20}$H$_{22}$N$_2$OS (ESI) (M+H)$^+$ m/z 339.

Example 6. N-[(3R)-1-azabicyclo[2.2.2]oct-3-yl]-3-phenoxybenzamide (from 3-phenoxybenzoic acid). MS for C$_{20}$H$_{22}$N$_2$O$_2$ (ESI) (M+H)$^+$ m/z 323.

Example 7. N-[(3R)-1-azabicyclo[2.2.2]oct-3-yl]-4-benzoylbenzamide (from 4-benzoylbenzoic acid). MS for C$_{21}$H$_{22}$N$_2$O$_2$ (ESI) (M+H)$^+$ m/z 335.

EXAMPLE 8

N-[(3R)-1-azabicyclo[2.2.2]oct-3-yl]-4-(4-fluorophenoxy)benzamide

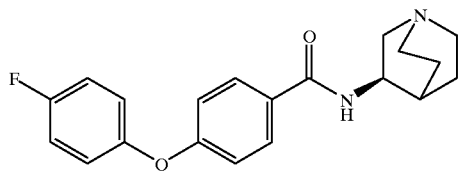

Step F. Preparation of 4-(4-fluorophenoxy)benzoic Acid

To a flask with 4-fluorophenyl boronic acid (2.1 g, 15 mmol), copper(II) acetate (1.4 g, 7.5 mmol), activated powdered molecular sieves (approximately 2 g), and methyl 4-hydroxybenzoate (1.2 g, 7.5 mmol) is added TEA (5.2 mL, 38 mmol) followed by CH$_2$Cl$_2$ (75 mL). The reaction is stirred for 16 hours at room temperature with air bubbling through it. The reaction mixture is diluted with CH₂Cl₂ and filtered through silica gel. The silica gel is washed with EtOAc-heptane. The solution is concentrated in vacuo and dissolved in dioxane (15 mL). To this solution is added aqueous LiOH (1N, 15 mL) and stirred for 18 hours at room temperature. To this reaction mixture is added aqueous HCl (1N) until acidic, having a pH less than 6. The resulting precipitate is collected by filtration and rinsed with water, and dried in vacuo to give the desired product (1.6 g, 90%). MS for $C_{13}H_9FO_3$ (ESI) (M–H)⁻ m/z 231.

Step G. Preparation of N-[(3R)-1-azabicyclo[2.2.2] oct-3-yl]-4-(4-fluorophenoxy)benzamide TEA (50 μL, 0.35 mmol) is added to a suspension of the acid from Step F (81 mg, 0.35 mmol) in CH₂Cl₂ (1 mL). Diphenylchlorophosphate (62 μL, 0.3 mmol) is added and the resulting solution is stirred at room temperature for 30 minutes. A solution of (R)-3-aminoquinuclidine (1.0M in CH₃CN, 0.2 mL, 0.2 mmol) is added and the resulting solution is shaken overnight at room temperature. MeOH is added and the mixture is poured through a column of AG50W×2 ion exchange resin (H⁺ form). The resin is washed with MeOH and then the product is eluted with 5% TEA in MeOH. The eluent is evaporated to dryness to yield the desired product (58 mg, 85%). MS for $C_{20}H_{21}FN_2O_2$ (ESI) (M+H)⁺ m/z 341.

EXAMPLES 9–16

The following compounds are made from the corresponding boronic acids according to the procedure of Example 8, making non-critical variations.

Example 9. N-[(3R)-1-azabicyclo[2.2.2]oct-3-yl]-4-(2-fluorophenoxy)-benzamide (from 2-fluorophenylboronic acid). MS for $C_{20}H_{21}FN_2O_2$ (ESI) (M+H)⁺ m/z 341.

Example 10. N-[(3R)-1-azabicyclo[2.2.2]oct-3-yl]-4-(3-fluorophenoxy)-benzamide (from 3-fluorophenylboronic acid). MS for $C_{20}H_{21}FN_2O_2$ (ESI) (M+H)⁺ m/z 341.

Example 11. N-[(3R)-1-azabicyclo[2.2.2]oct-3-yl]-4-(2-chlorophenoxy)-benzamide (from 2-chlorophenylboronic acid). MS for $C_{20}H_{21}ClN_2O_2$ (ESI) (M+H)⁺ m/z 357.

Example 12. N-[(3R)-1-azabicyclo[2.2.2]oct-3-yl]-4-(3-chlorophenoxy)-benzamide (from 3-chlorophenylboronic acid). MS for $C_{20}H_{21}ClN_2O_2$ (ESI) (M+H)⁺ m/z 357.

Example 13. N-[(3R)-1-azabicyclo[2.2.2]oct-3-yl]-4-(4-chlorophenoxy)-benzamide (from 4-chlorophenylboronic acid). MS for $C_{20}H_{21}ClN_2O_2$ (ESI) (M+H)⁺ m/z 357.

Example 14. N-[(3R)-1-azabicyclo[2.2.2]oct-3-yl]-4-(2-methoxyphenoxy)-benzamide (from 2-methoxyphenylboronic acid). MS for $C_{21}H_{24}N_2O_3$ (ESI) (M+H)⁺ m/z 353.

Example 15. N-[(3R)-1-azabicyclo[2.2.2]oct-3-yl]-4-(3-methoxyphenoxy)-benzamide (from 3-methoxyphenylboronic acid). MS for $C_{21}H_{24}N_2O_3$ (ESI) (M+H)⁺ m/z 353.

Example 16. N-[(3R)-1-azabicyclo[2.2.2]oct-3-yl]-4-(4-methoxyphenoxy)-benzamide (from 4-methoxyphenylboronic acid). MS for $C_{21}H_{24}N_2O_3$ (ESI) (M+H)⁺ m/z 353.

EXAMPLE 17

N-[(3R)-1-azabicyclo[2.2.2]oct-3-yl]-4-(3-chlorophenylsulfanyl)benzamide

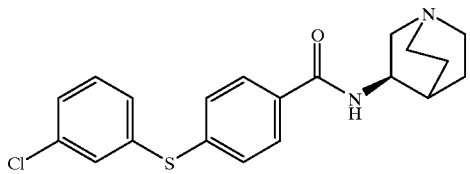

Step H. Preparation of Methyl 4-(3-chlorosulfanyl) benzoate

A flask containing 3-chlorothiophenol (0.29 mL, 2.5 mmol), potassium tert-butoxide (0.28 g, 2.5 mmol), tetrakis (triphenylphosphine)palladium (0) (0.23 g, 0.2 mmol), and methyl 4-iodobenzoate (0.66 g, 2.5 mmol) is vacuum purged and N₂ filled three times. To this flask is added THF (50 mL) and the mixture is stirred at reflux for 24 hours. The solution is diluted with CH₂Cl₂ and extracted three times with 1N NaOH. The organic layer is dried over MgSO₄ and concentrated in vacuo. The crude product is purified by flash-column chromatography (gradient of 0–1% EtOAc in heptane) to give the desired product (0.53 g, 90%). ¹H NMR (300 MHz, CDCl₃) δ7.96, 7.44–7.43, 7.34–7.29, 3.92.

Step I. Preparation of 4-(3-chlorosulfanyl)benzoic Acid

The product of Step H (0.53 g, 1.89 mmol) is dissolved in dioxane (4 mL) followed by addition of aqueous LiOH (1M, 4 mL). The mixture is stirred at room temperature for 5 hours then acidified with aqueous 1N HCl to a pH of less than 6. The resulting precipitate is collected by filtration, rinsed with water, and dried in vacuo to give the desired product (0.44 g, 89%). MS for $C_{13}H_9ClO_2S$ (ESI) (M–H)⁻ m/z 263.

Step J. Preparation of N-[(3R)-1-azabicyclo[2.2.2] oct-3-yl]-4-(3-chlorophenylsulfanyl)benzamide TEA (50 μL, 0.35 mmol) is added to a suspension of the acid from Step I (93 mg, 0.35 mmol) in CH₂Cl₂ (1 mL). Diphenylchlorophosphate (62 μL, 0.3 mmol) is added and the resulting solution is stirred at room temperature for 30 minutes. A solution of (R)-3-aminoquinuclidine (1.0M in DMF, 0.2 mL, 0.2 mmol) is added and the resulting solution is allowed to sit overnight at room temperature. MeOH is added and the mixture is poured through a column of AG50W×2 ion exchange resin (H⁺ form). The resin is washed with MeOH and then the product is eluted with 5% TEA in MeOH. The eluent is evaporated to dryness to yield the desired product (59 mg, 75%). MS for $C_{20}H_{21}ClN_2OS$ (ESI) (M+H)⁺ m/z 373.

EXAMPLES 18–22

The following compounds are made from the corresponding thiophenols according to the procedure of Example 17, making non-critical variations.

Example 18. N-[(3R)-1-azabicyclo[2.2.2]oct-3-yl]-4-(4-chlorophenylsulfanyl)benzamide (from 4-chlorothiophenol). MS for $C_{20}H_{21}ClN_2OS$ (ESI) (M+H)⁺ m/z 373.

Example 19. N-[(3R)-1-azabicyclo[2.2.2]oct-3-yl]-4-(2-chlorophenylsulfanyl)benzamide (from 2-chlorothiophenol). MS for $C_{20}H_{21}ClN_2OS$ (ESI) $(M+H)^+$ m/z 373.

Example 20. N-[(3R)-1-azabicyclo[2.2.2]oct-3-yl]-4-(4-methoxyphenylsulfanyl)benzamide (from 4-methoxythiophenol). MS for $C_{21}H_{24}N_2O_2S$ (ESI) $(M+H)^+$ m/z 369.

Example 21. N-[(3R)-1-azabicyclo[2.2.2]oct-3-yl]-4-(3-methoxyphenylsulfanyl)benzamide (from 3-methoxythiophenol). MS for $C_{21}H_{24}N_2O_2S$ (ESI) $(M+H)^+$ m/z 369.

Example 22. N-[(3R)-1-azabicyclo[2.2.2]oct-3-yl]-4-(2-methoxyphenylsulfanyl)benzamide (from 2-methoxythiophenol). MS for $C_{21}H_24N2O_2S$ (ESI) $(M+H)^+$ m/z 369.

EXAMPLE 23

N-(2-methyl-1-azabicyclo[2.2.2]oct-3-yl)-4-phenoxybenzamide Fumarate

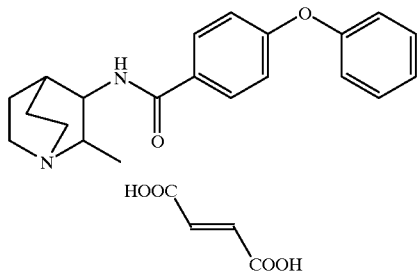

Step K: Preparation of 2-methylenequinuclidin-3-one

A mixture of 2-methylene-3-quinuclidinone dihydrate hydrochloride (25.7 g, 0.1225 mol, 1 eq) and $K_2CO_3$ (67.0 g, 0.4848 mol, 4 eq) is dissolved in 125 mL water and 200 mL $CH_2Cl_2$ and stirred vigorously. After 16 h, the layers are separated and the aqueous layer is extracted with $CH_2Cl_2$. The combined organic layers are dried over $MgSO_4$, filtered and concentrated to give 14.75 g (88%) of 2-methylenequinuclidin-3-one as a yellow oil. MS (ES) for $C_8H_{11}NO$ m/z 138.1 $(M+H)^+$.

Step L: Preparation of 2-methylquinuclidin-3-one Hydrochloride

The product from Step K (14.75 g, 0.1075 mol, 1 eq), formic acid (10.4 g, 0.2150 mol, 2 eq) and $(Ph_3P)_3RuCl_2$ (0.21 g, 0.21 mmol) are dissolved in 100 mL THF. The mixture is heated under reflux. Fresh portions of catalyst (0.58 g, 0.59 mmol (total)) and formic acid (1.2 g, 0.026 mol) are added periodically over the course of the reaction. After 72 h, the mixture is concentrated in vacuo. The residue is taken up in ether and excess HCl in dioxane (27 mL, 4.0 M) is added. The solids are washed with ether and recrystallized from EtOH to afford 14.4 g (76%) of 2-methylquinuclidin-3-one hydrochloride as a white solid. MS (ESI) for $C_8H_{13}NO$ m/z 140.2 $(M+H)^+$.

Step M: Preparation of 2-methyl-1-azabicyclo[2.2.2]octan-3-one Oxime

2-Methylquinuclidin-3-one hydrochloride from Step L (5.3 g, 30.2 mmol, 1 eq), hydroxylamine hydrochloride (2.5 g, 36.4 mmol, 1.2 eq) and sodium acetate trihydrate (12.4 g, 90.9 mmol, 3 eq) are suspended in 70 mL EtOH and stirred at room temperature. After 24 h, the mixture is concentrated in vacuo. The residue is suspended in $CHCl_3$ and the solids are filtered. The solids are rinsed with excess $CH_3CN$. The combined organic washes are concentrated in vacuo to give 4.65 g (100%) of 2-methyl-1-azabicyclo[2.2.2]octan-3-one oxime. MS (ESI) for $C_8H_{14}N_2O$ m/z 155.2 $(M+H)^+$.

Step N: Preparation of 2-methylquinuclidin-3-amine Dihydrochloride

Sodium (7.0 g, 0.303 mol, 10 eq) is added in portions to a solution of 2-methyl-1-azabicyclo[2.2.2]octan-3-one oxime from Step M (4.65 g, 30.2 mmol, 1 eq) in 100 mL n-propanol. The mixture is heated under reflux. After about 12 h, the mixture is cooled and 80 mL of water is added. The layers are separated and the aqueous layer is extracted with $CHCl_3$. The combined organic layers are dried over $MgSO_4$ and filtered. An excess of HCl in dioxane (15 mL, 4.0M) is added to solution and the solvent is removed to give 6.0 g (93%) of 2-methylquinuclidin-3-amine dihydrochloride as an oil. A hygroscopic solid is obtained by trituration of the oil in hot IPA. MS (ESI) for $C_8H_{16}N_2$ m/z 141.3 $(M+H)^+$.

Step O: Preparation of N-(2-methyl-1-azabicyclo[2.2.2]oct-3-yl)-4-phenoxybenzamide Fumarate TEA (0.32 mL, 2.3 mmol, 1 eq) is added to a solution of 4-phenoxybenzoic acid 0.50 g, 2.3 mmol, 1 eq) in 15 mL THF. Diphenylchlorophosphate (0.44 mL, 2.3 mmol, 1 eq) is added and the mixture is stirred at room temperature. After 0.5 h, a suspension of 2-methylquinuclidin-3-amine dihydrochloride from Step N (0.49 g, 2.3 mmol, 1 eq) and TEA (1.30 mL, 9.2 mmol, 4 eq) in THF is added and the resulting mixture is stirred overnight at room temperature. 1N NaOH is added and the aqueous layer is extracted with $CHCl_3$. The combined organic layers are dried over $MgSO_4$, filtered and concentrated to provide 0.64 g (82%) of N-(2-methyl-1-azabicyclo[2.2.2]oct-3-yl)-4-phenoxybenzamide. MS (ESI) for $C_{21}H_{24}N_2O_2$ m/z 337.3 $(M+H)^+$. The fumaric acid salt of the product is made and crystallized from IPA to give the product as a white solid. Reverse phase HPLC (ZORBAX Eclipse XDB-C8, 4.6 mm×15 cm, 75:5:20 $H_2O/CH_3CN$/IPA) reveals an 85:15 trans/cis mixture of isomers.

The present invention also includes, by representation but not limitation, any one of the following or combination of the following compounds and pharmaceutically acceptable salts thereof, both of which can be made by one of ordinary skill in the art using the procedures provided making non-critical changes:

N-[(2S,3R)-2-methyl-1-azabicyclo[2.2.2]oct-3-yl]-4-(4-hydroxyphenoxy)benzamide; N-[(2S,3R)-2-methyl-1-azabicyclo[2.2.2]oct-3-yl]-4-(4-acetamidophenoxy)benzamide; N-[(2S,3R)-2-methyl-1-azabicyclo[2.2.2]oct-3-yl]-4-phenoxybenzamide; N-[(2S,3R)-2-methyl-1-azabicyclo[2.2.2]oct-3-yl]-4-benzylbenzamide; N-[(2S,3R)-2-methyl-1-azabicyclo[2.2.2]oct-3-yl]-4-(phenylsulfanyl)benzamide; N-[(2S,3R)-2-methyl-1-azabicyclo[2.2.2]oct-3-yl]-3-phenoxybenzamide; N-[(2S,3R)-2-methyl-1-azabicyclo[2.2.2]oct-3-yl]-4-benzoylbenzamide; N-[(2S,3R)-2-methyl-1-azabicyclo[2.2.2]oct-3-yl]-4-(4-fluorophenoxy)benzamide; N-[(2S,3R)-2-methyl-1-azabicyclo[2.2.2]oct-3-yl]-4-(2-fluorophenoxy)benzamide; N-[(2S,3R)-2-methyl-1-azabicyclo[2.2.2]oct-3-yl]-4-(3-fluorophenoxy)benzamide; N-[(2S,3R)-2-methyl-1-azabicyclo[2.2.2]oct-3-yl]-4-(2-chlorophenoxy)benzamide; N-[(2S,3R)-2-methyl-1-azabicyclo[2.2.2]oct-3-yl]-4-(3-chlorophenoxy)benzamide; N-[(2S,3R)-2-methyl-1- azabicyclo[2.2.2]oct-3-yl]-4-(4-chlorophenoxy) benzamide; N-[(2S,3R)-2-methyl-1-azabicyclo[2.2.2]oct-3-yl]-4-(2-methoxyphenoxy)benzamide; N-[(2S,3R)-2-methyl-1-azabicyclo[2.2.2]oct-3-yl]-4-(3-methoxyphenoxy)benzamide; N-[(2S,3R)-2-methyl-1-azabicyclo[2.2.2]oct-3-yl]-4-(4-methoxyphenoxy) benzamide; N-[(2S,3R)-2-methyl-1-azabicyclo[2.2.2]oct-3-yl]-4-(3-chlorophenylsulfanyl)benzamide; N-[(2S,3R)-2-methyl-1-azabicyclo[2.2.2]oct-3-yl]-4-(4-chlorophenylsulfanyl)benzamide; N-[(2S,3R)-2-methyl-1-azabicyclo[2.2.2]oct -3-yl]-4-(2-chlorophenylsulfanyl) benzamide; N-[(2S,3R)-2-methyl-1-azabicyclo[2.2.2]oct-3-yl]-4-(4-methoxyphenylsulfanyl)-benzamide; N-[(2S,3R)-2-methyl-1-azabicyclo[2.2.2]oct-3-yl]-4-(3-methoxyphenylsulfanyl)-benzamide; N-[(2S,3R)-2-methyl-1-azabicyclo[2.2.2]oct-3-yl]-4-(2-methoxyphenylsulfanyl)-benzamide; N-[(2S,3R)-2-methyl-1-azabicyclo[2.2.2]oct-3-yl]-4-phenoxybenzamide; N-[(3R)-1-azabicyclo[2.2.2]oct-3-yl]-4-(4-aminophenoxy)-benzamide; N-[(3R)-1-azabicyclo[2.2.2]oct-3-yl]-4-(3-aminophenoxy)-benzamide; N-[(3R)-1-azabicyclo[2.2.2]oct-3-yl]-4-(2-aminophenoxy)-benzamide; N-[(3R)-1-azabicyclo[2.2.2]oct-3-yl]-4-(4-methanesulfonylamino-phenoxy)-benzamide; N-[(3R)-1-azabicyclo[2.2.2]oct-3-yl]-4-(3-methanesulfonylamino-phenoxy)-benzamide; N-[(3R)-1-azabicyclo[2.2.2]oct-3-yl]-4-(2-methanesulfonylamino-phenoxy)-benzamide; N-[(3R)-1-azabicyclo[2.2.2]oct-3-yl]-4-(4-acetoxyphenoxy)-benzamide; N-[(3R)-1-azabicyclo[2.2.2]oct-3-yl]-4-(3-acetoxyphenoxy)-benzamide; N-[(3R)-1-azabicyclo[2.2.2]oct-3-yl]-4-(2-acetoxyphenoxy)-benzamide; N-[(3R)-1-azabicyclo[2.2.2]oct-3-yl]-4-(4-acetylphenoxy)-benzamide; N-[(3R)-1-azabicyclo[2.2.2]oct-3-yl]-4-(3-acetylphenoxy)-benzamide; N-[(3R)-1-azabicyclo[2.2.2]oct-3-yl]-4-(2-acetylphenoxy)-benzamide; N-[(3R)-1-azabicyclo[2.2.2]oct-3-yl]-4-(4-carbamoylphenoxy)-benzamide; N-[(3R)-1-azabicyclo[2.2.2]oct-3-yl]-4-(4-carbamoylphenoxy)-benzamide; N-[(3R)-1-azabicyclo[2.2.2]oct-3-yl]-4-(3-carbamoylphenoxy)-benzamide; N-[(3R)-1-azabicyclo[2.2.2]oct-3-yl]-4-(2-carbamoylphenoxy)-benzamide; N-[(3R)-1-azabicyclo[2.2.2]oct-3-yl]-4-(4-cyanophenoxy)-benzamide; N-[(3R)-1-azabicyclo[2.2.2]oct-3-yl]-4-(3-cyanophenoxy)-benzamide; N-[(3R)-1-azabicyclo[2.2.2]oct-3-yl]-4-(2-cyanophenoxy)-benzamide; N-[(3R)-1-azabicyclo[2.2.2]oct-3-yl]-4-(4-sulfamoylphenoxy)-benzamide; N-[(3R)-1-azabicyclo[2.2.2]oct-3-yl]-4-(3-sulfamoylphenoxy)-benzamide; N-[(3R)-1-azabicyclo[2.2.2]oct-3-yl]-4-(2-sulfamoylphenoxy)-benzamide; N-[(3R)-1-azabicyclo[2.2.2]oct-3-yl]-4-(thiophen-2-yloxy)-benzamide; N-[(3R)-1-azabicyclo[2.2.2]oct-3-yl]-4-(5-methylthiophen-2-yloxy)-benzamide; N-[(3R)-1-azabicyclo[2.2.2]oct-3-yl]-4-(5-chlorothiophen-2-yloxy)-benzamide; N-[(3R)-1-azabicyclo[2.2.2]oct-3-yl]-4-(5-methoxythiophen-2-yloxy)-benzamide; N-[(3R)-1-azabicyclo[2.2.2]oct-3-yl]-4-(5-trifluoromethylthiophen-2-yloxy)-benzamide; N-[(3R)-1-azabicyclo[2.2.2]oct-3-yl]-4-(5-acetylthiophen-2-yloxy)-benzamide; N-[(3R)-1-azabicyclo[2.2.2]oct-3-yl]-4-(5-acetaminothiophen-2-yloxy)-benzamide; N-[(3R)-1-azabicyclo[2.2.2]oct-3-yl]-4-(5-cyanothiophen-2-yloxy)-benzamide; N-[(3R)-1-azabicyclo[2.2.2]oct-3-yl]-4-(5-morpholin-4-yl-thiophen-2-yloxy)-benzamide; N-[(3R)-1-azabicyclo[2.2.2]oct-3-yl]-4-(4-methylthiophen-2-yloxy)-benzamide; N-[(3R)-1-azabicyclo[2.2.2]oct-3-yl]-4-(4-chlorothiophen-2-yloxy)-benzamide; N-[(3R)-1-azabicyclo[2.2.2]oct-3-yl]-4-(4-methoxythiophen-2-yloxy)-benzamide; N-[(3R)-1-azabicyclo[2.2.2]oct-3-yl]-4-(4-trifluoromethylthiophen-2-yloxy)-benzamide; N-[(3R)-1-azabicyclo[2.2.2]oct-3-yl]-4-(4-acetylthiophen-2-yloxy)-benzamide; N-[(3R)-1-azabicyclo[2.2.2]oct-3-yl]-4-(4-acetaminothiophen-2-yloxy)-benzamide; N-[(3R)-1-azabicyclo[2.2.2]oct-3-yl]-4-(4-cyanothiophen-2-yloxy)-benzamide; N-[(3R)-1-azabicyclo[2.2.2]oct-3-yl]-4-(4-morpholin-4-yl-thiophen-2-yloxy)-benzamide; N-[(3R)-1-azabicyclo[2.2.2]oct-3-yl]-4-(furan-2-yloxy)-benzamide; N-[(3R)-1-azabicyclo[2.2.2]oct-3-yl]-4-(5-methylfuran-2-yloxy)-benzamide; N-[(3R)-1-azabicyclo[2.2.2]oct-3-yl]-4-(5-chlorofuran-2-yloxy)-benzamide; N-[(3R)-1-azabicyclo[2.2.2]oct-3-yl]-4-(5-methoxyfuran-2-yloxy)-benzamide; N-[(3R)-1-azabicyclo[2.2.2]oct-3-yl]-4-(5-trifluoromethylfuran-2-yloxy)-benzamide; N-[(3R)-1-azabicyclo[2.2.2]oct-3-yl]-4-(5-acetylfuran-2-yloxy)-benzamide; N-[(3R)-1-azabicyclo[2.2.2]oct-3-yl]-4-(5-acetaminofuran-2-yloxy)-benzamide; N-[(3R)-1-azabicyclo[2.2.2]oct-3-yl]-4-(5-cyanofuran-2-yloxy)-benzamide; N-[(3R)-1-azabicyclo[2.2.2]oct-3-yl]-4-(5-morpholin-4-yl-furan-2-yloxy)-benzamide; N-[(3R)-1-azabicyclo[2.2.2]oct-3-yl]-4-(4-methylfuran-2-yloxy)-benzamide; N-[(3R)-1-azabicyclo[2.2.2]oct-3-yl]-4-(4-chlorofuran-2-yloxy)-benzamide; N-[(3R)-1-azabicyclo[2.2.2]oct-3-yl]-4-(4-methoxyfuran-2-yloxy)-benzamide; N-[(3R)-1-azabicyclo[2.2.2]oct-3-yl]-4-(4-trifluoromethylfuran-2-yloxy)-benzamide; N-[(3R)-1-azabicyclo[2.2.2]oct-3-yl]-4-(4-acetylfuran-2-yloxy)-benzamide; N-[(3R)-1-azabicyclo[2.2.2]oct-3-yl]-4-(4-acetaminofuran-2-yloxy)-benzamide; N-[(3R)-1-azabicyclo[2.2.2]oct-3-yl]-4-(4-cyanofuran-2-yloxy)-benzamide; N-[(3R)-1-azabicyclo[2.2.2]oct-3-yl]-4-(4-morpholin-4-yl-furan-2-yloxy)-benzamide; N-[(3R)-1-azabicyclo[2.2.2]oct-3-yl]-4-(oxazol-2-yloxy)-benzamide; N-[(3R)-1-azabicyclo[2.2.2]oct-3-yl]-4-(5-methyloxazol-2-yloxy)-benzamide; N-[(3R)-1-azabicyclo[2.2.2]oct-3-yl]-4-(5-chlorooxazol-2-yloxy)-benzamide; N-[(3R)-1-azabicyclo[2.2.2]oct-3-yl]-4-(5-methoxyoxazol-2-yloxy)-benzamide; N-[(3R)-1-azabicyclo[2.2.2]oct-3-yl]-4-(5-trifluoromethyloxazol-2-yloxy)-benzamide; N-[(3R)-1-azabicyclo[2.2.2]oct-3-yl]-4-(5-acetyloxazol-2-yloxy)-benzamide; N-[(3R)-1-azabicyclo[2.2.2]oct-3-yl]-4-(5-acetaminooxazol-2-yloxy)-benzamide; N-[(3R)-1-azabicyclo[2.2.2]oct-3-yl]-4-(5-cyanooxazol-2-yloxy)-benzamide; N-[(3R)-1-azabicyclo[2.2.2]oct-3-yl]-4-(5-morpholin-4-yl-oxazol-2-yloxy)-benzamide; N-[(3R)-1-azabicyclo[2.2.2]oct-3-yl]-4-(oxazol-2-yloxy)-benzamide; N-[(3R)-1-azabicyclo[2.2.2]oct-3-yl]-4-(4-methyloxazol-2-yloxy)-benzamide; N-[(3R)-1-azabicyclo[2.2.2]oct-3-yl]-4-(4-chlorooxazo-2-yloxy)-benzamide; N-[(3R)-1-azabicyclo[2.2.2]oct-3-yl]-4-(4-methoxyoxazol-2-yloxy)-benzamide; N-[(3R)-1-azabicyclo[2.2.2]oct-3-yl]-4-(4-trifluoromethyloxazol-2-yloxy)-benzamide; N-[(3R)-1-azabicyclo[2.2.2]oct-3-yl]-4-(4-acetyloxazol-2-yloxy)-benzamide; N-[(3R)-1-azabicyclo[2.2.2]oct-3-yl]-4-(4-acetaminooxazol-2-yloxy)-benzamide; N-[(3R)-1-azabicyclo[2.2.2]oct-3-yl]-4-(4-cyanooxazol-2-yloxy)-benzamide; N-[(3R)-1-azabicyclo[2.2.2]oct-3-yl]-4-(4-morpholin-4-yl-oxazol-2-yloxy)-benzamide; N-[(3R)-1-azabicyclo[2.2.2]oct-3-yl]-4-(oxazol-5-yloxy)-benzamide; N-[(3R)-1-azabicyclo[2.2.2]oct-3-yl]-4-(2-methyloxazol-5-yloxy)-benzamide; N-[(3R)-1-azabicyclo[2.2.2]oct-3-yl]-4-(2-chlorooxazol-5-yloxy)-benzamide; N-[(3R)-1-azabicyclo[2.2.2]oct-3-yl]-4-(2-methoxyoxazol-5-yloxy)-benzamide; N-[(3R)-1- azabicyclo[2.2.2]oct-3-yl]-4-(2-trifluoromethyloxazol-5-yloxy)-benzamide; N-[(3R)-1-azabicyclo[2.2.2]oct-3-yl]-4-(2-acetyloxazol-5-yloxy)-benzamide; N-[(3R)-1-azabicyclo[2.2.2]oct-3-yl]-4-(2-acetaminooxazol-5-yloxy)-benzamide; N-[(3R)-1-azabicyclo[2.2.2]oct-3-yl]-4-(2-cyanooxazol-5-yloxy)-benzamide; N-[(3R)-1-azabicyclo[2.2.2]oct-3-yl]-4-(2-morpholin-4-yl-oxazol-5-yloxy)-benzamide; N-[(3R)-1-azabicyclo[2.2.2]oct-3-yl]-4-(thiazol-2-yloxy)-benzamide; N-[(3R)-1-azabicyclo[2.2.2]oct-3-yl]-4-(5-methylthiazol-2-yloxy)-benzamide; N-[(3R)-1-azabicyclo[2.2.2]oct-3-yl]-4-(5-chlorothiazol-2-yloxy)-benzamide; N-[(3R)-1-azabicyclo[2.2.2]oct-3-yl]-4-(5-methoxythiazol-2-yloxy)-benzamide; N-[(3R)-1-azabicyclo[2.2.2]oct-3-yl]-4-(5-trifluoromethylthiazol-2-yloxy)-benzamide; N-[(3R)-1-azabicyclo[2.2.2]oct-3-yl]-4-(5-acetylthiazol-2-yloxy)-benzamide; N-[(3R)-1-azabicyclo[2.2.2]oct-3-yl]-4-(5-acetaminothiazol-2-yloxy)-benzamide; N-[(3R)-1-azabicyclo[2.2.2]oct-3-yl]-4-(5-cyanothiazol-2-yloxy)-benzamide; N-[(3R)-1-azabicyclo[2.2.2]oct-3-yl]-4-(5-morpholin-4-yl-thiazol-2-yloxy)-benzamide; N-[(3R)-1-azabicyclo[2.2.2]oct-3-yl]-4-(thiazol-2-yloxy)-benzamide; N-[(3R)-1-azabicyclo[2.2.2]oct-3-yl]-4-(4-methylthiazol-2-yloxy)-benzamide; N-[(3R)-1-azabicyclo[2.2.2]oct-3-yl]-4-(4-chlorothiazol-2-yloxy)-benzamide; N-[(3R)-1-azabicyclo[2.2.2]oct-3-yl]-4-(4-methoxythiazol-2-yloxy)-benzamide; N-[(3R)-1-azabicyclo[2.2.2]oct-3-yl]-4-(4-trifluoromethylthiazol-2-yloxy)-benzamide; N-[(3R)-1-azabicyclo[2.2.2]oct-3-yl]-4-(4-acetylthiazol-2-yloxy)-benzamide; N-[(3R)-1-azabicyclo[2.2.2]oct-3-yl]-4-(4-acetaminothiazol-2-yloxy)-benzamide; N-[(3R)-1-azabicyclo[2.2.2]oct-3-yl]-4-(4-cyanothiazol-2-yloxy)-benzamide; N-[(3R)-1-azabicyclo[2.2.2]oct-3-yl]-4-(4-morpholin-4-yl-thiazol-2-yloxy)-benzamide; N-[(3R)-1-azabicyclo[2.2.2]oct-3-yl]-4-(thiazol-5-yloxy)-benzamide; N-[(3R)-1-azabicyclo[2.2.2]oct-3-yl]-4-(2-methylthiazol-5-yloxy)-benzamide; N-[(3R)-1-azabicyclo[2.2.2]oct-3-yl]-4-(2-chlorothiazol-5-yloxy)-benzamide; N-[(3R)-1-azabicyclo[2.2.2]oct-3-yl]-4-(2-methoxythiazol-5-yloxy)-benzamide; N-[(3R)-1-azabicyclo[2.2.2]oct-3-yl]-4-(2-trifluoromethylthiazol-5-yloxy)-benzamide; N-[(3R)-1-azabicyclo[2.2.2]oct-3-yl]-4-(2-acetylthiazol-5-yloxy)-benzamide; N-[(3R)-1-azabicyclo[2.2.2]oct-3-yl]-4-(2-acetaminothiazol-5-yloxy)-benzamide; N-[(3R)-1-azabicyclo[2.2.2]oct-3-yl]-4-(2-cyanothiazol-5-yloxy)-benzamide; N-[(3R)-1-azabicyclo[2.2.2]oct-3-yl]-4-(2-morpholin-4-yl-thiazol-5-yloxy)-benzamide; N-[(3R)-1-azabicyclo[2.2.2]oct-3-yl]-4-([1,3,4]oxadiazol-2-yloxy)-benzamide; N-[(3R)-1-azabicyclo[2.2.2]oct-3-yl]-4-(5-methyl[1,3,4]oxadiazol-2-yloxy)-benzamide; N-[(3R)-1-azabicyclo[2.2.2]oct-3-yl]-4-(5-chloro[1,3,4]oxadiazol-2-yloxy)-benzamide; N-[(3R)-1-azabicyclo[2.2.2]oct-3-yl]-4-(5-methoxy[1,3,4]oxadiazol-2-yloxy)-benzamide; N-[(3R)-1-azabicyclo[2.2.2]oct-3-yl]-4-(5-trifluoromethyl[1,3,4]oxadiazol-2-yloxy)-benzamide; N-[(3R)-1-azabicyclo[2.2.2]oct-3-yl]-4-(5-acetyl[1,3,4]oxadiazol-2-yloxy)-benzamide; N-[(3R)-1-azabicyclo[2.2.2]oct-3-yl]-4-(5-acetamino[1,3,4]oxadiazol-2-yloxy)-benzamide; N-[(3R)-1-azabicyclo[2.2.2]oct-3-yl]-4-(5-cyano[1,3,4]oxadiazol-2-yloxy)-benzamide; N-[(3R)-1-azabicyclo[2.2.2]oct-3-yl]-4-(5-morpholin-4-yl-[1,3,4]oxadiazol-2-yloxy)-benzamide; N-[(3R) 1-azabicyclo[2.2.2]oct-3-yl]-4-([1,3,4]thiadiazol-2-yloxy)-benzamide; N-[(3R)-1-azabicyclo[2.2.2]oct-3-yl]-4-(5-methyl[1,3,4]thiadiazol-2-yloxy)-benzamide; N-[(3R)-1-azabicyclo[2.2.2]oct-3-yl]-4-(5-chloro[1,3,4]thiadiazol-2-yloxy)-benzamide; N-[(3R)-1-azabicyclo[2.2.2]oct-3-yl]-4-(5-methoxy[1,3,4]thiadiazol-2-yloxy)-benzamide; N-[(3R)-1-azabicyclo[2.2.2]oct-3-yl]-4-(5-trifluoromethyl[1,3,4]thiadiazol-2-yloxy)-benzamide; N-[(3R)-1-azabicyclo[2.2.2]oct-3-yl]-4-(5-acetyl[1,3,4]thiadiazol-2-yloxy)-benzamide; N-[(3R)-1-azabicyclo[2.2.2]oct-3-yl]-4-(5-acetamino[1,3,4]thiadiazol-2-yloxy)-benzamide; N-[(3R)-1-azabicyclo[2.2.2]oct-3-yl]-4-(5-cyano[1,3,4]thiadiazol-2-yloxy)-benzamide; N-[(3R)-1-azabicyclo[2.2.2]oct-3-yl]-4-(5-morpholin-4-yl-[1,3,4]thiadiazol-2-yloxy)-benzamide; N-[(3R)-1-azabicyclo[2.2.2]oct-3-yl]-4-(4-aminophenylsulfanyl)-benzamide; N-[(3R)-1-azabicyclo[2.2.2]oct-3-yl]-4-(3-aminophenylsulfanyl)-benzamide; N-[(3R)-1-azabicyclo[2.2.2]oct-3-yl]-4-(2-aminophenylsulfanyl)-benzamide; N-[(3R)-1-azabicyclo[2.2.2]oct-3-yl]-4-(4-methanesulfonylamino-phenylsulfanyl)-benzamide; N-[(3R)-1-azabicyclo[2.2.2]oct-3-yl]-4-(3-methanesulfonylamino-phenylsulfanyl)-benzamide; N-[(3R)-1-azabicyclo[2.2.2]oct-3-yl]-4-(2-methanesulfonylamino-phenylsulfanyl)-benzamide; N-[(3R)-1-azabicyclo[2.2.2]oct-3-yl]-4-(4-acetoxyphenylsulfanyl)-benzamide; N-[(3R)-1-azabicyclo[2.2.2]oct-3-yl]-4-(3-acetoxyphenylsulfanyl)-benzamide; N-[(3R)-1-azabicyclo[2.2.2]oct-3-yl]-4-(2-acetoxyphenylsulfanyl)-benzamide; N-[(3R)-1-azabicyclo[2.2.2]oct-3-yl]-4-(4-acetylphenylsulfanyl)-benzamide; N-[(3R)-1-azabicyclo[2.2.2]oct-3-yl]-4-(3-acetylphenylsulfanyl)-benzamide; N-[(3R)-1-azabicyclo[2.2.2]oct-3-yl]-4-(2-acetylphenylsulfanyl)-benzamide; N-[(3R)-1-azabicyclo[2.2.2]oct-3-yl]-4-(4-carbamoylphenylsulfanyl)-benzamide; N-[(3R)-1-azabicyclo[2.2.2]oct-3-yl]-4-(3-carbamoylphenylsulfanyl)-benzamide; N-[(3R)-1-azabicyclo[2.2.2]oct-3-yl]-4-(2-carbamoylphenylsulfanyl)-benzamide; N-[(3R)-1-azabicyclo[2.2.2]oct-3-yl]-4-(4-cyanophenylsulfanyl)-benzamide; N-[(3R)-1-azabicyclo[2.2.2]oct-3-yl]-4-(3-cyanophenylsulfanyl)-benzamide; N-[(3R)-1-azabicyclo[2.2.2]oct-3-yl]-4-(2-cyanophenylsulfanyl)-benzamide; N-[(3R)-1-azabicyclo[2.2.2]oct-3-yl]-4-(4-sulfamoylphenylsulfanyl)-benzamide; N-[(3R)-1-azabicyclo[2.2.2]oct-3-yl]-4-(3-sulfamoylphenylsulfanyl)-benzamide; N-[(3R)-1-azabicyclo[2.2.2]oct-3-yl]-4-(2-sulfamoylphenylsulfanyl)-benzamide; N-[(3R)-1-azabicyclo[2.2.2]oct-3-yl]-4-(4-hydroxyphenylsulfanyl)-benzamide; N-[(3R)-1-azabicyclo[2.2.2]oct-3-yl]-4-(3-hydroxyphenylsulfanyl)-benzamide; N-[(3R)-1-azabicyclo[2.2.2]oct-3-yl]-4-(2-hydroxyphenylsulfanyl)-benzamide; N-[(3R)-1-azabicyclo[2.2.2]oct-3-yl]-4-(4-acetamidophenylsulfanyl)-benzamide; N-[(3R)-1-azabicyclo[2.2.2]oct-3-yl]-4-(3-acetamidophenylsulfanyl)-benzamide; N-[(3R)-1-azabicyclo[2.2.2]oct-3-yl]-4-(2-acetamidophenylsulfanyl)-benzamide; N-[(3R)-1-azabicyclo[2.2.2]oct-3-yl]-4-(thiophen-2-ylsulfanyl)-benzamide; N-[(3R)-1-azabicyclo[2.2.2]oct-3-yl]-4-(5-methylthiophen-2-ylsulfanyl)-benzamide; N-[(3R)-1-azabicyclo[2.2.2]oct-3-yl]-4-(5-chlorothiophen-2-ylsulfanyl)-benzamide; N-[(3R)-1-azabicyclo[2.2.2]oct-3-yl]-4-(5-methoxythiophen-2-ylsulfanyl)-benzamide; N-[(3R)-1-azabicyclo[2.2.2]oct-3-yl]-4-(5-trifluoromethylthiophen-2-ylsulfanyl)-benzamide; N-[(3R)-1-azabicyclo[2.2.2]oct-3-yl]-4-(5-acetylthiophen-2-ylsulfanyl)-benzamide; N-[(3R)-1-azabicyclo[2.2.2]oct-3-yl]-4-(5-acetaminothiophen-2-ylsulfanyl)-benzamide; N-[(3R)-1-azabicyclo[2.2.2]oct-3-yl]-4-(5-cyanothiophen-2-ylsulfanyl)-benzamide;

N-[(3R)-1-azabicyclo[2.2.2]oct-3-yl]-4-(5-morpholin-4-yl-thiophen-2-ylsulfanyl)-benzamide; N-[(3R)-1-azabicyclo[2.2.2]oct-3-yl]-4-(4-methylthiophen-2-ylsulfanyl)-benzamide; N-[(3R)-1-azabicyclo[2.2.2]oct-3-yl]-4-(4-chlorothiophen-2-ylsulfanyl)-benzamide; N-[(3R)-1-azabicyclo[2.2.2]oct-3-yl]-4-(4-methoxythiophen-2-ylsulfanyl)-benzamide; N-[(3R)-1-azabicyclo[2.2.2]oct-3-yl]-4-(4-trifluoromethylthiophen-2-ylsulfanyl)-benzamide; N-[(3R)-1-azabicyclo[2.2.2]oct-3-yl]-4-(4-acetylthiophen-2-ylsulfanyl)-benzamide; N-[(3R)-1-azabicyclo[2.2.2]oct-3-yl]-4-(4-acetaminothiophen-2-ylsulfanyl)-benzamide; N-[(3R)-1-azabicyclo[2.2.2]oct-3-yl]-4-(4-cyanothiophen-2-ylsulfanyl)-benzamide; N-[(3R)-1-azabicyclo[2.2.2]oct-3-yl]-4-(4-morpholin-4-yl-thiophen-2-ylsulfanyl)-benzamide; N-[(3R)-1-azabicyclo[2.2.2]oct-3-yl]-4-(furan-2-ylsulfanyl)-benzamide; N-[(3R)-1-azabicyclo[2.2.2]oct-3-yl]-4-(5-methylfuran-2-ylsulfanyl)-benzamide; N-[(3R)-1-azabicyclo[2.2.2]oct-3-yl]-4-(5-chlorofuran-2-ylsulfanyl)-benzamide; N-[(3R)-1-azabicyclo[2.2.2]oct-3-yl]-4-(5-methoxyfuran-2-ylsulfanyl)-benzamide; N-[(3R)-1-azabicyclo[2.2.2]oct-3-yl]-4-(5-trifluoromethylfuran-2-ylsulfanyl)-benzamide; N-[(3R)-1-azabicyclo[2.2.2]oct-3-yl]-4-(5-acetylfuran-2-ylsulfanyl)-benzamide; N-[(3R)-1-azabicyclo[2.2.2]oct-3-yl]-4-(5-acetaminofuran-2-ylsulfanyl)-benzamide; N-[(3R)-1-azabicyclo[2.2.2]oct-3-yl]-4-(5-cyanofuran-2-ylsulfanyl)-benzamide; N-[(3R)-1-azabicyclo[2.2.2]oct-3-yl]-4-(5-morpholin-4-yl-furan-2-ylsulfanyl)-benzamide; N-[(3R)-1-azabicyclo[2.2.2]oct-3-yl]-4-(4-methylfuran-2-ylsulfanyl)-benzamide; N-[(3R)-1-azabicyclo[2.2.2]oct-3-yl]-4-(4-chlorofuran-2-ylsulfanyl)-benzamide; N-[(3R)-1-azabicyclo[2.2.2]oct-3-yl]-4-(4-methoxyfuran-2-ylsulfanyl)-benzamide; N-[(3R)-1-azabicyclo[2.2.2]oct-3-yl]-4-(4-trifluoromethylfuran-2-ylsulfanyl)-benzamide; N-[(3R)-1-azabicyclo[2.2.2]oct-3-yl]-4-(4-acetylfuran-2-ylsulfanyl)-benzamide; N-[(3R)-1-azabicyclo[2.2.2]oct-3-yl]-4-(4-acetaminofuran-2-ylsulfanyl)-benzamide; N-[(3R)-1-azabicyclo[2.2.2]oct-3-yl]-4-(4-cyanofuran-2-ylsulfanyl)-benzamide; N-[(3R)-1-azabicyclo[2.2.2]oct-3-yl]-4-(4-morpholin-4-yl-furan-2-ylsulfanyl)-benzamide; N-[(3R)-1-azabicyclo[2.2.2]oct-3-yl]-4-(oxazol-2-ylsulfanyl)-benzamide; N-[(3R)-1-azabicyclo[2.2.2]oct-3-yl]-4-(5-methyloxazol-2-ylsulfanyl)-benzamide; N-[(3R)-1-azabicyclo[2.2.2]oct-3-yl]-4-(5-chlorooxazol-2-ylsulfanyl)-benzamide; N-[(3R)-1-azabicyclo[2.2.2]oct-3-yl]-4-(5-methoxyoxazol-2-ylsulfanyl)-benzamide; N-[(3R)-1-azabicyclo[2.2.2]oct-3-yl]-4-(5-trifluoromethyloxazol-2-ylsulfanyl)-benzamide; N-[(3R)-1-azabicyclo[2.2.2]oct-3-yl]-4-(5-acetyloxazol-2-ylsulfanyl)-benzamide; N-[(3R)-1-azabicyclo[2.2.2]oct-3-yl]-4-(5-acetaminooxazol-2-ylsulfanyl)-benzamide; N-[(3R)-1-azabicyclo[2.2.2]oct-3-yl]-4-(5-cyanooxazol-2-ylsulfanyl)-benzamide; N-[(3R)-1-azabicyclo[2.2.2]oct-3-yl]-4-(5-morpholin-4-yl-oxazol-2-ylsulfanyl)-benzamide; N-[(3R)-1-azabicyclo[2.2.2]oct-3-yl]-4-(oxazol-2-ylsulfanyl)-benzamide; N-[(3R)-N-1-azabicyclo[2.2.2]oct-3-yl]-4-methyloxazol-2-ylsulfanyl)-benzamide; N-[(3R)-1-azabicyclo[2.2.2]oct-3-yl]-4-(4-chlorooxazol-2-ylsulfanyl)-benzamide; N-[(3R)-1-azabicyclo[2.2.2]oct-3-yl]-4-(4-methoxyoxazol-2-ylsulfanyl)-benzamide; N-[(3R)-1-azabicyclo[2.2.2]oct-3-yl]-4-(4-trifluoromethyloxazol-2-ylsulfanyl)-benzamide; N-[(3R)-1-azabicyclo[2.2.2]oct-3-yl]-4-(4-acetyloxazol-2-ylsulfanyl)-benzamide; N-[(3R)-1-azabicyclo[2.2.2]oct-3-yl]-4-(4-acetaminooxazol-2-ylsulfanyl)-benzamide; N-[(3R)-1-azabicyclo[2.2.2]oct-3-yl]-4-(4-cyanooxazol-2-ylsulfanyl)-benzamide; N-[(3R)-1-azabicyclo[2.2.2]oct-3-yl]-4-(4-morpholin-4-yl-oxazol-2-ylsulfanyl)-benzamide; N-[(3R)-1-azabicyclo[2.2.2]oct-3-yl]-4-(oxazol-5-ylsulfanyl)-benzamide; N-[(3R)-1-azabicyclo[2.2.2]oct-3-yl]-4-(2-methyloxazol-5-ylsulfanyl)-benzamide; N-[(3R)-1-azabicyclo[2.2.2]oct-3-yl]-4-(2-chlorooxazol-5-ylsulfanyl)-benzamide; N-[(3R)-1-azabicyclo[2.2.2]oct-3-yl]-4-(2-methoxyoxazol-5-ylsulfanyl)-benzamide; N-[(3R)-1-azabicyclo[2.2.2]oct-3-yl]-4-(2-trifluoromethyloxazol-5-ylsulfanyl)-benzamide; N-[(3R)-1-azabicyclo[2.2.2]oct-3-yl]-4-(2-acetyloxazol-5-ylsulfanyl)-benzamide; N-[(3R)-1-azabicyclo[2.2.2]oct-3-yl]-4-(2-acetaminooxazol-5-ylsulfanyl)-benzamide; N-[(3R)-1-azabicyclo[2.2.2]oct-3-yl]-4-(2-cyanooxazol-5-ylsulfanyl)-benzamide; N-[(3R)-1-azabicyclo[2.2.2]oct-3-yl]-4-(2-morpholin-4-yl-oxazol-5-ylsulfanyl)-benzamide; N-[(3R)-1-azabicyclo[2.2.2]oct-3-yl]-4-(thiazol-2-ylsulfanyl)-benzamide; N-[(3R)-1-azabicyclo[2.2.2]oct-3-yl]-4-(5-methylthiazol-2-ylsulfanyl)-benzamide; N-[(3R)-1-azabicyclo[2.2.2]oct-3-yl]-4-(5-chlorothiazol-2-ylsulfanyl)-benzamide; N-[(3R)-1-azabicyclo[2.2.2]oct-3-yl]-4-(5-methoxythiazol-2-ylsulfanyl)-benzamide; N-[(3R)-1-azabicyclo[2.2.2]oct-3-yl]-4-(5-trifluoromethylthiazol-2-ylsulfanyl)-benzamide; N-[(3R)-1-azabicyclo[2.2.2]oct-3-yl]-4-(5-acetylthiazol-2-ylsulfanyl)-benzamide; N-[(3R)-1-azabicyclo[2.2.2]oct-3-yl]-4-(5-acetaminothiazol-2-ylsulfanyl)-benzamide; N-[(3R)-1-azabicyclo[2.2.2]oct-3-yl]-4-(5-cyanothiazol-2-ylsulfanyl)-benzamide; N-[(3R)-1-azabicyclo[2.2.2]oct-3-yl]-4-(5-morpholin-4-yl-thiazol-2-ylsulfanyl)-benzamide; N-[(3R)-1-azabicyo[2.2.2]oct-3-yl]-4-(thiazol-2-ylsulfanyl)-benzamide; N-[(3R)-1-azabicyclo[2.2.2]oct-3-yl]-4-(4-methylthiazol-2-ylsulfanyl)-benzamide; N-[(3R)-1-azabicyclo[2.2.2]oct-3-yl]-4-(4-chlorothiazol-2-ylsulfanyl)-benzamide; N-[(3R)-1-azabicyclo[2.2.2]oct-3-yl]-4-(4-methoxythiazol-2-ylsulfanyl)-benzamide; N-[(3R)-1-azabicyclo[2.2.2]oct-3-yl]-4-(4-trifluoromethylthiazol-2-ylsulfanyl)-benzamide; N-[(3R)-1-azabicyclo[2.2.2]oct-3-yl]-4-(4-acetylthiazol-2-ylsulfanyl)-benzamide; N-[(3R)-1-azabicyclo[2.2.2]oct-3-yl]-4-(4-acetaminothiazol-2-ylsulfanyl)-benzamide; N-[(3R)-1-azabicyclo[2.2.2]oct-3-yl]-4-(4-cyanothiazol-2-ylsulfanyl)-benzamide; N-[(3R)-1-azabicyclo[2.2.2]oct-3-yl]-4-(4-morpholin-4-yl-thiazol-2-ylsulfanyl)-benzamide; N-[(3R)-1-azabicyclo[2.2.2]oct-3-yl]-4-(thiazol-5-ylsulfanyl)-benzamide; N-[(3R)-1-azabicyclo[2.2.2]oct-3-yl]-4-(2-methylthiazol-5-ylsulfanyl)-benzamide; N-[(3R)-1-azabicyclo[2.2.2]oct-3-yl]-4-(2-chlorothiazol-5-ylsulfanyl)-benzamide; N-[(3R)-1-azabicyclo[2.2.2]oct-3-yl]-4-(2-methoxythiazol-5-ylsulfanyl)-benzamide; N-[(3R)-1-azabicyclo[2.2.2]oct-3-yl]-4-(2-trifluoromethylthiazol-5-ylsulfanyl)-benzamide; N-[(3R)-1-azabicyclo[2.2.2]oct-3-yl]-4-(2-acetylthiazol-5-ylsulfanyl)-benzamide; N-[(3R)-1-azabicyclo[2.2.2]oct-3-yl]-4-(2-acetaminothiazol-5-ylsulfanyl)-benzamide; N-[(3R)-1-azabicyclo[2.2.2]oct-3-yl]-4-(2-cyanothiazol-5-ylsulfanyl)-benzamide; N-[(3R)-1-azabicyclo[2.2.2]oct-3-yl]-4-(2-morpholin-4-yl-thiazol-5-ylsulfanyl)-benzamide; N-[(3R)-1-azabicyclo[2.2.2]oct-3-yl]-4-([1,3,4]oxadiazol-2-ylsulfanyl)-benzamide; N-[(3R)-1-azabicyclo[2.2.2]oct-3-yl]-4-(5-methyl[1,3,4]oxadiazol-2-ylsulfanyl)-benzamide; N-[(3R)-1-azabicyclo[2.2.2]oct-3-yl]-4-(5-chloro[1,3,4]oxadiazol-2-ylsulfanyl)- benzamide; N-[(3R)-1-azabicyclo[2.2.2]oct-3-yl]-4-(5-methoxy[1,3,4]oxadiazol-2-ylsulfanyl)-benzamide; N-[(3R)-1-azabicyclo[2.2.2]oct-3-yl]-4-(5-trifluoromethyl[1,3,4]oxadiazol-2-ylsulfanyl)-benzamide; N-[(3R)-1-azabicyclo[2.2.2]oct-3-yl]-4-(5-acetyl[1,3,4]oxadiazol-2-ylsulfanyl)-benzamide; N-[(3R)-1-azabicyclo[2.2.2]oct-3-yl]-4-(5-acetamino[1,3,4]oxadiazol-2-ylsulfanyl)-benzamide; N-[(3R)-1-azabicyclo[2.2.2]oct-3-yl]-4-(5-cyano[1,3,4]oxadiazol-2-ylsulfanyl)-benzamide; N-[(3R)-1-azabicyclo[2.2.2]oct-3-yl]-4-(5-morpholin-4-yl-[1,3,4]oxadiazol-2-ylsulfanyl)-benzamide; N-[(3R)-1-azabicyclo[2.2.2]oct-3-yl]-4-([1,3,4]thiadiazol-2-ylsulfanyl)-benzamide; N-[(3R)-1-azabicyclo[2.2.2]oct-3-yl]-4-(5-methyl[1,3,4]thiadiazol-2-ylsulfanyl)-benzamide; N-[(3R)-1-azabicyclo[2.2.2]oct-3-yl]-4-(5-chloro[1,3,4]thiadiazol-2-ylsulfanyl)-benzamide; N-[(3R)-1-azabicyclo[2.2.2]oct-3-yl]-4-(5-methoxy[1,3,4]thiadiazol-2-ylsulfanyl)-benzamide; N-[(3R)-1-azabicyclo[2.2.2]oct-3-yl]-4-(5-trifluoromethyl[1,3,4]thiadiazol-2-ylsulfanyl)-benzamide; N-[(3R)-1-azabicyclo[2.2.2]oct-3-yl]-4-(5-acetyl[1,3,4]thiadiazol-2-ylsulfanyl)-benzamide; N-[(3R)-1-azabicyclo[2.2.2]oct-3-yl]-4-(5-acetamino[1,3,4]thiadiazol-2-ylsulfanyl)-benzamide; N-[(3R)-1-azabicyclo[2.2.2]oct-3-yl]-4-(5-cyano[1,3,4]thiadiazol-2-ylsulfanyl)-benzamide; N-[(3R)-1-azabicyclo[2.2.2]oct-3-yl]-4-(5-morpholin-4-yl-[1,3,4]thiadiazol-2-ylsulfanyl)-benzamide; N-[(3R)-1-azabicyclo[2.2.2]oct-3-yl]-4-(pyrrol-2-yloxy)-benzamide; N-[(3R)-1-azabicyclo[2.2.2]oct-3-yl]-4-(5-methylpyrrol-2-yloxy)-benzamide; N-[(3R)-1-azabicyclo[2.2.2]oct-3-yl]-4-(5-chloropyrrol-2-yloxy)-benzamide; N-[(3R)-1-azabicyclo[2.2.2]oct-3-yl]-4-(5-methoxypyrrol-2-yloxy)-benzamide; N-[(3R)-1-azabicyclo[2.2.2]oct-3-yl]-4-(5-trifluoromethylpyrrol-2-yloxy)-benzamide; N-[(3R)-1-azabicyclo[2.2.2]oct-3-yl]-4-(5-acetylpyrrol-2-yloxy)-benzamide; N-[(3R)-1-azabicyclo[2.2.2]oct-3-yl]-4-(5-acetaminopyrrol-2-yloxy)-benzamide; N-[(3R)-1-azabicyclo[2.2.2]oct-3-yl]-4-(5-cyanopyrrol-2-yloxy)-benzamide; N-[(3R)-1-azabicyclo[2.2.2]oct-3-yl]-4-(5-morpholin-4-yl-pyrrol-2-yloxy)-benzamide; N-[(3R)-1-azabicyclo[2.2.2]oct-3-yl]-4-(3H-imidazol-4-yloxy)-benzamide; N-[(3R)-1-azabicyclo[2.2.2]oct-3-yl]-4-(2-methyl-3H-imidazol-4-yloxy)-benzamide; N-[(3R)-1-azabicyclo[2.2.2]oct-3-yl]-4-(2-chloro-3H-imidazol-4-yloxy)-benzamide; N-[(3R)-1-azabicyclo[2.2.2]oct-3-yl]-4-(2-methoxy-3H-imidazol-4-yloxy)-benzamide; N-[(3R)-1-azabicyclo[2.2.2]oct-3-yl]-4-(2-trifluoromethyl-3H-imidazol-4-yloxy)-benzamide; N-[(3R)-1-azabicyclo[2.2.2]oct-3-yl]-4-(2-acetyl-3H-imidazol4-yloxy)-benzamide; N-[(3R)-1-azabicyclo[2.2.2]oct-3-yl]-4-(2-acetamino-3H-imidazol-4-yloxy)-benzamide; N-[(3R)-1-azabicyclo[2.2.2]oct-3-yl]-4-(2-cyano-3H-imidazol-4-yloxy)-benzamide; N-[(3R)-1-azabicyclo[2.2.2]oct-3-yl]-4-(2-morpholin-4-yl-3H-imidazol-4-yloxy)-benzamide; N-[(3R)-1-azabicyclo[2.2.2]oct-3-yl]-4-(isoxazol-2-yloxy)-benzamide; N-[(3R)-1-azabicyclo[2.2.2]oct-3-yl]-4-(5-methylisoxazol-3-yloxy)-benzamide; N-[(3R)-1-azabicyclo[2.2.2]oct-3-yl]-4-(5-chloroisoxazol-3-yloxy)-benzamide; N-[(3R)-1-azabicyclo[2.2.2]oct-3-yl]-4-(5-methoxyisoxazol-3-yloxy)-benzamide; N-[(3R)-1-azabicyclo[2.2.2]oct-3-yl]-4-(5-trifluoromethylisoxazol-3-yloxy)-benzamide; N-[(3R)-1-azabicyclo[2.2.2]oct-3-yl]-4-(5-acetylisoxazol-3-yloxy)-benzamide; N-[(3R)-1-azabicyclo[2.2.2]oct-3-yl]-4-(5-acetaminoisoxazol-3-yloxy)-benzamide; N-[(3R)-1-azabicyclo[2.2.2]oct-3-yl]-4-(5-cyanoisoxazol-3-yloxy)-benzamide; N-[(3R)-1-azabicyclo[2.2.2]oct-3-yl]-4-(5-morpholin-4-yl-isoxazol-3-yloxy)-benzamide; N-[(3R)-1-azabicyclo[2.2.2]oct-3-yl]-4-(isothiazol-2-yloxy)-benzamide; N-[(3R)-1-azabicyclo[2.2.2]oct-3-yl]-4-(5-methylisothiazol-3-yloxy)-benzamide; N-[(3R)-1-azabicyclo[2.2.2]oct-3-yl]-4-(5-chloroisothiazol-3-yloxy)-benzamide; N-[(3R)-1-azabicyclo[2.2.2]oct-3-yl]-4-(5-methoxyisothiazol-3-yloxy)-benzamide; N-[(3R)-1-azabicyclo[2.2.2]oct-3-yl]-4-(5-trifluoromethylisothiazol-3-yloxy)-benzamide; N-[(3R)-1-azabicyclo[2.2.2]oct-3-yl]-4-(5-acetylisothiazol-3-yloxy)-benzamide; N-[(3R)-1-azabicyclo[2.2.2]oct-3-yl]-4-(5-acetaminoisothiazol-3-yloxy)-benzamide; N-[(3R)-1-azabicyclo[2.2.2]oct-3-yl]-4-(5-cyanoisothiazol-3-yloxy)-benzamide; N-[(3R)-1-azabicyclo[2.2.2]oct-3-yl]-4-(5-morpholin-4-yl-isothiazol-3-yloxy)-benzamide; N-[(3R)-1-azabicyclo[2.2.2]oct-3-yl]-4-(pyrrol-2-ylsulfanyl)-benzamide; N-[(3R)-1-azabicyclo[2.2.2]oct-3-yl]-4-(5-methylpyrrol-2-ylsulfanyl)-benzamide; N-[(3R)-1-azabicyclo[2.2.2]oct-3-yl]-4-(5-chloropyrrol-2-ylsulfanyl)-benzamide; N-[(3R)-1-azabicyclo[2.2.2]oct-3-yl]-4-(5-methoxypyrrol-2-ylsulfanyl)-benzamide; N-[(3R)-1-azabicyclo[2.2.2]oct-3-yl]-4(5-trifluoromethylpyrrol-2-ylsulfanyl)-benzamide; N-[(3R)-1-azabicyclo[2.2.2]oct-3-yl]-4-(5-acetylpyrrol-2-ylsulfanyl)-benzamide; N-[(3R)-1-azabicyclo[2.2.2]oct-3-yl]-4-(5-acetaminopyrrol-2-ylsulfanyl)-benzamide; N-[(3R)-1-azabicyclo[2.2.2]oct-3-yl]-4-(5-cyanopyrrol-2-ylsulfanyl)-benzamide; N-[(3R)-1-azabicyclo[2.2.2]oct-3-yl]-4-(5-morpholin-4-yl-pyrrol-2-ylsulfanyl)-benzamide; N-[(3R)-1-azabicyclo[2.2.2]oct-3-yl]-4-(3H-imidazol-4-ylsulfanyl)-benzamide; N-[(3R)-1-azabicyclo[2.2.2]oct-3-yl]-4-(2-methyl-3H-imidazol-4-ylsulfanyl)-benzamide; N-[(3R)-1-azabicyclo[2.2.2]oct-3-yl]-4-(2-chloro-3H-imidazol-4-ylsulfanyl)-benzamide; N-[(3R)-1-azabicyclo[2.2.2]oct-3-yl]-4-(2-methoxy-3H-imidazol-4-ylsulfanyl)-benzamide; N-[(3R)-1-azabicyclo[2.2.2]oct-3-yl]-4-(2-trifluoromethyl-3H-imidazol-4-ylsulfanyl)-benzamid; N-[(3R)-1-azabicyclo[2.2.2]oct-3-yl]-4-(2-acetyl-3H-imidazol-4-ylsulfanyl)-benzamide; N-[(3R)-1-azabicyclo[2.2.2]oct-3-yl]-4-(2-acetamino-3H-imidazol-4-ylsulfanyl)-benzamide; N-[(3R)-1-azabicyclo[2.2.2]oct-3-yl]-4-(2-cyano-3H-imidazol-4-ylsulfanyl)-benzamide; N-[(3R)-1-azabicyclo[2.2.2]oct-3-yl]-4-(2-morpholin-4-yl-3H-imidazol-4-ylsulfanyl)-benzamide; N-[(3R)-1-azabicyclo[2.2.2]oct-3-yl]-4-(isoxazol-2-ylsulfanyl))-benzamide; N-[(3R)-1-azabicyclo[2.2.2]oct-3-yl]-4-(5-methylisoxazol-3-ylsulfanyl)-benzamide; N-[(3R)-1-azabicyclo[2.2.2]oct-3-yl]-4-(5-chloroisoxazol-3-ylsulfanyl)-benzamide; N-[(3R)-1-azabicyclo[2.2.2]oct-3-yl]-4-(5-methoxyisoxazol-3-ylsulfanyl)-benzamide; N-[(3R)-1-azabicyclo[2.2.2]oct-3-yl]-4-(5-trifluoromethylisoxazol-3-ylsulfanyl)-benzamide; N-[(3R)-1-azabicyclo[2.2.2]oct-3-yl]-4-(5-acetylisoxazol-3-ylsulfanyl)-benzamide; N-[(3R)-1-azabicyclo[2.2.2]oct-3-yl]-4-(5-acetaminoisoxazol-3-ylsulfanyl)-benzamide; N-[(3R)-1-azabicyclo[2.2.2]oct-3-yl]-4-(5-cyanoisoxazol-3-ylsulfanyl)-benzamide; N-[(3R)-1-azabicyclo[2.2.2]oct-3-yl]-4-(5-morpholin-4-yl-isoxazol-3-ylsulfanyl)-benzamide; N-[(3R)-1-azabicyclo[2.2.2]oct-3-yl]-4-(isothiazol-2-ylsulfanyl)-benzamide; N-[(3R)-1-azabicyclo[2.2.2]oct-3-yl]-4-(5-methylisothiazol-3-ylsulfanyl)-benzamide; N-[(3R)-1-azabicyclo[2.2.2]oct-3-yl]-4-(5-chloroisothiazol-3-ylsulfanyl)-benzamide; N-[(3R)-1-azabicyclo[2.2.2]oct-3-yl]-4-(5-methoxyisothiazol-3-ylsulfanyl)-benzamide;

N-[(3R)-1-azabicyclo[2.2.2]oct-3-yl]-4-(5-trifluoromethylisothiazol-3-ylsulfanyl)-benzamide; N-[(3R)-1-azabicyclo[2.2.2]oct-3-yl]-4-(5-acetylisothiazol-3-ylsulfanyl)-benzamide; N-[(3R)-1-azabicyclo[2.2.2]oct-3-yl]-4-(5-acetaminoisothiazol-3-ylsulfanyl)-benzamide; N-[(3R)-1-azabicyclo[2.2.2]oct-3-yl]-4-(5-cyanoisothiazol-3-ylsulfanyl)-benzamide; N-[(3R)-1-azabicyclo[2.2.2]oct-3-yl]-4-(5-morpholin-4-yl-isothiazol-3-ylsulfanyl)-benzamide; N-[(3R)-1-azabicyclo[2.2.2]oct-3-yl]-4-(6-methylpyridin-3-yloxy)-benzamide; N-[(3R)-1-azabicyclo[2.2.2]oct-3-yl]-4-(6-chloropyridin-3-yloxy)-benzamide; N-[(3R)-1-azabicyclo[2.2.2]oct-3-yl]-4-(6-methoxypyridin-3-yloxy)-benzamide; N-[(3R)-1-azabicyclo[2.2.2]oct-3-yl]-4-(6-trifluoromethylpyridin-3-yloxy)-benzamide; N-[(3R)-1-azabicyclo[2.2.2]oct-3-yl]-4-(6-acetylpyridin-3-yloxy)-benzamide; N-[(3R)-1-azabicyclo[2.2.2]oct-3-yl]-4-(6-acetaminopyridin-3-yloxy)-benzamide; N-[(3R)-1-azabicyclo[2.2.2]oct-3-yl]-4-(6-cyanopyridin-3-yloxy)-benzamide; N-[(3R)-1-azabicyclo[2.2.2]oct-3-yl]-4-(6-morpholin-4-yl-pyridin-3-yloxy)-benzamide; N-[(3R)-1-azabicyclo[2.2.2]oct-3-yl]-4-(2-methylpyridin-4-yloxy)-benzamide; N-[(3R)-1-azabicyclo[2.2.2]oct-3-yl]-4-(2-chloropyridin-4-yloxy)-benzamide; N-[(3R)-1-azabicyclo[2.2.2]oct-3-yl]-4-(2-methoxypyridin-4-yloxy)-benzamide; N-[(3R)-1-azabicyclo[2.2.2]oct-3-yl]-4-(2-trifluoromethylpyridin-4-yloxy)-benzamide; N-[(3R)-1-azabicyclo[2.2.2]oct-3-yl]-4-(2-acetylpyrdin-4-yloxy)-benzamide; N-[(3R)-1-azabicyclo[2.2.2]oct-3-yl]-4-(2-acetaminopyridin-4-yloxy)-benzamide; N-[(3R)-1-azabicyclo[2.2.2]oct-3-yl]-4-(2-cyanopyrdin-4-yloxy)-benzamide; N-[(3R)-1-azabicyclo[2.2.2]oct-3-yl]-4-(2-morpholin-4-yl-pyridin-4-yloxy)-benzamide; N-[(3R)-1-azabicyclo[2.2.2]oct-3-yl]-4-(5-methylpyridin-2-yloxy)-benzamide; N-[(3R)-1-azabicyclo[2.2.2]oct-3-yl]-4-(5-chloropyridin-2-yloxy)-benzamide; N-[(3R)-1-azabicyclo[2.2.2]oct-3-yl]-4-(5-methoxypyridin-2-yloxy)-benzamide; N-[(3R)-1-azabicyclo[2.2.2]oct-3-yl]-4-(5-trifluoromethylpyridin-2-yloxy)-benzamide; N-[(3R)-1-azabicyclo[2.2.2]oct-3-yl]-4-(5-acetylpyridin-2-yloxy)-benzamide; N-[(3R)-1-azabicyclo[2.2.2]oct-3-yl]-4-(5-acetaminopyridin-2-yloxy)-benzamide; N-[(3R)-1-azabicyclo[2.2.2]oct-3-yl]-4-(5-cyanopyridin-2-yloxy)-benzamide; N-[(3R)-1-azabicyclo[2.2.2]oct-3-yl]-4-(5-morpholin-4-yl-pyridin-2-yloxy)-benzamide; N-[(3R)-1-azabicyclo[2.2.2]oct-3-yl]-4-(4-methylpyridin-2-yloxy)-benzamide; N-[(3R)-1-azabicyclo[2.2.2]oct-3-yl]-4-(4-chloropyridin-2-yloxy)-benzamide; N-[(3R)-1-azabicyclo[2.2.2]oct-3-yl]-4-(4-methoxypyridin-2-yloxy)-benzamide; N-[(3R)-1-azabicyclo[2.2.2]oct-3-yl]-4-(4-trifluoromethylpyridin-2-yloxy)-benzamide; N-[(3R)-1-azabicyclo[2.2.2]oct-3-yl]-4-(4-acetylpyridin-2-yloxy)-benzamide; N-[(3R)-1-azabicyclo[2.2.2]oct-3-yl]-4-(4-acetaminopyridin-2-yloxy)-benzamide; N-[(3R)-1-azabicyclo[2.2.2]oct-3-yl]-4-(4-cyanopyridin-2-yloxy)-benzamide; N-[(3R)-1-azabicyclo[2.2.2]oct-3-yl]-4-(4-morpholin-4-yl-pyridin-2-yloxy)-benzamide; N-[(3R)-1-azabicyclo[2.2.2]oct-3-yl]-4-(6-methylpyridin-2-yloxy)-benzamide; N-[(3R)-1-azabicyclo[2.2.2]oct-3-yl]-4-(6-chloropyridin-2-yloxy)-benzamide; N-[(3R)-1-azabicyclo[2.2.2]oct-3-yl]-4-(6-methoxypyridin-2-yloxy)-benzamide; N-[(3R)-1-azabicyclo[2.2.2]oct-3-yl]-4-(6-trifluoromethylpyridin-2-yloxy)-benzamide; N-[(3R)-1-azabicyclo[2.2.2]oct-3-yl]-4-(6-acetylpyridin-2-yloxy)-benzamide; N-[(3R)-1-azabicyclo[2.2.2]oct-3-yl]-4-(6-acetaminopyridin-2-yloxy)-benzamide; N-[(3R)-1-azabicyclo[2.2.2]oct-3-yl]-4-(6-cyanopyridin-2-yloxy)-benzamide; N-[(3R)-1-azabicyclo[2.2.2]oct-3-yl]-4-(6-morpholin-4-yl-pyridin-2-yloxy)-benzamide; N-[(3R)-1-azabicyclo[2.2.2]oct-3-yl]-4-(5-methylpyridin-3-yloxy)-benzamide; N-[(3R)-1-azabicyclo[2.2.2]oct-3-yl]-4-(5-chloropyridin-3-yloxy)-benzamide; N-[(3R)-1-azabicyclo[2.2.2]oct-3-yl]-4-(5-methoxypyridin-3-yloxy)-benzamide; N-[(3R)-1-azabicyclo[2.2.2]oct-3-yl]-4-(5-trifluoromethylpyridin-3-yloxy)-benzamide; N-[(3R)-1-azabicyclo[2.2.2]oct-3-yl]-4-(5-acetylpyrdin-3-yloxy)-benzamide; N-[(3R)-1-azabicyclo[2.2.2]oct-3-yl]-4-(5-acetaminopyridin-3-yloxy)-benzamide; N-[(3R)-1-azabicyclo[2.2.2]oct-3-yl]-4-(5-cyanopyridin-3-yloxy)-benzamide; N-[(3R)-1-azabicyclo[2.2.2]oct-3-yl]-4-(5-morpholin-4-yl-pyridin-3-yloxy)-benzamide; N-[(3R)-1-azabicyclo[2.2.2]oct-3-yl]-4-(2-chloropyridin-3-yloxy)-benzamide; N-[(3R)-1-azabicyclo[2.2.2]oct-3-yl]-4-(4-chloropyridin-3-yloxy)-benzamide; N-[(3R)-1-azabicyclo[2.2.2]oct-3-yl]-4-(3-chloropyridin-4-yloxy)-benzamide; N-[(3R)-1-azabicyclo[2.2.2]oct-3-yl]-4-(3-chloropyridin-2-yloxy)-benzamide; N-[(3R)-1-azabicyclo[2.2.2]oct-3-yl]-4-(6-methylpyridin-3-ylsulfanyl)-benzamide; N-[(3R)-1-azabicyclo[2.2.2]oct-3-yl]-4-(6-chloropyridin-3-ylsulfanyl)-benzamide; N-[(3R)-1-azabicyclo[2.2.2]oct-3-yl]-4-(6-methoxypyridin-3-ylsulfanyl)-benzamide; N-[(3R)-1-azabicyclo[2.2.2]oct-3-yl]-4-(6-trifluoromethylpyridin-3-ylsulfanyl)-benzamide; N-[(3R)-1-azabicyclo[2.2.2]oct-3-yl]-4-(6-acetylpyridin-3-ylsulfanyl)-benzamide; N-[(3R)-1-azabicyclo[2.2.2]oct-3-yl]-4-(6-acetaminopyridin-3-ylsulfanyl)-benzamide; N-[(3R)-1-azabicyclo[2.2.2]oct-3-yl]-4-(6-cyanopyridin-3-ylsulfanyl)-benzamide; N-[(3R)-1-azabicyclo[2.2.2]oct-3-yl]-4-(6-morpholin-4-yl-pyridin-3-ylsulfanyl)-benzamide; N-[(3R)-1-azabicyclo[2.2.2]oct-3-yl]-4-(2-methylpyridin-4-ylsulfanyl)-benzamide; N-[(3R)-1-azabicyclo[2.2.2]oct-3-yl]-4-(2-chloropyridin-4-ylsulfanyl)-benzamide; N-[(3R)-1-azabicyclo[2.2.2]oct-3-yl]-4-(2-methoxypyridin-4-ylsulfanyl)-benzamide; N-[(3R)-1-azabicyclo[2.2.2]oct-3-yl]-4-(2-trifluoromethylpyridin-4-ylsulfanyl)-benzamide; N-[(3R)-1-azabicyclo[2.2.2]oct-3-yl]-4-(2-acetylpyridin-4-ylsulfanyl)-benzamide; N-[(3R)-1-azabicyclo[2.2.2]oct-3-yl]-4-(2-acetaminopyridin-4-ylsulfanyl)-benzamide; N-[(3R)-1-azabicyclo[2.2.2]oct-3-yl]-4-(2-cyanopyridin-4-ylsulfanyl)-benzamide; N-[(3R)-1-azabicyclo[2.2.2]oct-3-yl]-4-(2-morpholin-4-yl-pyridin-4-ylsulfanyl)-benzamide; N-[(3R)-1-azabicyclo[2.2.2]oct-3-yl]-4-(5-methylpyridin-2-ylsulfanyl)-benzamide; N-[(3R)-1-azabicyclo[2.2.2]oct-3-yl]-4-(5-chloropyridin-2-ylsulfanyl)-benzamide; N-[(3R)-1-azabicyclo[2.2.2]oct-3-yl]-4-(5-methoxypyridin-2-ylsulfanyl)-benzamide; N-[(3R)-1-azabicyclo[2.2.2]oct-3-yl]-4-(5-trifluoromethylpyridin-2-ylsulfanyl)-benzamide; N-[(3R)-1-azabicyclo[2.2.2]oct-3-yl]-4-(5-acetylpyridin-2-ylsulfanyl)-benzamide; N-[(3R)-1-azabicyclo[2.2.2]oct-3-yl]-4-(5-acetaminopyridin-2-ylsulfanyl)-benzamide; N-[(3R)-1-azabicyclo[2.2.2]oct-3-yl]-4-(5-cyanopyridin-2-ylsulfanyl)-benzamide; N-[(3R)-1-azabicyclo[2.2.2]oct-3-yl]-4-(5-morpholin-4-yl-pyridin-2-ylsulfanyl)-benzamide; N-[(3R)-1-azabicyclo[2.2.2]oct-3-yl]-4-(4-methylpyridin-2-ylsulfanyl)-benzamide; N-[(3R)-1-azabicyclo[2.2.2]oct-3-yl]-4-(4-chloropyridin-2-ylsulfanyl)-benzamide; N-[(3R)-1-azabicyclo[2.2.2]oct-3-yl]-4-(4-methoxypyridin-2-ylsulfanyl)-benzamide; N-[(3R)-1-azabicyclo[2.2.2]oct-3-yl]-4-(4-trifluoromethylpyridin-2-yl sulfanyl)-benzamide; N-[(3R)-1-azabicyclo[2.2.2]oct-3-yl]-4-(4-acetylpyridin- 2-ylsulfanyl)-benzamide; N-[(3R)-1-azabicyclo[2.2.2]oct-3-yl]-4-(4-acetaminopyridin-2-ylsulfanyl)-benzamide; N-[(3R)-1-azabicyclo[2.2.2]oct-3-yl]-4-(4-cyanopyridin-2-ylsulfanyl)-benzamide; N-[(3R)-1-azabicyclo[2.2.2]oct-3-yl]-4-(4-morpholin-4-yl-pyridin-2-ylsulfanyl)-benzamide; N-[(3R)-1-azabicyclo[2.2.2]oct-3-yl]-4-(6-methylpyridin-2-ylsulfanyl)-benzamide; N-[(3R)-1-azabicyclo[2.2.2]oct-3-yl]-4-(6chloropyridin-2-ylsulfanyl)-benzamide; N-[(3R)-1-azabicyclo[2.2.2]oct-3-yl]-4-(6-methoxypyridin-2-ylsulfanyl)-benzamide; N-[(3R)-1-azabicyclo[2.2.2]oct-3-yl]-4-(6-trifluoromethylpyridin-2-ylsulfanyl)-benzamide; N-[(3R)-1-azabicyclo[2.2.2]oct-3-yl]-4-(6-acetylpyridin-2-ylsulfanyl)-benzamide; N-[(3R)-1-azabicyclo[2.2.2]oct-3-yl]-4-(6-acetaminopyridin-2-ylsulfanyl)-benzamide; N-[(3R)-1-azabicyclo[2.2.2]oct-3-yl]-4-(6-cyanopyridin-2-ylsulfanyl)-benzamide; N-[(3R)-1-azabicyclo[2.2.2]oct-3-yl]-4-(6-morpholin-4-yl-pyridin-2-ylsulfanyl)-benzamide; N-[(3R)-1-azabicyclo[2.2.2]oct-3-yl]-4-(5-methylpyridin-3-ylsulfanyl)-benzamide; N-[(3R)-1-azabicyclo[2.2.2]oct-3-yl]-4-(5-chloropyridin-3-ylsulfanyl)-benzamide; N-[(3R)-1-azabicyclo[2.2.2]oct-3-yl]-4-(5-methoxypyridin-3-ylsulfanyl)-benzamide; N-[(3R)-1-azabicyclo[2.2.2]oct-3-yl]-4-(5-trifluoromethylpyridin-3-ylsulfanyl)-benzamide; N-[(3R)-1-azabicyclo[2.2.2]oct-3-yl]-4-(5-acetylpyridin-3-ylsulfanyl)-benzamide; N-[(3R)-1-azabicyclo[2.2.2]oct-3-yl]-4-(5-acetaminopyridin-3-ylsulfanyl)-benzamide; N-[(3R)-1-azabicyclo[2.2.2]oct-3-yl]-4-(5-cyanopyridin-3-ylsulfanyl)-benzamide; N-[(3R)-1-azabicyclo[2.2.2]oct-3-yl]-4-(5-morpholin-4-yl-pyridin-3-ylsulfanyl)-benzamide; N-[(3R)-1-azabicyclo[2.2.2]oct-3-yl]-4-(2-chloropyridin-3-ylsulfanyl)-benzamide; N-[(3R)-1-azabicyclo[2.2.2]oct-3-yl]-4-(4-chloropyridin-3-ylsulfanyl)-benzamide; N-[(3R)-1-azabicyclo[2.2.2]oct-3-yl]-4-(3-chloropyridin-4-ylsulfanyl)-benzamide; N-[(3R)-1-azabicyclo[2.2.2]oct-3-yl]-4-(3-chloropyridin-2-ylsulfanyl)-benzamide; N-[(2S,3R)-2-methyl-1-azabicyclo[2.2.2]oct-3-yl]-4-(4-aminophenoxy)-benzamide; N-[(2S,3R)-2-methyl-1-azabicyclo[2.2.2]oct-3-yl]-4-(3-aminophenoxy)-benzamide; N-[(2S,3R)-2-methyl-1-azabicyclo[2.2.2]oct-3-yl]-4-(2-aminophenoxy)-benzamide; N-[(2S,3R)-2-methyl-1-azabicyclo[2.2.2]oct-3-yl]-4-(4-methanesulfonylamino-phenoxy)-benzamide; N-[(2S,3R)-2-methyl-1-azabicyclo[2.2.2]oct-3-yl]-4-(3-methanesulfonylamino-phenoxy)-benzamide; N-[(2S,3R)-2-methyl-1-azabicyclo[2.2.2]oct-3-yl]-4-(2-methanesulfonylamino-phenoxy)-benzamide; N-[(2S,3R)-2-methyl-1-azabicyclo[2.2.2]oct-3-yl]-4-(4-acetoxyphenoxy)-benzamide; N-[(2S,3R)-2-methyl-1-azabicyclo[2.2.2]oct-3-yl]-4-(3-acetoxyphenoxy)-benzamide; N-[(2S,3R)-2-methyl-1-azabicyclo[2.2.2]oct-3-yl]-4-(2-acetoxyphenoxy)-benzamide; N-[(2S,3R)-2-methyl-1-azabicyclo[2.2.2]oct-3-yl]-4-(4-acetylphenoxy)-benzamide; N-[(2S,3R)-2-methyl-1-azabicyclo[2.2.2]oct-3-yl]-4-(3-acetylphenoxy)-benzamide; N-[(2S,3R)-2-methyl-1-azabicyclo[2.2.2]oct-3-yl]-4-(2-acetylphenoxy)-benzamide; N-[(2S,3R)-2-methyl-1-azabicyclo[2.2.2]oct-3-yl]-4-(4-carbamoylphenoxy)-benzamide; N-[(2S,3R)-2-methyl-1-azabicyclo[2.2.2]oct-3-yl]-4-(3-carbamoylphenoxy)-benzamide; N-[(2S,3R)-2methyl-1-azabicyclo[2.2.2]oct-3-yl]-4-(2-carbamoylphenoxy)-benzamide; N-[(2S,3R)-2-methyl-1-azabicyclo[2.2.2]oct-3-yl]-4-(4-cyanophenoxy)-benzamide; N-[(2S,3R)-2-methyl-1-azabicyclo[2.2.2]oct-3-yl]-4-(3-cyanophenoxy)-benzamide; N-[(2S,3R)-2-methyl-1-azabicyclo[2.2.2]oct-3-yl]-4-(2-cyanophenoxy)-benzamide; N-[(2S,3R)-2-methyl-1-azabicyclo[2.2.2]oct-3-yl]-4-(4-sulfamoylphenoxy)-benzamide; N-[(2S,3R)-2-methyl-1-azabicyclo[2.2.2]oct-3-yl]-4-(3-sulfamoylphenoxy)-benzamide; N-[(2S,3R)-2-methyl-1-azabicyclo[2.2.2]oct-3-yl]-4-(2-sulfamoylphenoxy)-benzamide; N-[(2S,3R)-2-methyl-1-azabicyclo[2.2.2]oct-3-yl]-4-(thiophen-2-yloxy)-benzamide; N-[(2S,3R)-2-methyl-1-azabicyclo[2.2.2]oct-3-yl]-4-(5-methylthiophen-2-yloxy)-benzamide; N-[(2S,3R)-2-methyl-1-azabicyclo[2.2.2]oct-3-yl]-4-(5-chlorothiophen-2-yloxy)-benzamide; N-[(2S,3R)-2-methyl-1-azabicyclo[2.2.2]oct-3-yl]-4-(5-methoxythiophen-2-yloxy)-benzamide; N-[(2S,3R)-2-methyl-1-azabicyclo[2.2.2]oct-3-yl]-4-(5-trifluoromethylthiophen-2-yloxy)-benzamide; N-[(2S,3R)-2-methyl-1-azabicyclo[2.2.2]oct-3-yl]-4-(5-acetylthiophen-2-yloxy)-benzamide; N-[(2S,3R)-2-methyl-1-azabicyclo[2.2.2]oct-3-yl]-4-(5-acetaminothiophen-2-yloxy)-benzamide; N-[(2S,3R)-2-methyl-1-azabicyclo[2.2.2]oct-3-yl]-4-(5-cyanothiophen-2-yloxy)-benzamide; N-[(2S,3R)-2-methyl-1-azabicyclo[2.2.2]oct-3-yl]-4-(5-morpholin-4-yl-thiophen-2-yloxy)-benzamide; N-[(2S,3R)-2-methyl-1-azabicyclo[2.2.2]oct-3-yl]-4-(4-methylthiophen-2-yloxy)-benzamide; N-[(2S,3R)-2-methyl-1-azabicyclo[2.2.2]oct-3-yl]-4-(4-chlorothiophen-2-yloxy)-benzamide; N-[(2S,3R)-2-methyl-1-azabicyclo[2.2.2]oct-3-yl]-4-(4-methoxythiophen-2-yloxy)-benzamide; N-[(2S,3R)-2-methyl-1-azabicyclo[2.2.2]oct-3-yl]-4-(4-trifluoromethylthiophen-2-yloxy)-benzamide; N-[(2S,3R)-2-methyl-1-azabicyclo[2.2.2]oct-3-yl]-4-(4-acetylthiophen-2-yloxy)-benzamide; N-[(2S,3R)-2-methyl-1-azabicyclo[2.2.2]oct-3-yl]-4-(4-acetaminothiophen-2-yloxy)-benzamide; N-[(2S,3R)-2-methyl-1-azabicyclo[2.2.2]oct-3-yl]-4-(4-cyanothiophen-2-yloxy)-benzamide; N-[(2S,3R)-2-methyl-1-azabicyclo[2.2.2]oct-3-yl]-4-(4-morpholin-4-yl-thiophen-2-yloxy)-benzamide; N-[(2S,3R)-2-methyl-1-azabicyclo[2.2.2]oct-3-yl]-4-(furan-2-yloxy)-benzamide; N-[(2S,3R)-2-methyl-1-azabicyclo[2.2.2]oct-3-yl]-4-(5-methylfuran-2-yloxy)-benzamide; N-[(2S,3R)-2-methyl-1-azabicyclo[2.2.2]oct-3-yl]-4-(5-chlorofuran-2-yloxy)-benzamide; N-[(2S,3R)-2-methyl-1-azabicylo[2.2.2]oct-3-yl]-4-(5-methoxyfuran-2-yloxy)-benzamide; N-[(2S,3R)-2-methyl-1-azabicyclo[2.2.2]oct-3-yl]-4-(5-trifluoromethylfuran-2-yloxy)-benzamide; N-[(2S,3R)-2-methyl-1-azabicyclo[2.2.2]oct-3-yl]-4-(5-acetylfuran-2-yloxy)-benzamide; -N-[(2S,3R)-2-methyl-1-azabicyclo[2.2.2]oct-3-yl]-4-(5-acetaminofuran-2-yloxy)-benzamide; N-[(2S,3R)-2-methyl-1-azabicyclo[2.2.2]oct-3-yl]-4-(5-cyanofuran-2-yloxy)-benzamide; N-[(2S,3R)-2-methyl-1-azabicyclo[2.2.2]oct-3-yl]-4-(5-morpholin-4-yl-furan-2-yloxy)-benzamide; N-[(2S,3R)-2-methyl-1-azabicyclo[2.2.2]oct-3-yl]-4-(4-methylfuran-2-yloxy)-benzamide; N-[(2S,3R)-2-methyl-1-azabicyclo[2.2.2]oct-3-yl]-4-(4-chlorofuran-2-yloxy)-benzamide; N-[(2S,3R)-2-methyl-1-azabicyclo[2.2.2]oct-3-yl]-4-(4-methoxyfuran-2-yloxy)-benzamide; N-[(2S,3R)-2-methyl-1-azabicyclo[2.2.2]oct-3-yl]-4-(4-trifluoromethylfuran-2-yloxy)-benzamide; N-[(2S,3R)-2-methyl-1-azabicyclo[2.2.2]oct-3-yl]-4-(4-acetylfuran-2-yloxy)-benzamide; N-[(2S,3R)-2-methyl-1-azabicyclo[2.2.2]oct-3-yl]-4-(4-acetaminofuran-2-yloxy)-benzamide; N-[(2S,3R)-2-methyl-1-azabicyclo[2.2.2]oct-3-yl]-4-(4-cyanofuran-2-yloxy)-benzamide; N-[(2S,3R)-2-methyl-1-azabicyclo[2.2.2]oct-3-yl]-4-(4-morpholin-4-yl-furan-2-yloxy)-benzamide; N-[(2S,3R)-2-methyl-1- azabicyclo[2.2.2]oct-3-yl]-4-(oxazol-2-yloxy)-benzamide; N-[(2S,3R)-2-methyl-1-azabicyclo[2.2.2]oct-3-yl]-4-(5-methyloxazol-2-yloxy)-benzamide; N-[(2S,3R)-2-methyl-1-azabicyclo[2.2.2]oct-3-yl]-4-(5-chlorooxazol-2-yloxy)-benzamide; N-[(2S,3R)-2-methyl-1-azabicyclo[2.2.2]oct-3-yl]-4-(5-methoxyoxazol-2-yloxy)-benzamide; N-[(2S,3R)-2-methyl-1-azabicyclo[2.2.2]oct-3-yl]-4-(5-trifluoromethyloxazol-2-yloxy)-benzamide; N-[(2S,3R)-2-methyl-1-azabicyclo[2.2.2]oct-3-yl]-4-(5-acetyloxazol-2-yloxy)-benzamide; N-[(2S,3R)-2-methyl-1-azabicyclo[2.2.2]oct-3-yl]-4-(5-acetaminooxazol-2-yloxy)-benzamide; N-[(2S,3R)-2-methyl-1-azabicyclo[2.2.2]oct-3-yl]-4-(5-cyanooxazol-2-yloxy)-benzamide; N-[(2S,3R)-2-methyl-1-azabicyclo[2.2.2]oct-3-yl]-4-(5-morpholin-4-yl-oxazol-2-yloxy)-benzamide; N-[(2S,3R)-2-methyl-1-azabicyclo[2.2.2]oct-3-yl]-4-(oxazol-2-yloxy)-benzamide; N-[(2S,3R)-2-methyl-1-azabicyclo[2.2.2]oct-3-yl]-4-(4-methyloxazol-2-yloxy)-benzamide; N-[(2S,3R)-2-methyl-1-azabicyclo[2.2.2]oct-3-yl]-4-(4-chlorooxazol-2-yloxy)-benzamide; N-[(2S,3R)-2-methyl-1-azabicyclo[2.2.2]oct-3-yl]-4-(4-methoxyoxazol-2-yloxy)-benzamide; N-[(2S,3R)-2-methyl-1-azabicyclo[2.2.2]oct-3-yl]-4-(4-trifluoromethyloxazol-2-yloxy)-benzamide; N-[(2S,3R)-2-methyl-1-azabicyclo[2.2.2]oct-3-yl]-4-(4-acetyloxazol-2-yloxy)-benzamide; N-[(2S,3R)-2-methyl-1-azabicyclo[2.2.2]oct-3-yl]-4-(4-acetaminooxazol-2-yloxy)-benzamide; N-[(2S,3R)-2-methyl-1-azabicyclo[2.2.2]oct-3-yl]-4-(4-cyanooxazol-2-yloxy)-benzamide; N-[(2S,3R)-2-methyl-1-azabicyclo[2.2.2]oct-3-yl]-4-(4-morpholin-4-yl-oxazol-2-yloxy)-benzamide; N-[(2S,3R)-2-methyl-1-azabicyclo[2.2.2]oct-3-yl]-4(oxazol-5-yloxy)-benzamide; N-[(2S,3R)-2-methyl-1-azabicyclo[2.2.2]oct-3-yl]-4-(2-methyloxazol-5-yloxy)-benzamide; N-[(2S,3R)-2-methyl-1-azabicyclo[2.2.2]oct-3-yl]-4-(2-chlorooxazol-5-yloxy)-benzamide; N-[(2S,3R)-2-methyl-1-azabicyclo[2.2.2]oct-3-yl]-4-(2-methoxyoxazol-5-yloxy)-benzamide; N-[(2S,3R)-2-methyl-1-azabicyclo[2.2.2]oct-3-yl]-4-(2-trifluoromethyloxazol-5-yloxy)-benzamide; N-[(2S,3R)-2-methyl-1-azabicyclo[2.2.2]oct-3-yl]-4-(2-acetyloxazol-5-yloxy)-benzamide; N-[(2S,3R)-2-methyl-1-azabicyclo[2.2.2]oct-3-yl]-4-(2-acetaminooxazol-5-yloxy)-benzamide; N-[(2S,3R)-2-methyl-1-azabicyclo[2.2.2]oct-3-yl]-4-(2-cyanooxazol-5-yloxy)-benzamide; N-[(2S,3R)-2-methyl-1-azabicyclo[2.2.2]oct-3-yl]-4-(2-morpholin-4-yl-oxazol-5-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4(5-methylthiazol-2-yloxy)-benzamide; N-[(2S,3R)-2-methyl-1-azabicyclo[2.2.2]oct-3-yl]-4-(5-chlorothiazol–2-yloxy)-benzamide; N-[(2S,3R)-2-methyl-1-azabicyclo[2.2.2]oct-3-yl]-4-(5-methoxythiazol-2-yloxy)-benzamide; N-[(2S,3R)-2-methyl-1-azabicyclo[2.2.2]oct-3-yl]-4-(5-trifluoromethylthiazol-2-yloxy)-benzamide; N-[(2S,3R)-2-methyl-1-azabicyclo[2.2.2]oct-3-yl]-4-(5-acetylthiazol-2-yloxy)-benzamide; N-[(2S,3R)-2-methyl-1-azabicyclo[2.2.2]oct-3-yl]-4-(5-acetaminothiazol-2-yloxy)-benzamide; N-[(2S,3R)-2-methyl-1-azabicyclo[2.2.2]oct-3-yl]-4-(5-cyanothiazol-2-yloxy)-benzamide; N-[(2S,3R)-2-methyl-1-azabicyclo[2.2.2]oct-3-yl]-4-(5-morpholin-4-yl-thiazol-2-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4-(4-methylthiazol-2-yloxy)-benzamide; N-[(2S,3R)-2-methyl-1-azabicyclo[2.2.2]oct-3-yl]-4-(4-chlorothiazol-2-yloxy)-benzamide; N-[(2S,3R)-2-methyl-1-azabicyclo[2.2.2]oct-3-yl]-4-(4-methoxythiazol-2-yloxy)-benzamide; N-[(2S,3R)-2-methyl-1-azabicyclo[2.2.2]oct-3-yl]-4-(4-trifluoromethylthiazol-2-yloxy)-benzamide; N-[(2S,3R)-2-methyl-1-azabicyclo[2.2.2]oct-3-yl]-4-(4-acetylthiazol-2-yloxy)-benzamide; N-[(2S,3R)-2-methyl-1-azabicyclo[2.2.2]oct-3-yl]-4-(4-acetaminothiazol-2-yloxy)-benzamide; N-[(2S,3R)-2-methyl-1-azabicyclo[2.2.2]oct-3-yl]4-(4-cyanothiazol-2-yloxy)-benzamide; N-[(2S,3R)-2-methyl-1-azabicyclo[2.2.2]oct-3-yl]-4-(4-morpholin-4-yl-thiazol-2-yloxy)-benzamide; N-[(2S,3R)-2-methyl-1-azabicyclo[2.2.2]oct-3-yl]-4-(thiazol-5-yloxy)-benzamide; N-[(2S,3R)-2-methyl-1-azabicyclo[2.2.2]oct-3-yl]-4-(2-methylthiazol-5-yloxy)-benzamide; N-[(2S,3R)-2-methyl-1-azabicyclo[2.2.2]oct-3-yl]-4-(2-chlorothiazol-5-yloxy)-benzamide; N-[(2S,3R)-2-methyl-1-azabicyclo[2.2.2]oct-3-yl]-4-(2-methoxythiazol-5-yloxy)-benzamide; N-[(2S,3R)-2-methyl-1-azabicyclo[2.2.2]oct-3-yl]-4-(2-trifluoromethylthiazol-5-yloxy)-benzamide; N-[(2S,3R)-2-methyl-1-azabicyclo[2.2.2]oct-3-yl]-4-(2-acetylthiazol-5-yloxy)-benzamide; N-[(2S,3R)-2-methyl-1-azabicyclo[2.2.2]oct-3-yl]-4-(2-acetaminothiazol-5-yloxy)-benzamide; N-[(2S,3R)-2-methyl-1-azabicyclo[2.2.2]oct-3-yl]-4-(2-cyanothiazol-5-yloxy)-benzamide; N-[(2S,3R)-2-methyl-1-azabicyclo[2.2.2]oct-3-yl]-4-(2-morpholin-4-yl-thiazol-5-yloxy)-benzamide; N-[(2S,3R)-2-methyl-1-azabicyclo[2.2.2]oct-3-yl]-4-([1,3,4]oxadiazol-2-yloxy)-benzamide; N-[(2S,3R)-2-methyl-1-azabicyclo[2.2.2]oct-3-yl]-4-(5-methyl[1,3,4]oxadiazol-2-yloxy)-benzamide; N-[(2S,3R)-2-methyl-1-azabicyclo[2.2.2]oct-3-yl]-4-(5-chloro[1,3,4]oxadiazol-2-yloxy)-benzamide; N-[(2S,3R)-2-methyl-1-azabicyclo[2.2.2]oct-3-yl]-4-(5-methoxy[1,3,4]oxadiazol-2-yloxy)-benzamide; N-[(2S,3R)-2-methyl-1-azabicyclo[2.2.2]oct-3-yl]-4-(5-trifluoromethyl[1,3,4]oxadiazol-2-yloxy)-benzamide; N-[(2S,3R)-2-methyl-1-azabicyclo[2.2.2]oct-3-yl]-4-(5-acetyl[1,3,4]oxadiazol-2-yloxy)-benzamide; N-[(2S,3R)-2-methyl-1-azabicyclo[2.2.2]oct-3-yl]-4-(5-acetamino[1,3,4]oxadiazol-2-yloxy)-benzamide; N-[(2S,3R)-2-methyl-1-azabicyclo[2.2.2]oct-3-yl]-4-(5-cyano[1,3,4]oxadiazol-2-yloxy)-benzamide; N-[(2S,3R)-2-methyl-1-azabicyclo[2.2.2]oct-3-yl]-4-(5-morpholin-4-yl-[1,3,4]oxadiazol-2-yloxy)-benzamide; N-[(2S,3R)-2-methyl-1-azabicyclo[2.2.2]oct-3-yl]-4-([1,3,4]thiadiazol-2-yloxy)-benzamide; N-[(2S,3R)-2-methyl-1-azabicyclo[2.2.2]oct-3-yl]-4-(5-methyl[1,3,4]thiadiazol-2-yloxy)-benzamide; N-[(2S,3R)-2-methyl-1-azabicyclo[2.2.2]oct-3-yl]-4-(5-chloro[1,3,4]thiadiazol-2-yloxy)-benzamide; N-[(2S,3R)-2-methyl-1-azabicyclo[2.2.2]oct-3-yl]-4-(5-methoxy[1,3,4]thiadiazol-2-yloxy)-benzamide; N-[(2S,3R)-2-methyl-1-azabicyclo[2.2.2]oct-3-yl]-4-(5-trifluoromethyl[1,3,4]thiadiazol-2-yloxy)-benzamide; N-[(2S,3R)-2-methyl-1-azabicyclo[2.2.2]oct-3-yl]-4-(5-acetyl[1,3,4]thiadiazol-2-yloxy)-benzamide; N-[(2S,3R)-2-methyl-1-azabicyclo[2.2.2]oct-3-yl]-4-(5-acetamino[1,3,4]thiadiazol-2-yloxy)-benzamide; N-[(2S,3R)-2-methyl-1-azabicyclo[2.2.2]oct-3-yl]-4-(5-cyano[1,3,4]thiadiazol-2-yloxy)-benzamide; N-[(2S,3R)-2-methyl-1-azabicyclo[2.2.2]oct-3-yl]-4-(5-morpholin-4-yl-[1,3,4]thiadiazol-2-yloxy)-benzamide; N-[(2S,3R)-2-methyl-1-azabicyclo[2.2.2]oct-3-yl]-4-(4-aminophenylsulfanyl)-benzamide; N-[(2S,3R)-2-methyl-1-azabicyclo[2.2.2]oct-3-yl]-4-(3-aminophenylsulfanyl)-benzamide; N-[(2S,3R)-2-methyl-1-azabicyclo[2.2.2]oct-3-yl]-4-(2-aminophenylsulfanyl)-benzamide; N-[(2S,3R)-2-methyl-1-azabicyclo[2.2.2]oct-3-yl]-4-(4-methanesulfonylamino-phenylsulfanyl)-benzamide;

N-[(2S,3R)-2-methyl-1-azabicyclo[2.2.2]oct-3-yl]-4-(3-methanesulfonylamino-phenylsulfanyl)-benzamide; N-[(2S,3R)-2-methyl-1-azabicyclo[2.2.2]oct-3-yl]-4-(2-methanesulfonylamino-phenylsulfanyl)-benzamide; N-[(2S,3R)-2-methyl-1-azabicyclo[2.2.2]oct-3-yl]-4-(4-acetoxyphenylsulfanyl)-benzamide; N-[(2S,3R)-2-methyl-1-azabicyclo[2.2.2]oct-3-yl]-4-(3-acetoxyphenylsulfanyl)-benzamide; N-[(2S,3R)-2-methyl-1-azabicyclo[2.2.2]oct-3-yl]-4-(2-acetoxyphenylsulfanyl)-benzamide; N-[(2S,3R)-2-methyl-1-azabicyclo[2.2.2]oct-3-yl]-4-(4-acetylphenylsulfanyl)-benzamide; N-[(2S,3R)-2-methyl-1-azabicyclo[2.2.2]oct-3-yl]-4-(3-acetylphenylsulfanyl)-benzamide; N-[(2S,3R)-2-methyl-1-azabicyclo[2.2.2]oct-3-yl]-4-(2-acetylphenylsulfanyl)-benzamide; N-[(2S,3R)-2-methyl-1-azabicyclo[2.2.2]oct-3-yl]-4-(4-carbamoylphenylsulfanyl)-benzamide; N-[(2S,3R)-2-methyl-1-azabicyclo[2.2.2]oct-3-yl]-4-(3-carbamoylphenylsulfanyl)-benzamide; N-[(2S,3R)-2-methyl-1-azabicyclo[2.2.2]oct-3-yl]-4-(2-carbamoylphenylsulfanyl)-benzamide; N-[(2S,3R)-2-methyl-1-azabicyclo[2.2.2]oct-3-yl]-4-(4-cyanophenylsulfanyl)-benzamide; N-[(2S,3R)-2-methyl-1-azabicyclo[2.2.2]oct-3-yl]-4-(3-cyanophenylsulfanyl)-benzamide; N-[(2S,3R)-2-methyl-1-azabicyclo[2.2.2]oct-3-yl]-4-(2-cyanophenylsulfanyl)-benzamide; N-[(2S,3R)-2-methyl-1-azabicyclo[2.2.2]oct-3-yl]-4-(4-sulfamoylphenylsulfanyl)-benzamide; N-[(2S,3R)-2-methyl-1-azabicyclo[2.2.2]oct-3-yl]-4-(3-sulfamoylphenylsulfanyl)-benzamide; N-[(2S,3R)-2-methyl-1-azabicyclo[2.2.2]oct-3-yl]-4-(2-sulfamoylphenylsulfanyl)-benzamide; N-[(2S,3R)-2-methyl-1-azabicyclo[2.2.2]oct-3-yl]-4-(4-hydroxyphenylsulfanyl)-benzamide; N-[(2S,3R)-2-methyl-1-azabicyclo[2.2.2]oct-3-yl]-4-(3-hydroxyphenylsulfanyl)-benzamide; N-[(2S,3R)-2-methyl-1-azabicyclo[2.2.2]oct-3-yl]-4-(2-hydroxyphenylsulfanyl)-benzamide; N-[(2S,3R)-2-methyl-1-azabicyclo[2.2.2]oct-3-yl]-4-(4-acetamidophenylsulfanyl)-benzamide; N-[(2S,3R)-2-methyl-1-azabicyclo[2.2.2]oct-3-yl]-4-(3-acetamidophenylsulfanyl)-benzamide; N-[(2S,3R)-2-methyl-1-azabicyclo[2.2.2]oct-3-yl]-4-(2-acetamidophenylsulfanyl)-benzamide; N-[(2S,3R)-2-methyl-1-azabicyclo[2.2.2]oct-3-yl]-4-(thiophen-2-ylsulfanyl)-benzamide; N-[(2S,3R)-2-methyl-1-azabicyclo[2.2.2]oct-3-yl]-4-(5-methylthiophen-2-ylsulfanyl)-benzamide; N-[(2S,3R)-2-methyl-1-azabicyclo[2.2.2]oct-3-yl]-4-(5-chlorothiophen-2-ylsulfanyl)-benzamide; N-[(2S,3R)-2-methyl-1-azabicyclo[2.2.2]oct-3-yl]-4-(5-methoxythiophen-2-ylsulfanyl)-benzamide; N-[(2S,3R)-2-methyl-1-azabicyclo[2.2.2]oct-3-yl]-4-(5-trifluoromethylthiophen-2-ylsulfanyl)-benzamide; N-[(2S,3R)-2-methyl-1-azabicyclo[2.2.2]oct-3-yl]-4-(5-acetylthiophen-2-ylsulfanyl)-benzamide; N-[(2S,3R)-2-methyl-1-azabicyclo[2.2.2]oct-3-yl]-4-(5-acetaminothiophen-2-ylsulfanyl)-benzamide; N-[(2S,3R)-2-methyl-1-azabicyclo[2.2.2]oct-3-yl]-4-(5-cyanothiophen-2-ylsulfanyl)-benzamide; N-[(2S,3R)-2-methyl-1-azabicyclo[2.2.2]oct-3-yl]-4-(5-morpholin-4-yl-thiophen-2-ylsulfanyl)-benzamide; N-[(2S,3R)-2-methyl-1-azabicyclo[2.2.2]oct-3-yl]-4-(4-methylthiophen-2-ylsulfanyl)-benzamide; N-[(2S,3R)-2-methyl-1-azabicyclo[2.2.2]oct-3-yl]-4-(4-chlorothiophen-2-ylsulfanyl)-benzamide; N-[(2S,3R)-2-methyl-1-azabicyclo[2.2.2]oct-3-yl]-4-(4-methoxythiophen-2-ylsulfanyl)-benzamide; N-[(2S,3R)-2-methyl-1-azabicyclo[2.2.2]oct-3-yl]-4-(4-trifluoromethylthiophen-2-ylsulfanyl)-benzamide; N-[(2S,3R)-2-methyl-1-azabicyclo[2.2.2]oct-3-yl]-4-(4-acetylthiophen-2-ylsulfanyl)-benzamide; N-[(2S,3R)-2-methyl-1-azabicyclo[2.2.2]oct-3-yl]-4-(4-acetaminothiophen-2-ylsulfanyl)-benzamide; N-[(2S,3R)-2-methyl-1-azabicyclo[2.2.2]oct-3-yl]-4-(4-cyanothiophen-2-ylsulfanyl)-benzamide; N-[(2S,3R)-2-methyl-1-azabicyclo[2.2.2]oct-3-yl]-4-(4-morpholin-4-yl-thiophen-2-ylsulfanyl)-benzamide; N-[(2S,3R)-2-methyl-1-azabicyclo[2.2.2]oct-3-yl]-4-(furan-2-ylsulfanyl)-benzamide; N-[(2S,3R)-2-methyl-1-azabicyclo[2.2.2]oct-3-yl]-4-(5-methylfuran-2-ylsulfanyl)-benzamide; N-[(2S,3R)-2-methyl-1-azabicyclo[2.2.2]oct-3-yl]-4-(5-chlorofuran-2-ylsulfanyl)-benzamide; N-[(2S,3R)-2-methyl-1-azabicyclo[2.2.2]oct-3-yl]-4-(5-methoxyfuran-2-ylsulfanyl)-benzamide; N-[(2S,3R)-2-methyl-1-azabicyclo[2.2.2]oct-3-yl]-4-(5-trifluoromethylfuran-2-ylsulfanyl)-benzamide; N-[(2S,3R)-2-methyl-1-azabicyclo[2.2.2]oct-3-yl]-4-(5-acetylfuran-2-ylsulfanyl)-benzamide; N-[(2S,3R)-2-methyl-1-azabicyclo[2.2.2]oct-3-yl]-4-(5-acetaminofuran-2-ylsulfanyl)-benzamide; N-[(2S,3R)-2-methyl-1-azabicyclo[2.2.2]oct-3-yl]-4-(5-cyanofuran-2-ylsulfanyl)-benzamide; N-[(2S,3R)-2-methyl-1-azabicyclo[2.2.2]oct-3-yl]-4-(5-morpholin-4-yl-furan-2-ylsulfanyl)-benzamide; N-[(2S,3R)-2-methyl-1-azabicyclo[2.2.2]oct-3-yl]-4-(4-methylfuran-2-ylsulfanyl)-benzamide; N-[(2S,3R)-2-methyl-1-azabicyclo[2.2.2]oct-3-yl]-4-(4-chlorofuran-2-ylsulfanyl)-benzamide; N-[(2S,3R)-2-methyl-1-azabicyclo[2.2.2]oct-3-yl]-4-(4-methoxyfuran-2-ylsulfanyl)-benzamide; N-[(2S,3R)-2-methyl-1-azabicyclo[2.2.2]oct-3-yl]-4-(4-trifluoromethylfuran-2-ylsulfanyl)-benzamide; N-[(2S,3R)-2-methyl-1-azabicyclo[2.2.2]oct-3-yl]-4-(4-acetylfuran-2-ylsulfanyl)-benzamide; N-[(2S,3R)-2-methyl-1-azabicyclo[2.2.2]oct-3-yl]-4-(4-acetaminofuran-2-ylsulfanyl)-benzamide; N-[(2S,3R)-2-methyl-1-azabicyclo[2.2.2]oct-3-yl]-4-(4-cyanofuran-2-ylsulfanyl)-benzamide; N-[(2S,3R)-2-methyl-1-azabicyclo[2.2.2]oct-3-yl]-4-(4-morpholin-4-yl-furan-2-ylsulfanyl)-benzamide; N-[(2S,3R)-2-methyl-1-azabicyclo[2.2.2]oct-3-yl]-4-(oxazol-2-ylsulfanyl)-benzamide; N-[(2S,3R)-2-methyl-1-azabicyclo[2.2.2]oct-3-yl]-4-(5-methyloxazol-2-ylsulfanyl)-benzamide; N-[(2S,3R)-2-methyl-1-azabicyclo[2.2.2]oct-3-yl]-4-(5-chlorooxazol-2-ylsulfanyl)-benzamide; N-[(2S,3R)-2-methyl-1-azabicyclo[2.2.2]oct-3-yl]-4-(5-methoxyoxazol-2-ylsulfanyl)-benzamide; N-[(2S,3R)-2-methyl-1-azabicyclo[2.2.2]oct-3-yl]-4-(5-trifluoromethyloxazol-2-ylsulfanyl)-benzamide; N-[(2S,3R)-2-methyl-1-azabicyclo[2.2.2]oct-3-yl]-4-(5-acetyloxazol-2-ylsulfanyl)-benzamide; N-[(2S,3R)-2-methyl-1-azabicyclo[2.2.2]oct-3-yl]-4-(5-acetaminooxazol-2-ylsulfanyl)-benzamide; N-[(2S,3R)-2-methyl-1-azabicyclo[2.2.2]oct-3-yl]-4-(5-cyanooxazol-2-ylsulfanyl)-benzamide; N-[(2S,3R)-2-methyl-1-azabicyclo[2.2.2]oct-3-yl]-4-(5-morpholin-4-yl-oxazol-2-ylsulfanyl)-benzamide; N-[(2S,3R)-2-methyl-1-azabicyclo[2.2.2]oct-3-yl]-4-(oxazol-2-ylsulfanyl)-benzamide; N-[(2S,3R)-2-methyl-1-azabicyclo[2.2.2]oct-3-yl]-4-(4-methyloxazol-2-ylsulfanyl)-benzamide; N-[(2S,3R)-2-methyl-1-azabicyclo[2.2.2]oct-3-yl]-4-(4-chlorooxazol-2-ylsulfanyl)-benzamide; N-[(2S,3R)-2-methyl-1-azabicyclo[2.2.2]oct-3-yl]-4-(4- methoxyoxazol-2-ylsulfanyl)-benzamide; N-[(2S,3R)-2-methyl-1-azabicyclo[2.2.2]oct-3-yl]-4-(4-trifluoromethyloxazol-2-ylsulfanyl)-benzamide; N-[(2S,3R)-2-methyl-1-azabicyclo[2.2.2]oct-3-yl]-4-(4-acetyloxazol-2-ylsulfanyl)-benzamide; N-[(2S,3R)-2-methyl-1-azabicyclo[2.2.2]oct-3-yl]-4-(4-acetaminooxazol-2-ylsulfanyl)-benzamide; N-[(2S,3R)-2-methyl-1-azabicyclo[2.2.2]oct-3-yl]-4-(4-cyanooxazol-2-ylsulfanyl)-benzamide; N-[(2S,3R)-2-methyl-1-azabicyclo[2.2.2]oct-3-yl]-4-(4-morpholin-4-yl-oxazol-2-ylsulfanyl)-benzamide; N-[(2S,3R)-2-methyl-1-azabicyclo[2.2.2]oct-3-yl]-4-(oxazol-5-ylsulfanyl)-benzamide; N-[(2S,3R)-2-methyl-1-azabicyclo[2.2.2]oct-3-yl]-4-(2-methyloxazol-5-ylsulfanyl)-benzamide; N-[(2S,3R)-2-methyl-1-azabicyclo[2.2.2]oct-3-yl]-4-(2-chlorooxazol-5-ylsulfanyl)-benzamide; N-[(2S,3R)-2-methyl-1-azabicyclo[2.2.2]oct-3-yl]-4-(2-methoxyoxazol-5-ylsulfanyl)-benzamide; N-[(2S,3R)-2-methyl-1-azabicyclo[2.2.2]oct-3-yl]-4-(2-trifluoromethyloxazol-5-ylsulfanyl)-benzamide; N-[(2S,3R)-2-methyl-1-azabicyclo[2.2.2]oct-3-yl]-4-(2-acetyloxazol-5-ylsulfanyl)-benzamide; N-[(2S,3R)-2-methyl-1-azabicyclo[2.2.2]oct-3-yl]-4-(2-acetaminooxazol-5-ylsulfanyl)-benzamide; N-[(2S,3R)-2-methyl-1-azabicyclo[2.2.2]oct-3-yl]-4-(2-cyanooxazol-5-ylsulfanyl)-benzamide; N-[(2S,3R)-2-methyl-1-azabicyclo[2.2.2]oct-3-yl]-4-(2-morpholin-4-yl-oxazol-5-ylsulfanyl)-benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(5-methylthiazol-2-ylsulfanyl)-benzamide; N-[(2S,3R)-2-methyl-1-azabicyclo[2.2.2]oct-3-yl]-4-(5-chlorothiazol-2-ylsulfanyl)-benzamide; N-[(2S,3R)-2-methyl-1-azabicyclo[2.2.2]oct-3-yl]-4-(5-methoxythiazol-2-ylsulfanyl)-benzamide; N-[(2S,3R)-2-methyl-1-azabicyclo[2.2.2]oct-3-yl]-4-(5-trifluoromethylthiazol-2-ylsulfanyl)-benzamide; N-[(2S,3R)-2-methyl-1-azabicyclo[2.2.2]oct-3-yl]-4-(5-acetylthiazol-2-ylsulfanyl)-benzamide; N-[(2S,3R)-2-methyl-1-azabicyclo[2.2.2]oct-3-yl]-4-(5-acetaminothiazol-2-ylsulfanyl)-benzamide; N-[(2S,3R)-2-methyl-1-azabicyclo[2.2.2]oct-3-yl]-4-(5-cyanothiazol-2-ylsulfanyl)-benzamide; N-[(2S,3R)-2-methyl-1-azabicyclo[2.2.2]oct-3-yl]-4-(5-morpholin-4-yl-thiazol-2-ylsulfanyl)-benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(4-methylthiazol-2-ylsulfanyl)-benzamide; N-[(2S,3R)-2-methyl-1-azabicyclo[2.2.2]oct-3-yl]-4-(4-chlorothiazol-2-ylsulfanyl)-benzamide; N-[(2S,3R)-2-methyl-1-azabicyclo[2.2.2]oct-3-yl]-4-(4-methoxythiazol-2-ylsulfanyl)-benzamide; N-[(2S,3R)-2-methyl-1-azabicyclo[2.2.2]oct-3-yl]-4-(4-trifluoromethylthiazol-2-ylsulfanyl)-benzamide; N-[(2S,3R)-2-methyl-1-azabicyclo[2.2.2]oct-3-yl]-4-(4-acetylthiazol-2-ylsulfanyl)-benzamide; N-[(2S,3R)-2-methyl-1-azabicyclo[2.2.2]oct-3-yl]-4-(4-acetaminothiazol-2-ylsulfanyl)-benzamide; N-[(2S,3R)-2-methyl-1-azabicyclo[2.2.2]oct-3-yl]-4-(4-cyanothiazol-2-ylsulfanyl)-benzamide; N-[(2S,3R)-2-methyl-1-azabicyclo[2.2.2]oct-3-yl]-4-(4-morpholin-4-yl-thiazol-2-ylsulfanyl)-benzamide; N-[(2S,3R)-2-methyl-1-azabicyclo[2.2.2]oct-3-yl]-4-(thiazol-5-ylsulfanyl)-benzamide; N-[(2S,3R)-2-methyl-1-azabicyclo[2.2.2]oct-3-yl]-4-(2-methylthiazol-5-ylsulfanyl)-benzamide; N-[(2S,3R)-2-methyl-1-azabicyclo[2.2.2]oct-3-yl]-4-(2-chlorothiazol-5-ylsulfanyl)-benzamide; N-[(2S,3R)-2-methyl-1-azabicyclo[2.2.2]oct-3-yl]-4-(2-methoxythiazol-5-ylsulfanyl)-benzamide; N-[(2S,3R)-2-methyl-1-azabicyclo[2.2.2]oct-3-yl]-4-(2-trifluoromethylthiazol-5-ylsulfanyl)-benzamide; N-[(2S,3R)-2-methyl-1-azabicyclo[2.2.2]oct-3-yl]-4-(2-acetylthiazol-5-ylsulfanyl)-benzamide; N-[(2S,3R)-2-methyl-1-azabicyclo[2.2.2]oct-3-yl]-4-(2-acetaminothiazol-5-ylsulfanyl)-benzamide; N-[(2S,3R)-2-methyl-1-azabicyclo[2.2.2]oct-3-yl]-4-(2-cyanothiazol-5-ylsulfanyl)-benzamide; N-[(2S,3R)-2-methyl-1-azabicyclo[2.2.2]oct-3-yl]-4-(2-morpholin-4-yl-thiazol-5-ylsulfanyl)-benzamide; N-[(2S,3R)-2-methyl-1-azabicyclo[2.2.2]oct-3-yl]-4-([1,3,4]oxadiazol-2-ylsulfanyl)-benzamide; N-[(2S,3R)-2-methyl-1-azabicyclo[2.2.2]oct-3-yl]-4-(5-methyl[1,3,4]oxadiazol-2-ylsulfanyl)-benzamide; N-[(2S,3R)-2-methyl-1-azabicyclo[2.2.2]oct-3-yl]-4-(5-chloro[1,3,4]oxadiazol-2-ylsulfanyl)-benzamide; N-[(2S,3R)-2-methyl-1-azabicyclo[2.2.2]oct-3-yl]-4-(5-methoxy[1,3,4]oxadiazol-2-trifluoromethyl[1,3,4]oxadiazol-2-ylsulfanyl)-benzamide; N-[(2S,3R)-2-methyl-1-azabicyclo[2.2.2]oct-3-yl]-4-(5-acetyl[1,3,4]oxadiazol-2-ylsulfanyl)-benzamide; N-[(2S,3R)-2-methyl-1-azabicyclo[2.2.2]oct-3-yl]-4-(5-acetamino[1,3,4]oxadiazol-2-ylsulfanyl)-benzamide; N-[(2S,3R)-2-methyl-1-azabicyclo[2.2.2]oct-3-yl]-4-(5-cyano[1,3,4]oxadiazol-2-ylsulfanyl)-benzamide; N-[(2S,3R)-2-methyl-1-azabicyclo[2.2.2]oct-3-yl]-4-(5-morpholin-4-yl-[1,3,4]oxadiazol-2-ylsulfanyl)-benzamide; N-[(2S,3R)-2-methyl-1-azabicyclo[2.2.2]oct-3-yl]-4-([1,3,4]thiadiazol-2-ylsulfanyl)-benzamide; N-[(2S,3R)-2-methyl-1-azabicyclo[2.2.2]oct-3-yl]-4-(5-methyl[1,3,4]thiadiazol-2-ylsulfanyl)-benzamide; N-[(2S,3R)-2-methyl-1-azabicyclo[2.2.2]oct-3-yl]-4-(5-chloro[1,3,4]thiadiazol-2-ylsulfanyl)-benzamide; N-[(2S,3R)-2-methyl-1-azabicyclo[2.2.2]oct-3-yl]-4-(5-methoxy[1,3,4]thiadiazol-2-ylsulfanyl)-benzamide; N-[(2S,3R)-2-methyl-1-azabicyclo[2.2.2]oct-3-yl]-4-(5-trifluoromethyl[1,3,4]thiadiazol-2-ylsulfanyl)-benzamide; N-[(2S,3R)-2-methyl-1-azabicyclo[2.2.2]oct-3-yl]-4-(5-acetyl[1,3,4]thiadiazol-2-ylsulfanyl)-benzamide; N-[(2S,3R)-2-methyl-1-azabicyclo[2.2.2]oct-3-yl]-4-(5-acetamino[1,3,4]thiadiazol-2-ylsulfanyl)-benzamide; N-[(2S,3R)-2-methyl-1-azabicyclo[2.2.2]oct-3-yl]-4-(5-cyano[1,3,4]thiadiazol-2-ylsulfanyl)-benzamide; N-[(2S,3R)-2-methyl-1-azabicyclo[2.2.2]oct-3-yl]-4-(5-morpholin-4-yl-[1,3,4]thiadiazol-2-ylsulfanyl)-benzamide; N-[(2S,3R)-2-methyl-1-azabicyclo[2.2.2]oct-3-yl]-4-(pyrrol-2-yloxy)-benzamide; N-[(2S,3R)-2-methyl-1-azabicyclo[2.2.2]oct-3-yl]-4-(5-methylpyrrol-2-yloxy)-benzamide; N-[(2S,3R)-2-methyl-1-azabicyclo[2.2.2]oct-3-yl]-4-(5-chloropyrrol-2-yloxy)-benzamide; N-[(2S,3R)-2-methyl-1-azabicyclo[2.2.2]oct-3-yl]-4-(5-methoxypyrrol-2-yloxy)-benzamide; N-[(2S,3R)-2-methyl-1-azabicyclo[2.2.2]oct-3-yl]-4-(5-trifluoromethylpyrrol-2-yloxy)-benzamide; N-[(2S,3R)-2-methyl-1-azabicyclo[2.2.2]oct-3-yl]-4-(5-acetylpyrrol-2-yloxy)-benzamide; N-[(2S,3R)-2-methyl-1-azabicyclo[2.2.2]oct-3-yl]-4-(5-acetaminopyrrol-2-yloxy)-benzamide; N-[(2S,3R)-2-methyl-1-azabicyclo[2.2.2]oct-3-yl]-4-(5-cyanopyrrol-2-yloxy)-benzamide; N-[(2S,3R)-2-methyl-1-azabicyclo[2.2.2]oct-3-yl]-4-(5-morpholin-4-yl-pyrrol-2-yloxy)-benzamide; N-[(2S,3R)-2-methyl-1-azabicyclo[2.2.2]oct-3-yl]-4-(3H-imidazol-4-yloxy)-benzamide; N-[(2S,3R)-2-methyl-1-azabicyclo[2.2.2]oct-3-yl]-4-(2-methyl-3H-imidazol-4-yloxy)-benzamide; N-[(2S,3R)-2-methyl-1-azabicyclo[2.2.2]oct-3-yl]-4-(2-chloro-3H-imidazol-4- yloxy)-benzamide; N-[(2S,3R)-2-methyl-1-azabicyclo[2.2.2]oct-3-yl]-4-(2-methoxy-3H-imidazol-4-yloxy)-benzamide; N-[(2S,3R)-2-methyl-1-azabicyclo[2.2.2]oct-3-yl]-4-(2-trifluoromethyl-3H-imidazol-4-yloxy)-benzamide; N-[(2S,3R)-2-methyl-1-azabicyclo[2.2.2]oct-3-yl]-4-(2-acetyl-3H-imidazol-4-yloxy)-benzamide; N-[(2S,3R)-2-methyl-1-azabicyclo[2.2.2]oct-3-yl]-4-(2-acetamino-3H-imidazol-4-yloxy)-benzamide; N-[(2S,3R)-2-methyl-1-azabicyclo[2.2.2]oct-3-yl]-4-(2-cyano-3H-imidazol-4-yloxy)-benzamide; N-[(2S,3R)-2-methyl-1-azabicyclo[2.2.2]oct-3-yl]-4-(2-morpholin-4-yl-3H-imidazol-4-yloxy)-benzamide; N-[(2S,3R)-2-methyl-1-azabicyclo[2.2.2]oct-3-yl]-4-(isoxazol-2-yloxy)-benzamide; N-[(2S,3R)-2-methyl-1-azabicyclo[2.2.2]oct-3-yl]-4-(5-methylisoxazol-3-yloxy)-benzamide; N-[(2S,3R)-2-methyl-1-azabicyclo[2.2.2]oct-3-yl]-4-(5-chloroisoxazol-3-yloxy)-benzamide; N-[(2S,3R)-2-methyl-1-azabicyclo[2.2.2]oct-3-yl]-4-(5-methoxyisoxazol-3-yloxy)-benzamide; N-[(2S,3R)-2-methyl-1-azabicyclo[2.2.2]oct-3-yl]-4-(5-trifluoromethylisoxazol-3-yloxy)-benzamide; N-[(2S,3R)-2-methyl-1-azabicyclo[2.2.2]oct-3-yl]-4-(5-acetylisoxazol-3-yloxy)-benzamide; N-[(2S,3R)-2-methyl-1-azabicyclo[2.2.2]oct-3-yl]-4-(5-acetaminoisoxazol-3-yloxy)-benzamide; N-[(2S,3R)-2-methyl-1-azabicyclo[2.2.2]oct-3-yl]-4-(5-cyanoisoxazol-3-yloxy)-benzamide; N-[(2S,3R)-2-methyl-1-azabicyclo[2.2.2]oct-3-yl]-4-(5-morpholin-4-yl-isoxazol-3-yloxy)-benzamide; N-[(2S,3R)-2-methyl-1-azabicyclo[2.2.2]oct-3-yl]-4-(isothiazol-2-yloxy)-benzamide; N-[(2S,3R)-2-methyl-1-azabicyclo[2.2.2]oct-3-yl]-4-(5-methylisothiazol-3-yloxy)-benzamide; N-[(2S,3R)-2-methyl-1-azabicyclo[2.2.2]oct-3-yl]-4-(5-chloroisothiazol-3-yloxy)-benzamide; N-[(2S,3R)-2-methyl-1-azabicyclo[2.2.2]oct-3-yl]-4-(5-methoxyisothiazol-3-yloxy)-benzamide; N-[(2S,3R)-2-methyl-1-azabicyclo[2.2.2]oct-3-yl]-4-(5-trifluoromethylisothiazol-3-yloxy)-benzamide; N-[(2S,3R)-2-methyl-1-azabicyclo[2.2.2]oct-3-yl]-4-(5-acetylisothiazol-3-yloxy)-benzamide; N-[(2S,3R)-2-methyl-1-azabicyclo[2.2.2]oct-3-yl]-4-(5-acetaminoisothiazol-3-yloxy)-benzamide; N-[(2S,3R)-2-methyl-1-azabicyclo[2.2.2]oct-3-yl]-4-(5-cyanoisothiazol-3-yloxy)-benzamide; N-[(2S,3R)-2-methyl-1-azabicyclo[2.2.2]oct-3-yl]-4-(5-morpholin-4-yl-isothiazol-3-yloxy)-benzamide; N-[(2S,3R)-2-methyl-1-azabicyclo[2.2.2]oct-3-yl]-4-(pyrrol-2-ylsulfanyl)-benzamide; N-[(2S,3R)-2-methyl-1-azabicyclo[2.2.2]oct-3-yl]-4-(5-methylpyrrol-2-ylsulfanyl)-benzamide; N-[(2S,3R)-2-methyl-1-azabicyclo[2.2.2]oct-3-yl]-4-(5-chloropyrrol-2-ylsulfanyl)-benzamide; N-[(2S,3R)-2-methyl-1-azabicyclo[2.2.2]oct-3-yl]-4-(5-methoxypyrrol-2-ylsulfanyl)-benzamide; N-[(2S,3R)-2-methyl-1-azabicyclo[2.2.2]oct-3-yl]-4-(5-trifluoromethylpyrrol-2-ylsulfanyl)-benzamide; N-[(2S,3R)-2-methyl-1-azabicyclo[2.2.2]oct-3-yl]-4-(5-acetylpyrrol-2-ylsulfanyl)-benzamide; N-[(2S,3R)-2-methyl-1-azabicyclo[2.2.2]oct-3-yl]-4-(5-acetaminopyrrol-2-ylsulfanyl)-benzamide; N-[(2S,3R)-2-methyl-1-azabicyclo[2.2.2]oct-3-yl]-4-(5-cyanopyrrol-2-ylsulfanyl)-benzamide; N-[(2S,3R)-2-methyl-1-azabicyclo[2.2.2]oct-3-yl]-4-(5-morpholin-4-yl-pyrrol-2-ylsulfanyl)-benzamide; N-[(2S,3R)-2-methyl-1-azabicyclo[2.2.2]oct-3-yl]-4-(3H-imidazol-4-ylsulfanyl)-benzamide; N-[(2S,3R)-2-methyl-1-azabicyclo[2.2.2]oct-3-yl]-4-(2-methyl-3H-imidazol-4-ylsulfanyl)-benzamide; N-[(2S,3R)-2-methyl-1-azabicyclo[2.2.2]oct-3-yl]-4-(2-chloro-3H-imidazol-4-ylsulfanyl)-benzamide; N-[(2S,3R)-2-methyl-1-azabicyclo[2.2.2]oct-3-yl]-4-(2-methoxy-3H-imidazol-4-ylsulfanyl)-benzamide; N-[(2S,3R)-2-methyl-1-azabicyclo[2.2.2]oct-3-yl]-4-(2-trifluoromethyl-3H-imidazol-4-ylsulfanyl)-benzamide; N-[(2S,3R)-2-methyl-1-azabicyclo[2.2.2]oct-3-yl]-4-(2-acetyl-3H-imidazol-4-ylsulfanyl)-benzamide; N-[(2S,3R)-2-methyl-1-azabicyclo[2.2.2]oct-3-yl]-4-(2-acetamino-3H-imidazol-4-ylsulfanyl)-benzamide; N-[(2S,3R)-2-methyl-1-azabicyclo[2.2.2]oct-3-yl]-4-(2-cyano-3H-imidazol-4-ylsulfanyl)-benzamide; N-[(2S,3R)-2-methyl-1-azabicyclo[2.2.2]oct-3-yl]-4-(2-morpholin-4-yl-3H-imidazol-4-ylsulfanyl)-benzamide; N-[(2S,3R)-2-methyl-1-azabicyclo[2.2.2]oct-3-yl]-4-(isoxazol-2-ylsulfanyl)-benzamide; N-[(2S,3R)-2-methyl-1-azabicyclo[2.2.2]oct-3-yl]-4-(5-methylisoxazol-3-ylsulfanyl)-benzamide; N-[(2S,3R)-2-methyl-1-azabicyclo[2.2.2]oct-3-yl]-4-(5-chloroisoxazol-3-ylsulfanyl)-benzamide; N-[(2S,3R)-2-methyl-1-azabicyclo[2.2.2]oct-3-yl]-4-(5-methoxyisoxazol-3-ylsulfanyl)-benzamide; N-[(2S,3R)-2-methyl-1-azabicyclo[2.2.2]oct-3-yl]-4-(5-trifluoromethylisoxazol-3-ylsulfanyl)-benzamide; N-[(2S,3R)-2-methyl-1-azabicyclo[2.2.2]oct-3-yl]-4-(5-acetylisoxazol-3-ylsulfanyl)-benzamide; N-[(2S,3R)-2-methyl-1-azabicyclo[2.2.2]oct-3-yl]-4-(5-acetaminoisoxazol-3-ylsulfanyl)-benzamide; N-[(2S,3R)-2-methyl-1-azabicyclo[2.2.2]oct-3-yl]-4-(5-cyanoisoxazol-3-ylsulfanyl)-benzamide; N-[(2S,3R)-2-methyl-1-azabicyclo[2.2.2]oct-3-yl]-4-(5-morpholin-4-yl-isoxazol-3-ylsulfanyl)-benzamide; N-[(2S,3R)-2-methyl-1-azabicyclo[2.2.2]oct-3-yl]-4-(isothiazol-2-ylsulfanyl)-benzamide; N-[(2S,3R)-2-methyl-1-azabicyclo[2.2.2]oct-3-yl]-4-(5-methylisothiazol-3-ylsulfanyl)-benzamide; N-[(2S,3R)-2-methyl-1-azabicyclo[2.2.2]oct-3-yl]-4-(5-chloroisothiazol-3-ylsulfanyl)-benzamide; N-[(2S,3R)-2-methyl-1-azabicyclo[2.2.2]oct-3-yl]-4-(5-methoxyisothiazol-3-ylsulfanyl)-benzamide; N-[(2S,3R)-2-methyl-1-azabicyclo[2.2.2]oct-3-yl]-4-(5-trifluoromethylisothiazol-3-ylsulfanyl)-benzamide; N-[(2S,3R)-2-methyl-1-azabicyclo[2.2.2]oct-3-yl]-4-(5-acetylisothiazol-3-ylsulfanyl)-benzamide; N-[(2S,3R)-2-methyl-1-azabicyclo[2.2.2]oct-3-yl]-4-(5-acetaminoisothiazol-3-ylsulfanyl)-benzamide; N-[(2S,3R)-2-methyl-1-azabicyclo[2.2.2]oct-3-yl]-4-(5-cyanoisothiazol-3-ylsulfanyl)-benzamide; N-[(2S,3R)-2-methyl-1-azabicyclo[2.2.2]oct-3-yl]-4-(5-morpholin-4-yl-isothiazol-3-ylsulfanyl)-benzamide; N-[(2S,3R)-2-methyl-1-azabicyclo[2.2.2]oct-3-yl]-4-(6-methylpyridin-3-yloxy)-benzamide; N-[(2S,3R)-2-methyl-1-azabicyclo[2.2.2]oct-3-yl]-4-(6-chloropyridin-3-yloxy)-benzamide ; N-[(2S,3R)-2-methyl-1-azabicyclo[2.2.2]oct-3-yl]-4-(6-methoxypyridin-3-yloxy)-benzamide; N-[(2S,3R)-2-methyl-1-azabicyclo[2.2.2]oct-3-yl]-4-(6-trifluoromethylpyridin-3-yloxy)-benzam ide; N-[(2S,3R)-2-methy-1-azabicyclo[2.2.2]oct-3-yl]-4-(6-acetylpyridin-3-yloxy)-benzamide; N-[(2S,3R)-2-methyl-1-azabicyclo[2.2.2]oct-3-yl]-4-(6-acetaminopyridin-3-yloxy)-benzamide; N-[(2S,3R)-2-methyl-1-azabicyclo[2.2.2]oct-3-yl]-4-(6-cyanopyridin-3-yloxy)-benzamide; N-[(2S,3R)-2-methyl-1-azabicyclo[2.2.2]oct-3-yl]-4-(6-morpholin-4-yl-pyridin-3-yloxy)-benzamide; N-[(2S,3R)-2-methyl-1-azabicyclo[2.2.2]oct-3-yl]-4-(2methylpyridin-4-yloxy)-benzamide; N-[(2S,3R)-2-methyl-1-azabicyclo[2.2.2]oct-3-yl]-4-(2-chloropyridin-4-yloxy)-benzamide; N-[(2S,3R)-2-methyl-1-azabicyclo[2.2.2]oct-3-yl]-4-(2-methoxypyridin-4-yloxy)- benzamide; N-[(2S,3R)-2-methyl-1-azabicyclo[2.2.2]oct-3-yl]-4-(2-trifluoromethylpyridin-4-yloxy)-benzamide; N-[(2S,3R)-2-methyl-1-azabicyclo[2.2.2]oct-3-yl]-4-(2-acetylpyridin-4-yloxy)-benzamide; N-[(2S,3R)-2-methyl-1-azabicyclo[2.2.2]oct-3-yl]-4-(2-acetaminopyridin-4-yloxy)-benzamide; N-[(2S,3R)-2-methyl-1-azabicyclo[2.2.2]oct-3-yl]-4-(2cyanopyridin-4-yloxy)-benzamide; N-[(2S,3R)-2-methyl-1-azabicyclo[2.2.2]oct-3-yl]-4-(2-morpholin-4-yl-pyridin-4-yloxy)-benzamide; N-[(2S,3R)-2-methyl-1-azabicyclo[2.2.2]oct-3-yl]-4-(5-methylpyridin-2-yloxy)-benzamide; N-[(2S,3R)-2-methyl-1-azabicyclo[2.2.2]oct-3-yl]-4-(5-chloropyridin-2-yloxy)-benzamide; N-[(2S,3R)-2-methyl-1-azabicyclo[2.2.2]oct-3-yl]-4-(5-methoxypyridin-2-yloxy)-benzamide; N-[(2S,3R)-2-methyl-1-azabicyclo[2.2.2]oct-3-yl]-4-(5-trifluoromethylpyridin-2-yloxy)-benzamide; N-[(2S,3R)-2-methyl-1-azabicyclo[2.2.2]oct-3-yl]-4-(5-acetylpyridin-2-yloxy)-benzamide; N-[(2S,3R)-2-methyl-1-azabicyclo[2.2.2]oct-3-yl]-4-(5-acetaminopyridin-2-yloxy)-benzamide; N-[(2S,3R)-2-methyl-1-azabicyclo[2.2.2]oct-3-yl]-4-(5-cyanopyridin-2-yloxy)-benzamide; N-[(2S,3R)-2-methyl-1-azabicyclo[2.2.2]oct-3-yl]-4-(5-morpholin-4-yl-pyridin-2-yloxy)-benzamide; N-[(2S,3R)-2-methyl-1-azabicyclo[2.2.2]oct-3-yl]-4-(4-methylpyridin-2-yloxy)-benzamide; N-[(2S,3R)-2-methyl-1-azabicyclo[2.2.2]oct-3-yl]-4-(4-chloropyridin-2-yloxy)-benzamide; N-[(2S,3R)-2-methyl-1-azabicyclo[2.2.2]oct-3-yl]-4-(4-methoxypyridin-2-yloxy)-benzamide; N-[(2S,3R)-2-methyl-1-azabicyclo[2.2.2]oct-3-yl]-4-(4-trifluoromethylpyridin-2-yloxy)-benzamide; N-[(2S,3R)-2-methyl-1-azabicyclo[2.2.2]oct-3-yl]-4-(4-acetylpyridin-2-yloxy)-benzamide; N-[(2S,3R)-2-methyl-1-azabicyclo[2.2.2]oct-3-yl]-4-(4-acetaminopyridin-2-yloxy)-benzamide; N-[(2S,3R)-2-methyl-1-azabicyclo[2.2.2]oct-3-yl]-4-(4-cyanopyridin-2-yloxy)-benzamide; N-[(2S,3R)-2-methyl-1-azabicyclo[2.2.2]oct-3-yl]-4-(4-morpholin-4-yl-pyridin-2-yloxy)-benzamide; N-[(2S,3R)-2-methyl-1-azabicyclo[2.2.2]oct-3-yl]-4-(6-methylpyridin-2-yloxy)-benzamide; N-[(2S,3R)-2-methyl-1-azabicyclo[2.2.2]oct-3-yl]-4-(6-chloropyridin-2-yloxy)-benzamide; N-[(2S,3R)-2-methyl-1-azabicyclo[2.2.2]oct-3-yl]-4-(6-methoxypyridin-2-yloxy)-benzamide; N-[(2S,3R)-2-methyl-1-azabicyclo[2.2.2]oct-3-yl]-4-(6-trifluoromethylpyridin-2-yloxy)-benzamide; N-[(2S,3R)-2-methyl-1-azabicyclo[2.2.2]oct-3-yl]-4-(6-acetylpyridin-2-yloxy)-benzamide; N-[(2S,3R)-2-methyl-1-azabicyclo[2.2.2]oct-3-yl]-4-(6-acetaminopyridin-2-yloxy)-benzamide; N-[(2S,3R)-2-methyl-1-azabicyclo[2.2.2]oct-3-yl]-4-(6-cyanopyridin-2-yloxy)-benzamide; N-[(2S,3R)-2-methyl-1-azabicyclo[2.2.2]oct-3-yl]-4-(6-morpholin-4-yl-pyridin-2-yloxy)-benzamide; N-[(2S,3R)-2-methyl-1-azabicyclo[2.2.2]oct-3yl]-4-(5-methylpyridin-3-yloxy)-benzamide; N-[(2S,3R)-2-methyl-1-azabicyclo[2.2.2]oct-3-yl]-4-(5-chloropyridin-3-yloxy)-benzamide; N-[(2S,3R)-2-methyl-1-azabicyclo[2.2.2]oct-3-yl]-4-(5-methoxypyridin-3-yloxy)-benzamide; N-[(2S,3R)-2-methyl-1-azabicyclo[2.2.2]oct-3-yl]-4-(5-trifluoromethylpyridin-3-yloxy)-benzamide; N-[(2S,3R)-2-methyl-1-azabicyclo[2.2.2]oct-3-yl]-4-(5-acetylpyridin-3-yloxy)-benzamide; N-[(2S,3R)-2-methyl-1-azabicyclo[2.2.2]oct-3-yl]-4-(5-acetaninopyridin-3-yloxy)-benzamide; N-[(2S,3R)-2-methyl-1-azabicyclo[2.2.2]oct-3-yl]-4-(5-cyanopyridin-3-yloxy)-benzamide; N-[(2S,3R)-2-methyl-1-azabicyclo[2.2.2]oct-3-yl]-4-(5-morpholin-4-yl-pyridin-3-yloxy)-benzamide; N-[(2S,3R)-2-methyl-1-azabicyclo[2.2.2]oct-3-yl]-4-(2-chloropyridin-3-yloxy)-benzamide; N-[(2S,3R)-2-methyl-1-azabicyclo[2.2.2]oct-3-yl]-4-(4-chloropyridin-3-yloxy)-benzamide; N-[(2S,3R)-2-methyl-1-azabicyclo[2.2.2]oct-3-yl]-4-(3-chloropyridin-4-yloxy)-benzamide; N-[(2S,3R)-2-methyl-1-azabicyclo[2.2.2]oct-3-yl]-4-(3-chloropyridin-2-yloxy)-benzamide; N-[(2S,3R)-2-methyl-1-azabicyclo[2.2.2]oct-3-yl]-4-(6-methylpyridin-3-ylsulfanyl)-benzamide; N-[(2S,3R)-2-methyl-1-azabicyclo[2.2.2]oct-3-yl]-4-(6-chloropyridin-3-ylsulfanyl)-benzamide; N-[(2S,3R)-2-methyl-1-azabicyclo[2.2.2]oct-3-yl]-4-(6-methoxypyridin-3-ylsulfanyl)-benzamide; N-[(2S,3R)-2-methyl-1-azabicyclo[2.2.2]oct-3-yl]-4-(6-trifluoromethylpyridin-3-ylsulfanyl)-benzamide; N-[(2S,3R)-2-methyl-1-azabicyclo[2.2.2]oct-3-yl]-4-(6-acetylpyridin-3-ylsulfanyl)-benzamide; N-[(2S,3R)-2-methyl-1-azabicyclo[2.2.2]oct-3-yl]-4-(6-acetaminopyridin-3-ylsulfanyl)-benzamide; N-[(2S,3R)-2-methyl-1-azabicyclo[2.2.2]oct-3-yl]-4-(6-cyanopyridin-3-ylsulfanyl)-benzamide; N-[(2S,3R)-2-methyl-1-azabicyclo[2.2.2]oct-3-yl]-4-(6-morpholin-4-yl-pyridin-3-ylsulfanyl)-benzamide; N-[(2S,3R)-2-methyl-1-azabicyclo[2.2.2]oct-3-yl]-4-(2-methylpyridin-4-ylsulfanyl)-benzamide; N-[(2S,3R)-2-methyl-1-azabicyclo[2.2.2]oct-3-yl]-4-(2-chloropyridin-4-ylsulfanyl)-benzamide; N-[(2S,3R)-2-methyl-1-azabicyclo[2.2.2]oct-3-yl]-4-(2-methoxypyridin-4-ylsulfanyl)-benzamide; N-[(2S,3R)-2-methyl-1-azabicyclo[2.2.2]oct-3-yl]-4-(2-trifluoromethylpyridin-4-ylsulfanyl)-benzamide; N-[(2S,3R)-2-methyl-1-azabicyclo[2.2.2]oct-3-yl]-4-(2-acetylpyridin-4-ylsulfanyl)-benzamide; N-[(2S,3R)-2-methyl-1-azabicyclo[2.2.2]oct-3-yl]-4-(2-acetaminopyridin-4-ylsulfanyl)-benzamide; N-[(2S,3R)-2-methyl-1-azabicyclo[2.2.2]oct-3-yl]-4-(2-cyanopyridin-4-ylsulfanyl)-benzamide; N-[(2S,3R)-2-methyl-1-azabicyclo[2.2.2]oct-3-yl]-4-(2-morpholin-4-yl-pyridin-4-ylsulfanyl)-benzamide; N-[(2S,3R)-2-methyl-1-azabicyclo[2.2.2]oct-3-yl]-4-(5-methylpyridin-2-ylsulfanyl)-benzamide; N-[(2S,3R)-2-methyl-1-azabicyclo[2.2.2]oct-3-yl]-4-(5-chloropyridin-2-ylsulfanyl)-benzamide; N-[(2S,3R)-2-methyl-1-azabicyclo[2.2.2]oct-3-yl]-4-(5-methoxypyridin-2-ylsulfanyl)-benzamide; N-[(2S,3R)-2-methyl-1-azabicyclo[2.2.2]oct-3-yl]-4-(5-trifluoromethylpyridin-2-ylsulfanyl)-benzamide; N-[(2S,3R)-2-methyl-1-azabicyclo[2.2.2]oct-3-yl]-4-(5-acetylpyridin-2-ylsulfanyl)-benzamide; N-[(2S,3R)-2-methyl-1-azabicyclo[2.2.2]oct-3-yl]-4-(5-acetaminopyridin-2-ylsulfanyl)-benzamide; N-[(2S,3R)-2-methyl-1-azabicyclo[2.2.2]oct-3-yl]-4-(5-cyanopyridin-2-ylsulfanyl)-benzamide; N-[(2S,3R)-2-methyl-1-azabicyclo[2.2.2]oct-3-yl]-4-(5-morpholin-4-yl-pyridin-2-ylsulfanyl)-benzamide; N-[(2S,3R)-2-methyl-1-azabicyclo[2.2.2]oct-3-yl]-4-(4-methylpyridin-2-ylsulfanyl)-benzamide; N-[(2S,3R)-2-methyl-1-azabicyclo[2.2.2]oct-3-yl]-4-(4-chloropyridin-2-ylsulfanyl)-benzamide; N-[(2S,3R)-2-methyl-1-azabicyclo[2.2.2]oct-3-yl]-4-(4-methoxypyridin-2-ylsulfanyl)-benzamide; N-[(2S,3R)-2-methyl-1-azabicyclo[2.2.2]oct-3-yl]-4-(4-trifluoromethylpyridin-2-ylsulfanyl)-benzamide; N-[(2S,3R)-2-methyl-1-azabicyclo[2.2.2]oct-3-yl]-4-(4-acetylpyridin-2-ylsulfanyl)-benzamide; N-[(2S,3R)-2-methyl-1-azabicyclo[2.2.2]oct-3-yl]-4-(4-acetaminopyridin-2-ylsulfanyl)-benzamide; N-[(2S,3R)-2-methyl-1-azabicyclo[2.2.2]oct-3-yl]-4-(4-cyanopyridin-2-ylsulfanyl)-benzamide; N-[(2S,3R)-2-methyl-1- azabicyclo[2.2.2]oct-3-yl]-4-(4-morpholin-4-yl-pyridin-2-ylsulfanyl)-benzamide; N-[(2S,3R)-2-methyl-1-azabicyclo[2.2.2]oct-3-yl]-4-(6methylpyridin-2-ylsulfanyl)-benzamide; N-[(2S,3R)-2-methyl-1-azabicyclo[2.2.2]oct-3-yl]-4-(6-chloropyridin-2-ylsulfanyl)-benzamide; N-[(2S,3R)-2-methyl-1-azabicyclo[2.2.2]oct-3-yl]-4-(6-methoxypyridin-2-ylsulfanyl)-benzamide; N-[(2S,3R)-2-methyl-1-azabicyclo[2.2.2]oct-3-yl]-4-(6-trifluoromethylpyridin-2-ylsulfanyl)-benzamide; N-[(2S,3R)-2-methyl-1-azabicyclo[2.2.2]oct-3-yl]-4-(6-acetylpyridin-2-ylsulfanyl)-benzamide; N-[(2S,3R)-2-methyl-1-azabicyclo[2.2.2]oct-3-yl]-4-(6-acetaminopyridin-2-ylsulfanyl)-benzamide; N-[(2S,3R)-2-methyl-1-azabicyclo[2.2.2]oct-3-yl]-4-(6-cyanopyridin-2-ylsulfanyl)-benzamide; N-[(2S,3R)-2-methyl-1-azabicyclo[2.2.2]oct-3-yl]-4-(6-morpholin-4-yl-pyridin-2-ysulfanyl)-benzamide; N-[(2S,3R)-2-methyl-1-azabicyclo[2.2.2]oct-3-yl]-4-(5-methylpyridin-3-ylsulfanyl)-benzamide; N-[(2S,3R)-2-methyl-1-azabicyclo[2.2.2]oct-3-yl]-4-(5-chloropyridin-3-ylsulfanyl)-benzamide; N-[(2S,3R)-2-methyl-1-azabicyclo[2.2.2]oct-3-yl]-4-(5-methoxypyridin-3-ylsulfanyl)-benzamide; N-[(2S,3R)-2-methyl-1-azabicyclo[2.2.2]oct-3-yl]-4-(5-trifluoromethylpyridin-3-ylsulfanyl)-benzamide; N-[(2S,3R)-2-methyl-1-azabicyclo[2.2.2]oct-3-yl]-4-(5-acetylpyridin-3-ylsulfanyl)-benzamide; N-[(2S,3R)-2-methyl-1-azabicyclo[2.2.2]oct-3-yl]-4-(5-acetaminopyridin-3-ylsulfanyl)-benzamide; N-[(2S,3R)-2-methyl-1-azabicyclo[2.2.2]oct-3-yl]-4-(5-cyanopyridin-3-ylsulfanyl)-benzamide; N-[(2S,3R)-2-methyl-1-azabicyclo[2.2.2]oct-3-yl]-4-(5-morpholin-4-yl-pyridin-3-ylsulfanyl)-benzamide; N-[(2S,3R)-2-methyl-1-azabicyclo[2.2.2]oct-3-yl]-4-(2-chloropyridin-3-ylsulfanyl)-benzamide; N-[(2S,3R)-2-methyl-1-azabicyclo[2.2.2]oct-3-yl]-4-(4-chloropyridin-3-ylsulfanyl)-benzamide; N-[(2S,3R)-2-methyl-1-azabicyclo[2.2.2]oct-3-yl]-4-(3-chloropyridin-4-ylsulfanyl)-benzamide; N-[(2S,3R)-2-methyl-1-azabicyclo[2.2.2]oct-3-yl]-4-(3-chloropyridin-2-ylsulfanyl)-benzamide; or pharmaceutically acceptable salts thereof.

Materials and Methods for identifying binding constants:

Membrane Preparation. Male Sprague-Dawley rats (300–350 g) are sacrificed by decapitation and the brains (whole brain minus cerebellum) are dissected quickly, weighed and homogenized in 9 volumes/g wet weight of ice-cold 0.32 M sucrose using a rotating pestle on setting 50 (10 up and down strokes). The homogenate is centrifuged at 1,000×g for 10 minutes at 4° C. The supernatant is collected and centrifuged at 20,000×g for 20 minutes at 4° C. The resulting pellet is resuspended to a protein concentration of 1–8 mg/mL. Aliquots of 5 mL homogenate are frozen at −80° C. until needed for the assay. On the day of the assay, aliquots are thawed at room temperature and diluted with Kreb's–20 mM Hepes buffer pH 7.0 (at room temperature) containing 4.16 mM $NaHCO_3$, 0.44 mM $KH_2PO_4$, 127 mM NaCl, 5.36 mM KCl, 1.26 mM $CaCl_2$, and 0.98 mM $MgCl_2$, so that 25–150 μg protein are added per test tube. Proteins are determined by the Bradford method (Bradford, M. M., *Anal. Biochem.*, 72, 248–254, 1976) using bovine serum albumin as the standard.

Binding Assay. For saturation studies, 0.4 mL homogenate are added to test tubes containing buffer and various concentrations of radioligand, and are incubated in a final volume of 0.5 mL for 1 hour at 25° C. Nonspecific binding was determined in tissues incubated in parallel in the presence of 0.05 ml MLA for a final concentration of 1 μM MLA, added before the radioligand. In competition studies, drugs are added in increasing concentrations to the test tubes before addition of 0.05 ml [$^3$H]-MLA for a final concentration of 3.0 to 4.0 nM [$^3$H]-MLA. The incubations are terminated by rapid vacuum filtration through Whatman GF/B glass filter paper mounted on a 48 well Brandel cell harvester. Filters are pre-soaked in 50 mM Tris HCl pH 7.0–0.05% polyethylenimine. The filters are rapidly washed two times with 5 mL aliquots of cold 0.9% saline and then counted for radioactivity by liquid scintillation spectrometry.

Data Analysis. In competition binding studies, the inhibition constant (Ki) was calculated from the concentration dependent inhibition of [$^3$H]-MLA binding obtained from non-linear regression fitting program according to the Cheng-Prusoff equation (Cheng, Y. C. and Prussoff, W. H., *Biochem. Pharmacol.*, 22, p. 3099–3108, 1973). Hill coefficients were obtained using non-linear regression (GraphPad Prism sigmoidal dose-response with variable slope).

The aforementioned examples have the provided Ki values:

| Example # | Ki (nM) |
| --- | --- |
| 1 | 278 |
| 2 | 270 |
| 3 | 847 |
| 5 | 98 |
| 7 | 1577 |
| 8 | 910 |
| 12 | 1592 |
| 13 | 1240 |
| 15 | 835 |
| 16 | 414 |
| 17 | 170 |
| 23 | 1655–1980 |

What is claimed:
1. Compounds of the Formula I:

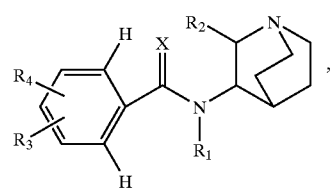

Formula I or pharmaceutically acceptable salts thereof, wherein

X is O or S;

$R_1$ is independently selected from the group consisting of —H, alkyl, cycloalkyl, halogenated alkyl, and aryl;

Alkyl is both straight- and branched-chain moieties having from 1–6 carbon atoms;

Halogenated alkyl is an alkyl moiety having from 1–6 carbon atoms and having 1 to (2n+1) substituent(s) independently selected from —F, —Cl, —Br, or —I where n is the maximum number of carbon atoms in the moiety;

Cycloalkyl is a cyclic alkyl moiety having from 3–6 carbon atoms;

Aryl is phenyl, substituted phenyl, naphthyl, or substituted naphthyl;

Substituted phenyl is a phenyl either having 1–4 substituents independently selected from —F, —Cl, —Br, or —I, or having 1 substituent selected from —$R_{12}$ and 0–3 substituents independently selected from —F, —Cl, —Br, or —I;

Substituted naphthyl is a naphthalene moiety either having 1–4 substituents independently selected from —F, —Cl, —Br, or —I, or having 1 substituent selected from —$R_{12}$ and 0–3 substituents independently selected from —F, —Cl, —Br, or —I, where the substitution can be independently on either only one ring or both rings of said naphthalene moiety;

$R_2$ is —H, alkyl, halogenated alkyl, substituted alkyl, cycloalkyl, benzyl, substituted benzyl, or aryl;

Substituted alkyl is an alkyl moiety from 1–6 carbon atoms and having 0–3 substituents independently selected from —F, —Cl, —Br, or —I and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$S(O)_2NR_{10}R_{10}$, —$NR_{10}S(O)_2R_{10}$, —$NO_2$, —$R_7$, —$R_9$, phenyl, or substituted phenyl;

Substituted benzyl is a benzyl either having 1–4 substituents independently selected from —F, —Cl, —Br, or —I, or having 1 substituent selected from —$R_{12}$ and 0–3 substituents independently selected from —F, —Cl, —Br, or —I, provided that all substitution is on the phenyl ring of the benzyl;

$R_3$ is selected from the group consisting of —H, alkyl, alkenyl, alkynyl, cycloalkyl, heterocycloalkyl, halogenated alkyl, halogenated alkenyl, halogenated alkynyl, halogenated cycloalkyl, halogenated heterocycloalkyl, substituted alkyl, substituted alkenyl, substituted alkynyl, substituted cycloalkyl, substituted heterocycloalkyl, aryl, —$R_7$, —$R_9$, —$OR_8$, —$SR_8$, —F, —Cl, —Br, —I, —$NR_8R_8$, —$C(O)R_8$, —CN, —$C(O)NR_8R_8$, —$NR_8C(O)R_8$, —$S(O)R_8$, —$OS(O)_2R_8$, —$NR_8S(O)_2R_8$, —$NO_2$, and —$N(H)C(O)N(H)R_8$;

Alkenyl is straight- and branched-chain moieties having from 2–6 carbon atoms and having at least one carbon-carbon double bond;

Halogenated alkenyl is an unsaturated alkenyl moiety having from 2–6 carbon atoms and having 1 to (2n–1) substituent(s) independently selected from —F, —Cl, —Br, or —I where n is the maximum number of carbon atoms in the moiety;

Substituted alkenyl is an unsaturated alkenyl moiety having from 2–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —$NR_{10}C(O)R_{10}$, —$S(O)_2NR_{10}R_{10}$, —$NR_{10}S(O)_2R_{10}$, —CN, phenyl, or substituted phenyl;

Alkynyl is straight- and branched-chained moieties having from 2–6 carbon atoms and having at least one carbon-carbon triple bond;

Halogenated alkynyl is an unsaturated alkynyl moiety having from 3–6 carbon atoms and having 1 to (2n–3) substituent(s) independently selected from —F, —Cl, —Br, or —I where n is the maximum number of carbon atoms in the moiety;

Substituted alkynyl is an unsaturated alkynyl moiety having from 3–6 carbon atoms and having 0–3 substituents independently selected from —F, or —Cl, and further having 1 substituent selected from —$R_7$, —$R_9$, —$OR_{10}$, —$SR_{10}$, —$NR_{10}R_{10}$, —$C(O)R_{10}$, —$C(O)NR_{10}R_{10}$, —$NR_{10}C(O)R_{10}$, —$S(O)_2NR_{10}R_{10}$, —$NR_{10}S(O)_2R_{10}$, —CN, phenyl, or substituted phenyl;

Halogenated cycloalkyl is a cyclic moiety having from 3–6 carbon atoms and having 1–4 substituents independently selected from —F, or —Cl;

Substituted cycloalkyl is a cyclic moiety having from 3–6 carbon atoms and having 0–3 substituents independently selected from —F, or —Cl, and further having 1 substituent selected from —$OR_{10}$, —$SR_{10}$, —$NR_{10}R_{10}$, —$C(O)R_{10}$, —CN, —$C(O)NR_{10}R_{10}$, —$NR_{10}C(O)R_{10}$, —$S(O)_2NR_{10}R_{10}$, —$NR_{10}S(O)_2R_{10}$, —$NO_2$, phenyl, or substituted phenyl;

Heterocycloalkyl is a cyclic moiety having 4–7 atoms with 1–2 atoms within the ring being —S—, —$N(R_3)$—, or —O—;

Halogenated heterocycloalkyl is a cyclic moiety having from 4–7 atoms with 1–2 atoms within the ring being —S—, —$N(R_3)$—, or —O—, and having 1–4 substituents independently selected from —F, or —Cl;

Substituted heterocycloalkyl is a cyclic moiety having from 4–7 atoms with 1–2 atoms within the ring being —S—, —$N(R_3)$—, or —O— and having 0–3 substituents independently selected from —F, or —Cl, and further having 1 substituent selected from —$OR_{10}$, —$SR_{10}$, —$NR_{10}R_{10}$, —$C(O)R_{10}$, —$C(O)NR_{10}R_{10}$, —CN, —$NR_{10}C(O)R_{10}$, —$NO_2$, —$S(O)_2NR_{10}R_{10}$, —$NR_{10}S(O)_2R_{10}$, phenyl, or substituted phenyl;

$R_4$ is selected from the group consisting of —O—$R_5$, —S—$R_5$, —S(O)—$R_5$, —C(O)—$R_5$, and alkyl substituted on the ω carbon with $R_5$ where said ω carbon is determined by counting the longest carbon chain of the alkyl moiety with the C-1 carbon being the carbon attached to the phenyl ring of the core molecule and the ω carbon being the carbon furthest from said C-1 carbon;

$R_5$ is selected from aryl, $R_7$, or $R_9$;

$R_7$ is 5-membered heteroaromatic mono-cyclic moieties containing within the ring 1–3 heteroatoms independently selected from the group consisting of —O—, =N—, —$N(R_{14})$—, and —S—, and having 0–1 substituent selected from —$R_{12}$ and 0–3 substituents independently selected from —F, —Cl, —Br, or —I, or $R_7$ is a 9-membered fused-ring moiety having a 6-membered ring fused to a 5-membered ring and having the formula

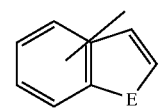

wherein E is O, S, or $NR_{14}$,

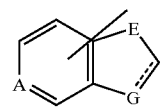

wherein E and G are independently selected from $CR_{18}$, O, S, or $NR_{14}$, and A is $CR_{18}$ or N, or

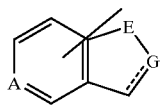

wherein E and G are independently selected from $CR_{18}$, O, S, or $NR_{14}$, and A is $CR_{18}$ or N, each 9-membered fused-ring moiety having 0–1 substituent selected from —$R_{12}$ and 0–3 substituent(s) independently selected from —F, —Cl, —Br, or —I, and having a bond directly or indirectly attached to the core molecule where valency allows in either the 6-membered or the 5-membered ring of the fused-ring moiety;

Each $R_8$ is independently selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_9$ is 6-membered heteroaromatic mono-cyclic moieties containing within the ring 1–3 heteroatoms selected from =N— and having 0–1 substituent selected from —$R_{12}$ and 0–3 substituent(s) independently selected from —F, —Cl, —Br, or —I, or 10-membered heteroaromatic bi-cyclic moieties containing within one or both rings 1–3 heteroatoms selected from =N—, including quinolinyl or isoquinolinyl, each 10-membered fused-ring moiety having 0–1 substituent selected from —$R_{12}$ and 0–3 substituent(s) independently selected from —F, —Cl, —Br, or —I and having a bond directly or indirectly attached to the core molecule where valency allows;

Each $R_{10}$ is independently selected from —H, alkyl, cycloalkyl, heterocycloalkyl, alkyl substituted with 1 substituent selected from $R_{13}$, cycloalkyl substituted with 1 substituent selected from $R_{13}$, heterocycloalkyl substituted with 1 substituent selected from $R_3$, halogenated alkyl, halogenated cycloalkyl, halogenated heterocycloalkyl, phenyl, or substituted phenyl;

Each $R_{11}$ is independently selected from —H, alkyl, cycloalkyl, heterocycloalkyl, halogenated alkyl, halogenated cycloalkyl, or halogenated heterocycloalkyl;

$R_{12}$ is selected from —$OR_{11}$, —$SR_{11}$, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$;

$R_{13}$ is selected from —$OR_{11}$, —$SR_{11}$, —$NR_{11}R_{11}$, —$C(O)R_{11}$, —$C(O)NR_{11}R_{11}$, —CN, —$CF_3$, —$NR_{11}C(O)R_{11}$, —$S(O)_2NR_{11}R_{11}$, —$NR_{11}S(O)_2R_{11}$, or —$NO_2$;

$R_{14}$ is selected from —H, alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, phenyl, or substituted phenyl;

Each $R_{15}$ is independently selected from alkyl, halogenated alkyl, substituted alkyl, cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

Each $R_{16}$ is independently selected from cycloalkyl, halogenated cycloalkyl, substituted cycloalkyl, heterocycloalkyl, halogenated heterocycloalkyl, substituted heterocycloalkyl, $R_7$, $R_9$, phenyl, or substituted phenyl;

$R_{17}$ is selected from cycloalkyl, halogenated cycloalkyl, substituted cycloalkyl, heterocycloalkyl, halogenated heterocycloalkyl, or substituted heterocycloalkyl; and Each $R_{18}$ is independently selected from —H, alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, —F, —Cl, —Br, or —I, or a bond directly or indirectly attached to the core molecule, provided that there is only one said bond to the core molecule within the 9-membered fused-ring moiety, further provided that the fused-ring moiety has 0–1 substituent selected from alkyl, cycloalkyl, heterocycloalkyl, halogenated alkyl, halogenated cycloalkyl, halogenated heterocycloalkyl, substituted alkyl, substituted cycloalkyl, substituted heterocycloalkyl, —$OR_{11}$, —$SR_{11}$, —$NR_{11}R_{11}$, —$C(O)R_{11}$, —$NO_2$, —$C(O)NR_{11}R_{11}$, —CN, —$NR_{11}C(O)R_{11}$, —$S(O)_2NR_{11}R_{11}$, or —$NR_{11}S(O)_2R_{11}$, and further provided that the fused-ring ring moiety has 0–3 substituent(s) selected from —F, —Cl, —Br, or —I.

2. The compounds according to claim 1, wherein X is O.

3. The compounds according to claim 2, wherein $R_2$ is one of alkyl, halogenated alkyl, substituted alkyl, cycloalkyl, benzyl, substituted benzyl, or aryl.

4. The compounds according to claim 2, wherein $R_1$ and $R_2$ are both H.

5. The compounds according to claim 4 wherein $R_3$ is selected from the group consisting of alkenyl, alkynyl, cycloalkyl, heterocycloalkyl, halogenated alkenyl, halogenated alkynyl, halogenated cycloalkyl, halogenated heterocycloalkyl, substituted alkenyl, substituted alkynyl, substituted cycloalkyl, substituted heterocycloalkyl, aryl, —$R_7$, —$R_9$, —$OR_{17}$, —$SR_8$, —$NR_{16}R_{16}$, —$C(O)R_{16}$, —CN, —$C(O)NR_{15}R_{15}$, —$NR_8C(O)R_8$, —$S(O)R_8$, —$OS(O)_2R_8$, —$NR_8S(O)_2R_8$, —$NO_2$, and —$N(H)C(O)N(H)R_8$.

6. The compounds according to claim 4, wherein $R^4$ is —O—$R_5$.

7. The compounds according to claim 4, wherein $R_4$ is —S—$R_5$.

8. The compounds according to claim 4, wherein $R^4$ is —S(O)—$R_5$.

9. The compounds according to claim 4, wherein $R^4$ is —C(O)—$R_5$.

10. The compounds according to claim 4, wherein $R_4$ is alkyl substituted on the ω carbon with $R_5$.

11. The compounds according to claim 1, wherein the compounds are the R stereoisomer at the C3 position of the quinuclidine of Formula I:

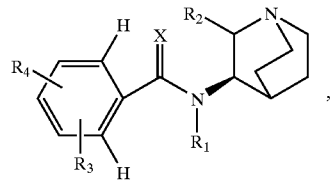

or a pharmaceutically acceptable salts thereof.

12. The compounds according to claim 11 wherein X is O.

13. The compounds according to claim 12, wherein $R_2$ is alkyl, halogenated alkyl, substituted alkyl, cycloalkyl, benzyl, substituted benzyl, or aryl.

14. The compounds according to claim 13, wherein $R_2$ is alkyl, cycloalkyl, or aryl.

15. The compounds according to claim 12, wherein $R_1$ and $R_2$ are both H.

16. The compounds according to claim 15, wherein $R_4$ is —O—$R_5$.

17. The compounds according to claim 15, wherein $R_4$ is —S—$R_5$.

18. The compounds according to claim 15, wherein $R^4$ is —S(O)—$R_5$.

19. The compounds according to claim 15, wherein $R^4$ is —C(O)—$R_5$.

20. The compounds according to claim 15, wherein $R^4$ is alkyl substituted on the ω carbon with $R_5$.

21. The compounds according to claim 15, wherein $R^4$ is located at the C4 position of the phenyl ring.

22. The compounds according to claim 21, wherein $R^4$ is —O—$R_5$.

23. The compounds according to claim 21, wherein $R^4$ is —S—$R_5$.

24. The compounds according to claim 21, wherein $R^4$ is —S(O)—$R_5$.

25. The compounds according to claim 21, wherein $R^4$ is —C(O)—$R_5$.

26. The compounds according to claim 21, wherein $R^4$ is alkyl substituted on the ω carbon with $R_5$.

27. The compounds according to claim 11, wherein the compounds are selected from the group consisting of:

N-[(3R)-1-azabicyclo[2.2.2]oct-3-yl]-4-(4-hydroxyphenoxy)benzamide;
N-[(3R)-1-azabicyclo[2.2.2]oct-3-yl]-4-(4-acetamidophenoxy)benzamide;
N-[(3R)-1-azabicyclo[2.2.2]oct-3-yl]-4-phenoxybenzamide;
N-[(3R)-1-azabicyclo[2.2.2]oct-3-yl]-4-benzylbenzamide;
N-[(3R)-1-azabicyclo[2.2.2]oct-3-yl]-4-(phenylsulfanyl)benzamide;
N-[(3R)-1-azabicyclo[2.2.2]oct-3-yl]-3-phenoxybenzamide;
N-[(3R)-1-azabicyclo[2.2.2]oct-3-yl]-4-benzoylbenzamide;
N-[(3R)-1-azabicyclo[2.2.2]oct-3-yl]-4-(4-fluorophenoxy)benzamide;
N-[(3R)-1-azabicyclo[2.2.2]oct-3-yl]-4-(2-fluorophenoxy)benzamide;
N-[(3R)-1-azabicyclo[2.2.2]oct-3-yl]-4-(3-fluorophenoxy)benzamide;
N-[(3R)-1-azabicyclo[2.2.2]oct-3-yl]-4-(2-chlorophenoxy)benzamide;
N-[(3R)-1-azabicyclo[2.2.2]oct-3-yl]-4-(3-chlorophenoxy)benzamide;
N-[(3R)-1-azabicyclo[2.2.2]oct-3-yl]-4-(4-chlorophenoxy)benzamide;
N-[(3R)-1-azabicyclo[2.2.2]oct-3-yl]-4-(2-methoxyphenoxy)benzamide;
N-[(3R)-1-azabicyclo[2.2.2]oct-3-yl]-4-(3-methoxyphenoxy)benzamide;
N-[(3R)-1-azabicyclo[2.2.2]oct-3-yl]-4-(4-methoxyphenoxy)benzamide;
N-[(3R)-1-azabicyclo[2.2.2]oct-3-yl]-4-(3-chlorophenylsulfanyl)benzamide;
N-[(3R)-1-azabicyclo[2.2.2]oct-3-yl]-4-(4-chlorophenylsulfanyl)benzamide;
N-[(3R)-1-azabicyclo[2.2.2]oct-3-yl]-4-(2-chlorophenylsulfanyl)benzamide;
N-[(3R)-1-azabicyclo[2.2.2]oct-3-yl]-4-(4-methoxyphenylsulfanyl)-benzamide;
N-[(3R)-1-azabicyclo[2.2.2]oct-3-yl]-4-(3-methoxyphenylsulfanyl)-benzamide;
N-[(3R)-1-azabicyclo[2.2.2]oct-3-yl]-4-(2-methoxyphenylsulfanyl)-benzamide;
N-(2-methyl-1-azabicyclo[2.2.2]oct-3-yl)-4-phenoxybenzamide;

and pharmaceutically acceptable salts thereof.

28. The compounds according to claim 11, wherein any-one of or combination of the compounds including:

N-[(2S,3R)-2-methyl-1-azabicyclo[2.2.2]oct-3-yl]-4-(4-hydroxyphenoxy)benzamide; N-[(2S,3R)-2-methyl-1-azabicyclo[2.2.2]oct-3-yl]-4-(4-acetamidophenoxy)benzamide; N-[(2S,3R)-2-methyl-1-azabicyclo[2.2.2]oct-3-yl]-4-phenoxybenzamide; N-[(2S,3R)-2-methyl-azabicyclo[2.2.2]oct-3-yl]-4-benzylbenzamide; N-[(2S,3R)-2-methyl-1-azabicyclo[2.2.2]oct-3-yl]-4-(phenylsulfanyl)benzamide; N-[(2S,3R)-2-methyl-1-azabicyclo[2.2.2]oct-3-yl]-3-phenoxybenzamide; N-[(2S,3R)-2-methyl-1-azabicyclo[2.2.2]oct-3-yl]-4-benzoylbenzamide; N-[(2S,3R)-2-methyl-1-azabicyclo[2.2.2]oct-3-yl]-4-(4-fluorophenoxy)benzamide; N-[(2S,3R)-2-methyl-1-azabicyclo[2.2.2]oct-3-yl]-4-(2-fluorophenoxy)benzamide; N-[(2S,3R)-2-methyl-1-azabicyclo[2.2.2]oct-3-yl]-4-(3-fluorophenoxy)benzamide; N-[(2S,3R)-2-methyl-1-azabicyclo[2.2.2]oct-3-yl]-4-(2-chlorophenoxy)benzamide; N-[(2S,3R)-2-methyl-1-azabicyclo[2.2.2]oct-3-yl]-4-(3-chlorophenoxy)benzamide; N-[(2S,3R)-2-methyl-1-azabicyclo[2.2.2]oct-3-yl]-4-(4-chlorophenoxy)benzamide; N-[(2S,3R)-2-methyl-1-azabicyclo[2.2.2]oct-3-yl]-4-(2-methoxyphenoxy)benzamide; N-[(2S,3R)-2-methyl-1-azabicyclo[2.2.2]oct-3-yl]-4-(3-methoxyphenoxy)benzamide; N-[(2S,3R)-2-methyl-1-azabicyclo[2.2.2]oct-3-yl]-4-(4-methoxyphenoxy)benzamide; N-[(2S,3R)-2-methyl-1-azabicyclo[2.2.2]oct-3-yl]-4-(3-chlorophenylsulfanyl)benzamide; N-[(2S,3R)-2-methyl-1-azabicyclo[2.2.2]oct-3-yl]-4-(4-chlorophenylsulfanyl)benzamide; N-[(2S,3R)-2-methyl-1-azabicyclo[2.2.2]oct-3-yl]-4-(2-chlorophenylsulfanyl)benzamide; N-[(2S,3R)-2-methyl-1-azabicyclo[2.2.2]oct-3-yl]-4-(4-methoxyphenylsulfanyl)-benzamide; N-[(2S,3R)-2-methyl-1-azabicyclo[2.2.2]oct-3-yl]-4-(3-methoxyphenylsulfanyl)-benzamide; N-[(2S,3R)-2-methyl-1-azabicyclo[2.2.2]oct-3-yl]-4-(2-methoxyphenylsulfanyl)-benzamide; N-[(2S,3R)-2-methyl-1-azabicyclo[2.2.2]oct-3-yl]-4-phenoxybenzamide; N-[(3R)-1-azabicyclo[2.2.2]oct-3-yl]-4-(4-aminophenoxy)-benzamide; N-[(3R)-1-azabicyclo[2.2.2]oct-3-yl]-4-(3-aminophenoxy)-benzamide; N-[(3R)-1-azabicyclo[2.2.2]oct-3-yl]-4-(2-aminophenoxy)-benzamide; N-[(3R)-1-azabicyclo[2.2.2]oct-3-yl]-4-(4-methanesulfonylamino-phenoxy)-benzamide; N-[(3R)-1-azabicyclo[2.2.2]oct-3-yl]-4-(3-methanesulfonylamino-phenoxy)-benzamide; N-[(3R)-1-azabicyclo[2.2.2]oct-3-yl]-4-(2-methanesulfonylamino-phenoxy)-benzamide; N-[(3R)-1-azabicyclo[2.2.2]oct-3-yl]-4-(4-acetoxyphenoxy)-benzamide; N-[(3R)-1-azabicyclo[2.2.2]oct-3-yl]-4-(3-acetoxyphenoxy)-benzamide; N-[(3R)-1-azabicyclo[2.2.2]oct-3-yl]-4-(2-acetoxyphenoxy)-benzamide; N-[(3R)-1-azabicyclo[2.2.2]oct-3-yl]-4-(4-acetylphenoxy)-benzamide; N-[(3R)-1-azabicyclo[2.2.2]oct-3-yl]-4-(3-acetylphenoxy)-benzamide; N-[(3R)-1-azabicyclo[2.2.2]oct-3-yl]-4-(2-acetylphenoxy)-benzamide; N-[(3R)-1- azabicyclo[2.2.2]oct-3-yl]-4-(4-carbamoylphenoxy)-benzamide; N-[(3R)-1-azabicyclo[2.2.2]oct-3-yl]-4-(3-carbamoylphenoxy)-benzamide; N-[(3R)-1-azabicyclo[2.2.2]oct-3-yl]-4-(2-carbamoylphenoxy)-benzamide; N-[(3R)-1-azabicyclo[2.2.2]oct-3-yl]-4-(4-cyanophenoxy)-benzamide; N-[(3R)-1-azabicyclo[2.2.2]oct-3-yl]-4-(3-cyanophenoxy)-benzamide; N-[(3R)-1-azabicyclo[2.2.2]oct-3-yl]-4-(2-cyanophenoxy)-benzamide; N-[(3R)-1-azabicyclo[2.2.2]oct-3-yl]-4-(4-sulfamoylphenoxy)-benzamide; N-[(3R)-1-azabicyclo[2.2.2]oct-3-yl]-4-(3-sulfamoylphenoxy)-benzamide; N-[(3R)-1-azabicyclo[2.2.2]oct-3-yl]-4-(2-sulfamoylphenoxy)-benzamide; N-[(3R)-1-azabicyclo[2.2.2]oct-3-yl]-4-(thiophen-2-yloxy)-benzamide; N-[(3R)-1-azabicyclo[2.2.2]oct-3-yl]-4-(5-methylthiophen-2-yloxy)-benzamide; N-[(3R)-1-azabicyclo[2.2.2]oct-3-yl]-4-(5-chlorothiophen-2-yloxy)-benzamide; N-[(3R)-1-azabicyclo[2.2.2]oct-3-yl]-4-(5-methoxythiophen-2-yloxy)-benzamide; N-[(3R)-1-azabicyclo[2.2.2]oct-3-yl]-4-(5-trifluoromethylthiophen-2-yloxy)-benzamide; N-[(3R)-1-azabicyclo[2.2.2]oct-3-yl]-4-(5-acetylthiophen-2-yloxy)-benzamide; N-[(3R)-1-azabicyclo[2.2.2]oct-3-yl]-4-(5-acetaminothiophen-2-yloxy)-benzamide; N-[(3R)-1-azabicyclo[2.2.2]oct-3-yl]-4-(5-cyanothiophen-2-yloxy)-benzamide; N-[(3R)-1-azabicyclo[2.2.2]oct-3-yl]-4-(5-morpholin-4-yl-thiophen-2-yloxy)-benzamide; N-[(3R)-1-azabicyclo[2.2.2]oct-3-yl]-4-(4-methylthiophen-2-yloxy)-benzamide; N-[(3R)-1-azabicyclo[2.2.2]oct-3-yl]-4-(4-chlorothiophen-2-yloxy)-benzamide; N-[(3R)-1-azabicyclo[2.2.2]oct-3-yl]-4-(4-methoxythiophen-2-yloxy)-benzamide; N-[(3R)-1-azabicyclo[2.2.2]oct-3-yl]-4-(4-trifluoromethylthiophen-2-yloxy)-benzamide; N-[(3R)-1-azabicyclo[2.2.2]oct-3-yl]-4-(4-acetylthiophen-2-yloxy)-benzamide; N-[(3R)-1-azabicyclo[2.2.2]oct-3-yl]-4-(4-acetaminothiophen-2-yloxy)-benzamide; N-[(3R)-1-azabicyclo[2.2.2]oct-3-yl]-4-(4-cyanothiophen-2-yloxy)-benzamide; N-[(3R)-1-azabicyclo[2.2.2]oct-3-yl]-4-(4-morpholin-4-yl-thiophen-2-yloxy)-benzamide; N-[(3R)-1-azabicyclo[2.2.2]oct-3-yl]-4-(furan-2-yloxy)-benzamide; N-[(3R)-1-azabicyclo[2.2.2]oct-3-yl]-4-(5-methylfuran-2-yloxy)-benzamide; N-[(3R)-1-azabicyclo[2.2.2]oct-3-yl]-4-(5-chlorofuran-2-yloxy)-benzamide; N-[(3R)-1-azabicyclo[2.2.2]oct-3-yl]-4-(5-methoxyfuran-2-yloxy)-benzamide; N-[(3R)-1-azabicyclo[2.2.2]oct-3-yl]-4-(5-trifluoromethylfuran-2-yloxy)-benzamide; N-[(3R)-1-azabicyclo[2.2.2]oct-3-yl]-4-(5-acetylfuran-2-yloxy)-benzamide; N-[(3R)-1-azabicyclo[2.2.2]oct-3-yl]-4-(5-acetaminofuran-2-yloxy)-benzamide; N-[(3R)-1-azabicyclo[2.2.2]oct-3-yl]-4-(5cyanofuran-2-yloxy)-benzamide; N-[(3R)-1-azabicyclo[2.2.2]oct-3-yl]-4-(5-morpholin-4-yl-furan-2-yloxy)-benzamide; N-[(3R)-1-azabicyclo[2.2.2]oct-3-yl]-4-(4-methylfuran-2-yloxy)-benzamide; N-[(3R)-1-azabicyclo[2.2.2]oct-3-yl]-4-(4-chlorofuran-2-yloxy)-benzamide; N-[(3R)-1-azabicyclo[2.2.2]oct-3-yl]-4-(4-methoxyfuran-2-yloxy)-benzamide; N-[(3R)-1-azabicyclo[2.2.2]oct-3-yl]-4-(4-trifluoromethylfuran-2-yloxy)-benzamide; N-[(3R)-1-azabicyclo[2.2.2]oct-3-yl]-4-(4-acetylfuran-2-yloxy)-benzamide; N-[(3R)-1-azabicyclo[2.2.2]oct-3-yl]-4-(4-acetaminofuran-2-yloxy)-benzamide; N-[(3R)-1-azabicyclo[2.2.2]oct-3-yl]-4-(4-cyanofuran-2-yloxy)-benzamide; N-[(3R)-1-azabicyclo[2.2.2]oct-3-yl]-4-(4-morpholin-4-yl-furan-2-yloxy)-benzamide; N-[(3R)-1-azabicyclo[2.2.2]oct-3-yl]-4-(oxazol-2-yloxy)-benzamide; N-[(3R)-1-azabicyclo[2.2.2]oct-3-yl]-4-(5-methyloxazol-2-yloxy)-benzamide; N-[(3R)-1-azabicyclo[2.2.2]oct-3-yl]-4-(5-chlorooxazol-2-yloxy)-benzamide; N-[(3R)-1-azabicyclo[2.2.2]oct-3-yl]-4-(5-methoxyoxazol-2-yloxy)-benzamide; N-[(3R)-1-azabicyclo[2.2.2]oct-3-yl]-4-(5-trifluoromethyloxazol-2-yloxy)-benzamide; N-[(3R)-1-azabicyclo[2.2.2]oct-3-yl]-4-(5-acetyloxazol-2-yloxy)-benzamide; N-[(3R)-1-azabicyclo[2.2.2]oct-3-yl]-4-(5-acetaminooxazol-2-yloxy)-benzamide; N-[(3R)-1-azabicyclo[2.2.2]oct-3-yl]-4-(5-cyanooxazol-2-yloxy)-benzamide; N-[(3R)-1-azabicyclo[2.2.2]oct-3-yl]-4-(5-morpholin-4-yl-oxazol-2-yloxy)-benzamide; N-[(3R)-1-azabicyclo[2.2.2]oct-3-yl]-4-(oxazol-2-yloxy)-benzamide; N-[(3R)-1-azabicyclo[2.2.2]oct-3-yl]-4-(4-methyloxazol-2-yloxy)-benzamide; N-[(3R)-1-azabicyclo[2.2.2]oct-3-yl]-4-(4-chlorooxazol-2-yloxy)-benzamide; N-[(3R)-1-azabicyclo[2.2.2]oct-3-yl]-4-(4-methoxyoxazol-2-yloxy)-benzamide; N-[(3R)-1-azabicyclo[2.2.2]oct-3-yl]-4-(4-trifluoromethyloxazol-2-yloxy)-benzamide; N-[(3R)-1-azabicyclo[2.2.2]oct-3-yl]-4-(4-acetyloxazol-2-yloxy)-benzamide; N-[(3R)-1-azabicyclo[2.2.2]oct-3-yl]-4-(4-acetaminooxazol-2-yloxy)-benzamide; N-[(3R)-1-azabicyclo[2.2.2]oct-3-yl]-4-(4-cyanooxazol-2-yloxy)-benzamide; N-[(3R)-1-azabicyclo[2.2.2]oct-3-yl]-4-(4-morpholin-4-yl-oxazol-2-yloxy)-benzamide; N-[(3R)-1-azabicyclo[2.2.2]oct-3-yl]-4-(oxazol-5-yloxy)-benzamide; N-[(3R)-1-azabicyclo[2.2.2]oct-3-yl]-4-(2-methyloxazol-5-yloxy)-benzamide; N-[(3R)-1-azabicyclo[2.2.2]oct-3-yl]-4-(2-chlorooxazol-5-yloxy)-benzamide; N-[(3R)-1-azabicyclo[2.2.2]oct-3-yl]-4-(2-methoxyoxazol-5-yloxy)-benzamide; N-[(3R)-1-azabicyclo[2.2.2]oct-3-yl]-4-(2-trifluoromethyloxazol-5-yloxy)-benzamide; N-[(3R)-1-azabicyclo[2.2.2]oct-3-yl]-4-(2-acetyloxazol-5-yloxy)-benzamide; N-[(3R)-1-azabicyclo[2.2.2]oct-3-yl]-4-(2-acetaminooxazol-5-yloxy)-benzamide; N-[(3R)-1-azabicyclo[2.2.2]oct-3-yl]-4-(2-cyanooxazol-5-yloxy)-benzamide; N-[(3R)-1-azabicyclo[2.2.2]oct-3-yl]-4-(2-morpholin-4-yl-oxazol-5-yloxy)-benzamide; N-[(3R)-1-azabicyclo[2.2.2]oct-3-yl]-4-(thiazol-2-yloxy)-benzamide; N-[(3R)-1-azabicyclo[2.2.2]oct-3-yl]-4-(5-methylthiazol-2-yloxy)-benzamide; N-[(3R)-1-azabicyclo[2.2.2]oct-3-yl]-4-(5-chlorothiazol-2-yloxy)-benzamide; N-[(3R)-1-azabicyclo[2.2.2]oct-3-yl]-4-(5-methoxythiazol-2-yloxy)-benzamide; N-[(3R)-1-azabicyclo[2.2.2]oct-3-yl]-4-(5-trifluoromethylthiazol-2-yloxy)-benzamide; N-[(3R)-1-azabicyclo[2.2.2]oct-3-yl]-4-(5-acetylthiazol-2-yloxy)-benzamide; N-[(3R)-1-azabicyclo[2.2.2]oct-3-yl]-4-(5-acetaminothiazol-2-yloxy)-benzamide; N-[(3R)-1-azabicyclo[2.2.2]oct-3-yl]-4-(5-cyanothiazol-2-yloxy)-benzamide; N-[(3R)-1-azabicyclo[2.2.2]oct-3-yl]-4-(5-morpholin-4-yl-thiazol-2-yloxy)-benzamide; N-[(3R)-1-azabicyclo[2.2.2]oct-3-yl]-4-(thiazol-2-yloxy)-benzamide; N-[(3R)-1-azabicyclo[2.2.2]oct-3-yl]-(4-methylthiazol-2-yloxy)-benzamide; N-[(3R)-1-azabicyclo[2.2.2]oct-3-yl]-4-(4-chlorothiazol-2-yloxy)-benzamide; N-[(3R)-1-azabicyclo[2.2.2]oct-3-yl]-4-(4-methoxythiazol-2-yloxy)-benzamide; N-[(3R)-1-azabicyclo[2.2.2]oct-3-yl]-4-(4-trifluoromethylthiazol-2-yloxy)-benzamide; N-[(3R)-1-azabicyclo[2.2.2]oct-3-yl]-4-(4-acetylthiazol-2-yloxy)-benzamide; N-[(3R)-1-azabicyclo[2.2.2]oct-3-yl]-4-(4-acetaminothiazol-2-yloxy)-benzamide; N-[(3R)-1-azabicyclo[2.2.2]oct-3-yl]-4-(4-cyanothiazol-2-yloxy)-benzamide; N-[(3R)-1-azabicyclo[2.2.2]oct-3-yl]-4-(4-morpholin-4-yl-thiazol-2-yloxy)-benzamide; N-[(3R)-1-azabicyclo[2.2.2]oct-3-yl]-4-(thiazol-5-yloxy)-benzamide; N-[(3R)-1-azabicyclo[2.2.2]oct-3-yl]-4-(2-methylthiazol-5-yloxy)-benzamide; N-[(3R)-1-azabicyclo[2.2.2]oct-3-yl]-4-(2-chlorothiazol- 5-yloxy)-benzamide; N-[(3R)-1-azabicyclo[2.2.2]oct-3-yl]-4-(2-methoxythiazol-5-yloxy)-benzamide; N-[(3R)-1-azabicyclo[2.2.2]oct-3-yl]-4-(2-trifluoromethylthiazol-5-yloxy)-benzamide; N-[(3R)-1-azabicyclo[2.2.2]oct-3-yl]-4-(2-acetylthiazol-5-yloxy)-benzamide; N-[(3R)-1-azabicyclo[2.2.2]oct-3-yl]-4-(2-acetaminothiazol-5-yloxy)-benzamide; N-[(3R)-1-azabicyclo[2.2.2]oct-3-yl]-4-(2-cyanothiazol-5-yloxy)-benzamide; N-[(3R)-1-azabicyclo[2.2.2]oct-3-yl]-4-(2-morpholin-4-yl-thiazol-5-yloxy)-benzamide; N-[(3R)-1-azabicyclo[2.2.2]oct-3-yl]-4-([1,3,4]oxadiazol-2-yloxy)-benzamide; N-[(3R)-1-azabicyclo[2.2.2]oct-3-yl]-4-(5-methyl[1,3,4]oxadiazol-2-yloxy)-benzamide; N-[(3R)-1-azabicyclo[2.2.2]oct-3-yl]-4-(5-chloro[1,3,4]oxadiazol-2-yloxy)-benzamide; N-[(3R)-1-azabicyclo[2.2.2]oct-3-yl]-4-(5-methoxy[1,3,4]oxadiazol-2-yloxy)-benzamide; N-[(3R)-1-azabicyclo[2.2.2]oct-3-yl]-4-(5-trifluoromethyl[1,3,4]oxadiazol-2-yloxy)-benzamide; N-[(3R)-1-azabicyclo[2.2.2]oct-3-yl]-4-(5-acetyl[1,3,4]oxadiazol-2-yloxy)-benzamide; N-[(3R)-1-azabicyclo[2.2.2]oct-3-yl]-4-(5-acetamino[1,3,4]oxadiazol-2-yloxy)-benzamide; N-[(3R)-1-azabicyclo[2.2.2]oct-3-yl]-4-(5-cyano[1,3,4]oxadiazol-2-yloxy)-benzamide; N-[(3R)-1-azabicyclo[2.2.2]oct-3-yl]-4-(5-morpholin-4-yl-[1,3,4]oxadiazol-2-yloxy)-benzamide; N-[(3R)-1-azabicyclo[2.2.2]oct-3-yl]-4-([1,3,4]thiadiazol-2-yloxy)-benzamide; N-[(3R)-1-azabicyclo[2.2.2]oct-3-yl]-4-(5-methyl[1,3,4]thiadiazol-2-yloxy)-benzamide; N-[(3R)-1-azabicyclo[2.2.2]oct-3-yl]-4-(5-chloro[1,3,4]thiadiazol-2-yloxy)-benzamide; N-[(3R)-1-azabicyclo[2.2.2]oct-3-yl]-4-(5-methoxy[1,3,4]thiadiazol-2-yloxy)-benzamide; N-[(3R)-1-azabicyclo[2.2.2]oct-3-yl]-4-(5-trifluoromethyl[1,3,4]thiadiazol-2-yloxy)-benzamide; N-[(3R)-1-azabicyclo[2.2.2]oct-3-yl]-4-(5-acetyl[1,3,4]thiadiazol-2-yloxy)-benzamide; N-[(3R)-1-azabicyclo[2.2.2]oct-3-yl]-4-(5-acetamino[1,3,4]thiadiazol-2-yloxy)-benzamide; N-[(3R)-1-azabicyclo[2.2.2]oct-3-yl]-4-(5-cyano[1,3,4]thiadiazol-2-yloxy)-benzamide; N-[(3R)-1-azabicyclo[2.2.2]oct-3-yl]-4-(5-morpholin-4-yl-[1,3,4]thiadiazol-2-yloxy)-benzamide; N-[(3R)-azabicyclo[2.2.2]oct-3-yl]-4-(4-aminophenylsulfanyl)-benzamide; N-[(3R)-1-azabicyclo[2.2.2]oct-3-yl]-4-(3-aminophenylsulfanyl)-benzamide; N-[(3R)-1-azabicyclo[2.2.2]oct-3-yl]-4-(2-aminophenylsulfanyl)-benzamide; N-[(3R)-1-azabicyclo[2.2.2]oct-3-yl]-4-(4-methanesulfonylamino-phenylsulfanyl)-benzamide; N-[(3R)-1-azabicyclo[2.2.2]oct-3-yl]-4-(3-methanesulfonylamino-phenylsulfanyl)-benzamide; N-[(3R)-1-azabicyclo[2.2.2]oct-3-yl]-4-(2-methanesulfonylamino-phenylsulfanyl)-benzamide; N-[(3R)-1-azabicyclo[2.2.2]oct-3-yl]-4-(4-acetoxyphenylsulfanyl)-benzamide; N-[(3R)-1-azabicyclo[2.2.2]oct-3-yl]-4-(3-acetoxyphenylsulfanyl)-benzamide; N-[(3R)-1-azabicyclo[2.2.2]oct-3-yl]-4-(2-acetoxyphenylsulfanyl)-benzamide; N-[(3R)-1-azabicyclo[2.2.2]oct-3-yl]-4-(4-acetylphenylsulfanyl)-benzamide; N-[(3R)-1-azabicyclo[2.2.2]oct-3-yl]-4-(3-acetylphenylsulfanyl)-benzamide; N-[(3R)-1-azabicyclo[2.2.2]oct-3-yl]-4-(2-acetylphenylsulfanyl)-benzamide; N-[(3R)-1-azabicyclo[2.2.2]oct-3-yl]-4-(4-carbamoylphenylsulfanyl)-benzamide; N-[(3R)-1-azabicyclo[2.2.2]oct-3-yl]-4-(3-carbamoylphenylsulfanyl)-benzamide; N-[(3R)-1-azabicyclo[2.2.2]oct-3-yl]-4-(2-carbamoylphenylsulfanyl)-benzamide; N-[(3R)-1-azabicyclo[2.2.2]oct-3-yl]-4-(4-cyanophenylsulfanyl)-benzamide; N-[(3R)-1-azabicyclo[2.2.2]oct-3-yl]-4-(3-cyanophenylsulfanyl)-benzamide; N-[(3R)-1-azabicyclo[2.2.2]oct-3-yl]-4-(2-cyanophenylsulfanyl)-benzamide; N-[(3R)-1-azabicyclo[2.2.2]oct-3-yl]-4-(4-sulfamoylphenylsulfanyl)-benzamide; N-[(3R)-1-azabicyclo[2.2.2]oct-3-yl]-4-(3-sulfamoylphenylsulfanyl)-benzamide; N-[(3R)-1-azabicyclo[2.2.2]oct-3-yl]-4-(2-sulfamoylphenylsulfanyl)-benzamide; N-[(3R)-1-azabicyclo[2.2.2]oct-3-yl]-4-(4-hydroxyphenylsulfanyl)-benzamide; N-[(3R)-1-azabicyclo[2.2.2]oct-3-yl]-4-(3-hydroxyphenylsulfanyl)-benzamide; N-[(3R)-1-azabicyclo[2.2.2]oct-3-yl]-4-(2-hydroxyphenylsulfanyl)-benzamide; N-[(3R)-1-azabicyclo[2.2.2]oct-3-yl]-4-(4-acetamidophenylsulfanyl)-benzamide; N-[(3R)-1-azabicyclo[2.2.2]oct-3-yl]-4-(3-acetamidophenylsulfanyl)-benzamide; N-[(3R)-1-azabicyclo[2.2.2]oct-3-yl]-4-(2-acetamidophenylsulfanyl)-benzamide; N-[(3R)-1-azabicyclo[2.2.2]oct-3-yl]-4-(thiophen-2-ylsulfanyl)-benzamide; N-[(3R)-1-azabicyclo[2.2.2]oct-3-yl]-4-(5-methylthiophen-2-ylsulfanyl)-benzamide; N-[(3R)-1-azabicyclo[2.2.2]oct-3-yl]-4-(5-chlorothiophen-2-ylsulfanyl)-benzamide; N-[(3R)-1-azabicyclo[2.2.2]oct-3-yl]-4-(5-methoxythiophen-2-ylsulfanyl)-benzamide; N-[(3R)-1-azabicyclo[2.2.2]oct-3-yl]-4-(5-trifurmethoylthiophen-2-ylsulfanyl)-benzamide; N-[(3R)-1-azabicyclo[2.2.2]oct-3-yl]-4-(5-acetylthiophen-2-ylsulfanyl)-benzamide; N-[(3R)-1-azabicyclo[2.2.2]oct-3-yl]-4-(5-acetaminothiophen-2-ylsulfanyl)-benzamide; N-[(3R)-1-azabicyclo[2.2.2]oct-3-yl]-4-(5-cyanothiophen-2-ylsulfanyl)-benzamide; N-[(3R)-1-azabicyclo[2.2.2]oct-3-yl]-4-(5-morpholin-4-yl-thiophen-2-ylsulfanyl)-benzamide; N-[(3R)-1-azabicyclo[2.2.2]oct-3-yl]-4-(4-methylthiophen-2-ylsulfanyl)-benzamide; N-[(3R)-1-azabicyclo[2.2.2]oct-3-yl]-4-(4-chlorothiophen-2-ylsulfanyl)-benzamide; N-[(3R)-1-azabicyclo[2.2.2]oct-3-yl]-4-(4-methoxythiophen-2-ylsulfanyl)-benzamide; N-[(3R)-1-azabicyclo[2.2.2]oct-3-yl]-4-(4-trifluororethylthiophen-2-ylsulfanyl)-benzamide; N-[(3R)-1-azabicyclo[2.2.2]oct-3-yl]-4-(4-acetylthiophen-2-ylsulfanyl)-benzamide; N-[(3R)-1-azabicyclo[2.2.2]oct-3-yl]-4-(4-acetaminothiophen-2-ylsulfanyl)-benzamide; N-[(3R)-1-azabicyclo[2.2.2]oct-3-yl]-4-(4-cyanothiophen-2-ylsulfanyl)-benzamide; N-[(3R)-1-azabicyclo[2.2.2]oct-3-yl]-4-(4-morpholin-4-yl-thiophen-2-ylsulfanyl)-benzamide; N-[(3R)-1-azabicyclo[2.2.2]oct-3-yl]-4-(furan-2-ylsulfanyl)-benzamide; N-[(3R)-1-azabicyclo[2.2.2]oct-3-yl]-4-(5-methylfuran-2-ylsulfanyl)-benzamide; N-[(3R)-1-azabicyclo[2.2.2]oct-3-yl]-4-(5-chlorofuran-2-ylsulfanyl)-benzamide; N-[(3R)-1-azabicyclo[2.2.2]oct-3-yl]-4-(5-methoxyfuran-2-ylsulfanyl)-benzamide; N-[(3R)-1-azabicyclo[2.2.2]oct-3-yl]-4-(5-trifluoromethylfuran-2-ylsulfanyl)-benzamide; N-[(3R)-1-azabicyclo[2.2.2]oct-3-yl]-4-(5-acetylfuran-2-ylsulfanyl)-benzamide; N-[(3R)-1-azabicyclo[2.2.2]oct-3-yl]-4-(5-acetaminofuran-2-ylsulfanyl)-benzamide; N-[(3R)-1-azabicyclo[2.2.2]oct-3-yl]-4-(5-cyanofuran-2-ylsulfanyl)-benzamide; N-[(3R)-1-azabicyclo[2.2.2]oct-3-yl]-4-(5-morpholin-4-yl-furan-2-ylsulfanyl)-benzamide; N-[(3R)-1-azabicyclo[2.2.2]oct-3-yl]-4-(4-methylfuran-2-ylsulfanyl)-benzamide; N-[(3R)-1-azabicyclo[2.2.2]oct-3-yl]-4-(4-chlorofuran-2-ylsulfanyl)-benzamide; N-[(3R)-1-azabicyclo[2.2.2]oct-3-yl]-4-(4-methoxyfuran-2-ylsulfanyl)-benzamide; N-[(3R)-1-azabicyclo[2.2.2]oct-3-yl]-4-(4-trifluoromethylfuran-2-ylsulfanyl)-benzamide; N-[(3R)-1-azabicyclo[2.2.2]oct-3-yl]-4-(4-acetylfuran-2- ylsulfanyl)-benzamide; N-[(3R)-1-azabicyclo[2.2.2]oct-3-yl]-4-(4-acetaminofuran-2-ylsulfanyl)-benzamide; N-[(3R)-1-azabicyclo[2.2.2]oct-3-yl]-4-(4-cyanofuran-2-ylsulfanyl)-benzamide; N-[(3R)-1-azabicyclo[2.2.2]oct-3-yl]-4-(4-morpholin-4-yl-furan-2-ylsulfanyl)-benzamide; N-[(3R)-1-azabicyclo[2.2.2]oct-3-yl]-4-(oxazol-2-ylsulfanyl)-benzamide; N-[(3R)-1-azabicyclo[2.2.2]oct-3-yl]-4-(5-methyloxazol-2-ylsulfanyl)-benzamide; N-[(3R)-1-azabicyclo[2.2.2]oct-3-yl]-4-(5-chlorooxazol-2-ylsulfanyl)-benzamide; N-[(3R)-1-azabicyclo[2.2.2]oct-3-yl]-4-(5-methoxyoxazol-2-ylsulfanyl)-benzamide; N-[(3R)-1-azabicyclo[2.2.2]oct-3-yl]-4-(5-trifluoromethyloxazol-2-ylsulfanyl)-benzamide; N-[(3R)-1-azabicyclo[2.2.2]oct-3-yl]-4-(5-acetyloxazol-2-ylsulfanyl)-benzamide; N-[(3R)-1-azabicyclo[2.2.2]oct-3-yl]-4-(5-acetaminooxazol-2-ylsulfanyl)-benzamide; N-[(3R)-1-azabicyclo[2.2.2]oct-3-yl]-4-(5-cyanooxazol-2-ylsulfanyl)-benzamide; N-[(3R)-1-azabicyclo[2.2.2]oct-3-yl]-4-(5-morpholin-4-yl-oxazol-2-ylsulfanyl)-benzamide; N-[(3R)-1-azabicyclo[2.2.2]oct-3-yl]-4-(oxazol-2-ylsulfanyl)-benzamide; N-[(3R)-1-azabicyclo[2.2.2]oct-3-yl]-4-(4-methyloxazol-2-ylsulfanyl)-benzamide; N-[(3R)-1-azabicyclo[2.2.2]oct-3-yl]-4-(4-chlorooxazol-2-ylsulfanyl)-benzamide; N-[(3R)-1-azabicyclo[2.2.2]oct-3-yl]-4-(4-methoxyoxazol-2-ylsulfanyl)-benzamide; N-[(3R)-1-azabicyclo[2.2.2]oct-3-yl]-4-(4-trifluoromethyloxazol-2-ylsulfanyl)-benzamide; N-[(3R)-1-azabicyclo[2.2.2]oct-3-yl]-4-(4-acetyloxazol-2-ylsulfanyl)-benzamide; N-[(3R)-1-azabicyclo[2.2.2]oct-3-yl]-4-(4-acetaminooxazol-2-ylsulfanyl)-benzamide; N-[(3R)-1-azabicyclo[2.2.2]oct-3-yl]-4-(4-cyanooxazol-2-ylsulfanyl)-benzamide; N-[(3R)-1-azabicyclo[2.2.2]oct-3-yl]-4-(4-morpholin-4-yl-oxazol-2-ylsulfanyl)-benzamide; N-[(3R)-1-azabicyclo[2.2.2]oct-3-yl]-4-(oxazol-5-ylsulfanyl)-benzamide; N-[(3R)-1-azabicyclo[2.2.2]oct-3-yl]-4-(2-methyloxazol-5-ylsulfanyl)-benzamide; N-[(3R)-1-azabicyclo[2.2.2]oct-3-yl]-4-(2-chlorooxazol-5-ylsulfanyl)-benzamide; N-[(3R)-1-azabicyclo[2.2.2]oct-3-yl]-4-(2-methoxyoxazol-5-ylsulfanyl)-benzamide; N-[(3R)-1-azabicyclo[2.2.2]oct-3-yl]-4-(2-trifluoromethyloxazol-5-ylsulfanyl)-benzamide; N-[(3R)-1-azabicyclo[2.2.2]oct-3-yl]-4-(2-acetyloxazol-5-ylsulfanyl)-benzamide; N-[(3R)-1-azabicyclo[2.2.2]oct-3-yl]-4-(2-acetaminooxazol-5-ylsulfanyl)-benzamide; N-[(3R)-1-azabicyclo[2.2.2]oct-3-yl]-4-(2-cyanooxazol-5-ylsulfanyl)-benzamide; N-[(3R)-1-azabicyclo[2.2.2]oct-3-yl]-4-(2-morpholin-4-yl-oxazol-5-ylsulfanyl)-benzamide; N-[(3R)-1-azabicyclo[2.2.2]oct-3-yl]-4-(thiazol-2-ylsulfanyl)-benzamide; N-[(3R)-1-azabicyclo[2.2.2]oct-3-yl]-4-(5-methylthiazol-2-ylsulfanyl)-benzamide; N-[(3R)-1-azabicyclo[2.2.2]oct-3-yl]-4-(5-chlorothiazol-2-ylsulfanyl)-benzamide; N-[(3R)-1-azabicyclo[2.2.2]oct-3-yl]-4-(5-methoxythiazol-2-ylsulfanyl)-benzamide; N-[(3R)-1-azabicyclo[2.2.2]oct-3-yl]-4-(5-trifluoromethylthiazol-2-ylsulfanyl)-benzamide; N-[(3R)-5-azabicyclo[2.2.2]oct-3-yl]-4-(5-acetylthiazol-2-ylsulfanyl)-benzamide; N-[(3R)-1-azabicyclo[2.2.2]oct-3-yl]-4-(5-acetaminothiazol-2-ylsulfanyl)-benzamide; N-[(3R)-1-azabicyclo[2.2.2]oct-3-yl]-4-(5-cyanothiazol-2-ylsulfanyl)-benzamide; N-[(3R)-1-azabicyclo[2.2.2]oct-3-yl]-4-(5morpholin-4-yl-thiazol-2-ylsulfanyl)-benzamide; N-[(3R)-1-azabicyclo[2.2.2]oct-3-yl]-4-(thiazol-2-ylsulfanyl)-benzazide; N-[(3R)-1-azabicyclo[2.2.2]oct-3-yl]-4-(4-methylthiazol-2-ylsulfanyl)-benzamide; N-[(3R)-1-azabicyclo[2.2.2]oct-3-yl]-4-(4-chlorothiazol-2-ylsulfanyl)-benzamide; N-[(3R)-1-azabicyclo[2.2.2]oct-3-yl]-4-(4-methoxythiazol-2-ylsulfanyl)-benzamide; N-[(3R)-1-azabicyclo[2.2.2]oct-3-yl]-4-(4-trifluoromethylthiazol-2-ylsulfanyl)-benzamide; N-[(3R)-1-azabicyclo[2.2.2]oct-3-yl]-4-(4-acetylthiazol-2-ylsulfanyl)-benzamide; N-[(3R)-1-azabicyclo[2.2.2]oct-3-yl]-4-(4-acetaminothiazol-2-ylsulfanyl)-benzamide; N-[(3R)-1-azabicyclo[2.2.2]oct-3-yl]-4-(4-cyanothiazol-2-ylsulfanyl)-benzamide; N-[(3R)-1-azabicyclo[2.2.2]oct-3-yl]-4-(4-morpholin-4-yl-thiazol-2-ylsulfanyl)-benzamide; N-[(3R)-1-azabicyclo[2.2.2]oct-3-yl]-4-(thiazol-5-ylsulfanyl)-benzamide; N-[(3R)-1-azabicyclo[2.2.2]oct-3-yl]-4-(2-methylthiazol-5-ylsulfanyl)-benzamide; N-[(3R)-1-azabicyclo[2.2.2]oct-3-yl]-4-(2-chorothiazol-5-ylsulfanyl)-benzamide; N-[(3R)-1-azabicyclo[2.2.2]oct-3-yl]-4-(2-methoxythiazol-5-ylsulfanyl)-benzamide; N-[(3R)-1-azabicyclo[2.2.2]oct-3-yl]-4-(2-trifluoromethylthiazol-5-ylsulfanyl)-benzamide; N-[(3R)-1-azabicyclo[2.2.2]oct-3-yl]-4-(2-acetylthiazol-5-ylsulfanyl)-benzamide; N-[(3R)-1-azabicyclo[2.2.2]oct-3-yl]-4-(2-acetaminothiazol-5-ylsulfanyl)-benzamide; N-[(3R)-1-azabicyclo[2.2.2]oct-3-yl]-4-(2-cyanothiazol-5-ylsulfanyl)-benzamide; N-[(3R)-1-azabicyclo[2.2.2]oct-3-yl]-4-(2-morpholin-4-yl-thiazol-5-ylsulfanyl)-benzamide; N-[(3R)-1-azabicyclo[2.2.2]oct-3-yl]-4-([1,3,4]oxadiazol-2-ylsulfanyl)-benzamide; N-[(3R)-1-azabicyclo[2.2.2]oct-3-yl]-4-(5-methyl[1,3,4]oxadiazol-2-ylsulfanyl)-benzamide; N-[(3R)-1-azabicyclo[2.2.2]oct-3-yl]-4-(5-chloro[1,3,4]oxadiazol-2-ylsulfanyl)-benzamide; N-[(3R)-1-azabicyclo[2.2.2]oct-3-yl]-4-(5-methoxy[1,3,4]oxadiazol-2-ylsulfanyl)-benzamide; N-[(3R)-1-azabicyclo[2.2.2]oct-3-yl]-4-(5-trifluoromethyl[1,3,4]oxadiazol-2-ylsulfanyl)-benzamide; N-[(3R)-1-azabicyclo[2.2.2]oct-3-yl]-4-(5-acetyl[1,3,4]oxadiazol-2-ylsulfanyl)-benzamide; N-[(3R)-1-azabicyclo[2.2.2]oct-3-yl]-4-(5-acetamino[1,3,4]oxadiazol-2-ylsulfanyl)-benzamide; N-[(3R)-1-azabicyclo[2.2.2]oct-3-yl]-4-(5-cyano[1,3,4]oxadiazol-2-ylsulfanyl)-benzamide; N-[(3R)-1-azabicyclo[2.2.2]oct-3-yl]-4-(5-morpholin-4-yl-[1,3,4]oxadiazol-2-ylsulfanyl)-benzamide; N-[(3R)-1-azabicyclo[2.2.2]oct-3-yl]-4-([1,3,4]thiadiazol-2-ylsulfanyl)-benzamide; N-[(3R)-1-azabicyclo[2.2.2]oct-3-yl]-4-(5-methyl[1,3,4]thiadiazol-2-ylsulfanyl)-benzamide; N-[(3R)-1-azabicyclo[2.2.2]oct-3-yl]-4-(5-chloro[1,3,4]thiadiazol-2-ylsulfanyl)-benzamide; N-[(3R)-1-azabicyclo[2.2.2]oct-3-yl]-4-(5-methoxy[1,3,4]thiadiazol-2-ylsulfanyl)-benzamide; N-[(3R)-1-azabicyclo[2.2.2]oct-3-yl]-4-(5-trifluoromethyl[1,3,4]thiadiazol-2-ylsulfanyl)-benzamide; N-[(3R)-1-azabicyclo[2.2.2]oct-3-yl]-4-(5-acetyl[1,3,4]thiadiazol-2-ylsulfanyl)-benzamide; N-[(3R)-1-azabicyclo[2.2.2]oct-3-yl]-4-(5-acetamino[1,3,4]thiadiazol-2-ylsulfanyl)-benzamide; N-[(3R)-1-azabicyclo[2.2.2]oct-3-yl]-4-(5-cyano[1,3,4]thiadiazol-2-ylsulfanyl)-benzamide; N-[(3R)-1-azabicyclo[2.2.2]oct-3-yl]-4-(5-morpholin-4-yl-[1,3,4]thiadiazol-2-ylsulfanyl)-benzamide; N-[(3R)-1-azabicyclo[2.2.2]oct-3-yl]-4-(pyrrol-2-yloxy)-benzamide; N-[(3R)-1-azabicyclo[2.2.2]oct-3-yl]-4-(5-methylpyrrol-2-yloxy)-benzamide; N-[(3R)-1-azabicyclo[2.2.2]oct-3-yl]-4-(5-chloropyrrol-2-yloxy)-benzamide; N-[(3R)-1-azabicyclo[2.2.2]oct-3-yl]-4-(5-methoxypyrrol-2-yloxy)-benzamide; N-[(3R)-1-azabicyclo[2.2.2]oct-3-yl]-4-(5-trifluoromethylpyrrol-2-yloxy)-benzamide; N-[(3R)-1-azabicyclo[2.2.2]oct-3-yl]-4-(5-acetylpyrrol-2-yloxy)-benzamide; N-[(3R)-1-azabicyclo[2.2.2]oct-3-yl]-4-(5- acetaminopyrrol-2-yloxy)-benzamide; N-[(3R)-1-azabicyclo[2.2.2]oct-3-yl]-4-(5-cyanopyrrol-2-yloxy)-benzamide; N-[(3R)-1-azabicyclo[2.2.2]oct-3-yl]-4-(5-morpholin-4-yl-pyrrol-2-yloxy)-benzamide; N-[(3R)-1-azabicyclo[2.2.2]oct-3-yl]-4-(3H-imidazol-4-yloxy)-benzamide; N-[(3R)-1-azabicyclo[2.2.2]oct-3-yl]-4-(2-methyl-3H-imidazol-4-yloxy)-benzamide; N-[(3R)-1-azabicyclo[2.2.2]oct-3-yl]-4-(2-chloro-3H-imidazol-4-yloxy)-benzamide; N-[(3R)-1-azabicyclo[2.2.2]oct-3-yl]-4-(2-methoxy-3H-imidazol-4-yloxy)-benzamide; N-[(3R)-1-azabicyclo[2.2.2]oct-3-yl]-4-(2-trifluoromethyl-3H-imidazol-4-yloxy)-benzamide; N-[(3R)-1-azabicyclo[2.2.2]oct-3-yl]-4-(2-acetyl-3H-imidazol-4-yloxy)-benzamide; N-[(3R)-1-azabicyclo[2.2.2]oct-3-yl]-4-(2-acetamino-3H-imidazol-4-yloxy)-benzamide; N-[(3R)-1-azabicyclo[2.2.2]oct-3-yl]-4-(2-cyano-3H-imidazol-4-yloxy)-benzamide; N-[(3R)-1-azabicyclo[2.2.2]oct-3-yl]-4-(2-morpholin-4-yl-3H-imidazol-4-yloxy)-benzamide; N-[(3R)-1-azabicyclo[2.2.2]oct-3-yl]-4-(isoxazol-2-yloxy)-benzamide; N-[(3R)-1-azabicyclo[2.2.2]oct-3-yl]-4-(5-methylisoxazol-3-yloxy)-benzamide; N-[(3R)-1-azabicyclo[2.2.2]oct-3-yl]-4-(5-chloroisoxazol-3-yloxy)-benzamide; N-[(3R)-1-azabicyclo[2.2.2]oct-3-yl]-4-(5-methoxyisoxazol-3-yloxy)-benzamide; N-[(3R)-1-azabicyclo[2.2.2]oct-3-yl]-4-(5-trifluoromethylisoxazol-3-yloxy)-benzamide; N-[(3R)-1-azabicyclo[2.2.2]oct-3-yl]-4-(5-acetylisoxazol-3-yloxy)-benzamide; N-[(3R)-1-azabicyclo[2.2.2]oct-3-yl]-4-(5-acetaminoisoxazol-3-yloxy)-benzamide; N-[(3R)-1-azabicyclo[2.2.2]oct-3-yl]-4-(5-cyanoisoxazol-3-yloxy)-benzamide; N-[(3R)-1-azabicyclo[2.2.2]oct-3-yl]-4-(5-morpholin-4-yl-isoxazol-3-yloxy)-benzamide; N-[(3R)-1-azabicyclo[2.2.2]oct-3-yl]-4-(isothiazol-2-yloxy)-benzamide; N-[(3R)-1-azabicyclo[2.2.2]oct-3-yl]-4-(5-methylisothiazol-3-yloxy)-benzamide; N-[(3R)-1-azabicyclo[2.2.2]oct-3-yl]-4-(5-chloroisothiazol-3-yloxy)-benzamide; N-[(3R)-1-azabicyclo[2.2.2]oct-3-yl]-4-(5-methoxyisothiazol-3-yloxy)-benzamide; N-[(3R)-1-azabicyclo[2.2.2]oct-3-yl]-4-(5-trifluoromethylisothiazol-3-yloxy)-benzamide; N-[(3R)-1-azabicyclo[2.2.2]oct-3-yl]-4-(5-acetylisothiazol-3-yloxy)-benzamide; N-[(3R)-1-azabicyclo[2.2.2]oct-3-yl]-4-(5-acetaminoisothiazol-3-yloxy)-benzamide; N-[(3R)-1-azabicyclo[2.2.2]oct-3-yl]-4-(5-cyanoisothiazol-3-yloxy)-benzamide; N-[(3R)-1-azabicyclo[2.2.2]oct-3-yl]-4-(5-morpholin-4-yl-isothiazol-3-yloxy)-benzamide; N-[(3R)-1-azabicyclo[2.2.2]oct-3-yl]-4-(pyrrol-2-ylsulfanyl)-benzamide; N-[(3R)-1-azabicyclo[2.2.2]oct-3-yl]-4-(5-methylpyrrol-2-ylsulfanyl)-benzamide; N-[(3R)-1-azabicyclo[2.2.2]oct-3-yl]-4-(5-chloropyrrol-2-ylsulfanyl)-benzamide; N-[(3R)-1-azabicyclo[2.2.2]oct-3-yl]-4-(5-methoxypyrrol-2-ylsulfanyl)-benzamide; N-[(3R)-1-azabicyclo[2.2.2]oct-3-yl]-4-(5-trifluoromethylpyrrol-2-ylsulfanyl)-benzamide; N-[(3R)-1-azabicyclo[2.2.2]oct-3-yl]-4-(5-acetylpyrrol-2-ylsulfanyl)-benzamide; N-[(3R)-1-azabicyclo[2.2.2]oct-3-yl]-4-(5-acetaminopyrrol-2-ylsulfanyl)-benzamide; N-[(3R)-1-azabicyclo[2.2.2]oct-3-yl]-4-(5-cyanopyrrol-2-ylsulfanyl)-benzamide; N-[(3R)-1-azabicyclo[2.2.2]oct-3-yl]-4-(5-morpholin-4-yl-pyrrol-2-ylsulfanyl)-benzamide; N-[(3R)-1-azabicyclo[2.2.2]oct-3-yl]-4-(3H-imidazol-4-ylsulfanyl)-benzamide; N-[(3R)-1-azabicyclo[2.2.2]oct-3-yl]-4-(2-methyl-3H-imidazol-4-ylsulfanyl)-benzamide; N-[(3R)-1-azabicyclo[2.2.2]oct-3-yl]-4-(2-chloro-3H-imidazol-4-ylsulfanyl)-benzamide; N-[(3R)-1-azabicyclo[2.2.2]oct-3-yl]-4-(2-methoxy-3H-imidazol-4-ylsulfanyl)-benzamide; N-[(3R)-1-azabicyclo[2.2.2]oct-3-yl]-4-(2-trifluoromethyl-3H-imidazol-4-ylsulfanyl)-benzamide; N-[(3R)-1-azabicyclo[2.2.2]oct-3-yl]-4-(2-acetyl-3H-imidazol-4-ylsulfanyl)-benzamide; N-[(3R)-1-azabicyclo[2.2.2]oct-3-yl]-4-(2-acetamino-3H-imidazol-4-ylsulfanyl)-benzamide; N-[(3R)-1-azabicyclo[2.2.2]oct-3-yl]-4-(2-cyano-3H-imidazol-4-ylsulfanyl)-benzamide; N-[(3R)-1-azabicyclo[2.2.2]oct-3-yl]-4-(2-morpholin-4-yl-3H-imidazol-4-ylsulfanyl)-benzamide; N-[(3R)-1-azabicyclo[2.2.2]oct-3-yl]-4-(isoxazol-2-ylsulfanyl)-benzamide; N-[(3R)-1-azabicyclo[2.2.2]oct-3-yl]-4-(5-methylisoxazol-3-ylsulfanyl)-benzamide; N-[(3R)-1-azabicyclo[2.2.2]oct-3-yl]-4-(5-chloroisoxazol-3-ylsulfanyl)-benzamide; N-[(3R)-1-azabicyclo[2.2.2]oct-3-yl]-4-(5-methoxyisoxazol-3-ylsulfanyl)-benzamide; N-[(3R)-1-azabicyclo[2.2.2]oct-3-yl]-4-(5-trifluoromethylisoxazol-3-ylsulfanyl)-benzamide; N-[(3R)-1-azabicyclo[2.2.2]oct-3-yl]-4-(5-acetylisoxazol-3-ylsulfanyl)-benzamide; N-[(3R)-1-azabicyclo[2.2.2]oct-3-yl]-4-(5-acetaminoisoxazol-3-ylsulfanyl)-benzamide; N-[(3R)-1-azabicyclo[2.2.2]oct-3-yl]-4-(5-cyanoisoxazol-3-ylsulfanyl)-benzamide; N-[(3R)-1-azabicyclo[2.2.2]oct-3-yl]-4-(5-morpholin-4-yl-isoxazol-3-ylsulfanyl)-benzamide; N-[(3R)-1-azabicyclo[2.2.2]oct-3-yl]-4-(isothiazol-2-ylsulfanyl)-benzamide; N-[(3R)-1-azabicyclo[2.2.2]oct-3-yl]-4-(5-methylisothiazol-3-ylsulfanyl)-benzamide; N-[(3R)-1-azabicyclo[2.2.2]oct-3-yl]-4-(5-chloroisothiazol-3-ylsulfanyl)-benzamide; N-[(3R)-1-azabicyclo[2.2.2]oct-3-yl]-4-(5-methoxyisothiazol-3-ylsulfanyl)-benzamide; N-[(3R)-1-azabicyclo[2.2.2]oct-3-yl]-4-(5-trifluoromethylisothiazol-3-ylsulfanyl)-benzamide; N-[(3R)-1-azabicyclo[2.2.2]oct-3-yl]-4-(5-acetylisothiazol-3-ylsulfanyl)-benzamide; N-[(3R)-1-azabicyclo[2.2.2]oct-3-yl]-4-(5-acetaminoisothiazol-3-ylsulfanyl)-benzamide; N-[(3R)-1-azabicyclo[2.2.2]oct-3-yl]-4-(5-cyanoisothiazol-3-ylsulfanyl)-benzamide; N-[(3R)-1-azabicyclo[2.2.2]oct-3-yl]-4-(5-morpholin-4-yl-isothiazol-3-ylsulfanyl)-benzamide; N-[(3R)-1-azabicyclo[2.2.2]oct-3-yl]-4-(6-methylpyridin-3-yloxy)-benzamide; N-[(3R)-1-azabicyclo[2.2.2]oct-3-yl]-4-(6-chloropyridin-3-yloxy)-benzamide; N-[(3R)-1-azabicyclo[2.2.2]oct-3-yl]-4-(6-methoxypyridin-3-yloxy)-benzamide; N-[(3R)-1-azabicyclo[2.2.2]oct-3-yl]-4-(6-trifluoromethylpyridin-3-yloxy)-benzamide; N-[(3R)-1-azabicyclo[2.2.2]oct-3-yl]-4-(6-acetylpyridin-3-yloxy)-benzamide; N-[(3R)-1-azabicyclo[2.2.2]oct-3-yl]-4-(6-acetaminopyridin-3-yloxy)-benzamide; N-[(3R)-1-azabicyclo[2.2.2]oct-3-yl]-4-(6-cyanopyridin-3-yloxy)-benzamide; N-[(3R)-1-azabicyclo[2.2.2]oct-3-yl]-4-(6-morpholin-4-yl-pyridin-3-yloxy)-benzamide; N-[(3R)-1-azabicyclo[2.2.2]oct-3-yl]-4-(2-methylpyridin-4-yloxy)-benzamide; N-[(3R)-1-azabicyclo[2.2.2]oct-3-yl]-4-(2-chloropyridin-4-yloxy)-benzamide; N-[(3R)-1-azabicyclo[2.2.2]oct-3-yl]-4-(2-methoxypyridin-4-yloxy)-benzamide; N-[(3R)-1-azabicyclo[2.2.2]oct-3-yl]-4-(2-trifluoromethylpyridin-4-yloxy)-benzamide; N-[(3R)-1-azabicyclo[2.2.2]oct-3-yl]-4-(2-acetylpyridin-4-yloxy)-benzamide; N-[(3R)-1-azabicyclo[2.2.2]oct-3-yl]-4-(2-acetaminopyridin-4-yloxy)-benzamide; N-[(3R)-1-azabicyclo[2.2.2]oct-3-yl]-4-(2-cyanopyridin-4-yloxy)-benzamide; N-[(3R)-1-azabicyclo[2.2:2]oct-3-yl]-4-(2-morpholin-4-yl-pyridin-4-yloxy)-benzamide; N-[(3R)-1-azabicyclo[2.2.2]oct-3-yl]-4-(5-methylpyridin-2-yloxy)-benzamide; N-[(3R)-1-azabicyclo[2.2.2]oct-3-yl]-4-(5-chloropyridin-2-yloxy)-benzamide; N-[(3R)-1-azabicyclo[2.2.2]oct-3-yl]-4-(5-methoxypyridin-2- yloxy)-benzamide; N-[(3R)-1-azabicyclo[2.2.2]oct-3-yl]-4-(5-trifluoromethylpyridin-2-yloxy)-benzamide; N-[(3R)-1-azabicyclo[2.2.2]oct-3-yl]-4-(5-acetylpyridin-2-yloxy)-benzamide; N-[(3R)-1-azabicyclo[2.2.2]oct-3-yl]-4-(5-acetaminopyridin-2-yloxy)-benzamide; N-[(3R)-1-azabicyclo[2.2.2]oct-3-yl]-4-(5-cyanopyridin-2-yloxy)-benzamide; N-[(3R)-1-azabicyclo[2.2.2]oct-3-yl]-4-(5-morpholin-4-yl-pyridin-2-yloxy)-benzamide; N-[(3R)-1-azabicyclo[2.2.2]oct-3-yl]-4-(4-methylpyridin-2-yloxy)-benzamide; N-[(3R)-1-azabicyclo[2.2.2]oct-3-yl]-4-(4-chloropyridin-2-yloxy)-benzamide; N-[(3R)-1-azabicyclo[2.2.2]oct-3-yl]-4-(4-methoxypyridin-2-yloxy)-benzamide; N-[(3R)-1-azabicyclo[2.2.2]oct-3-yl]-4-(5-trifluoromethylpyridin-2-yloxy)-benzamide; N-[(3R)-1-azabicyclo[2.2.2]oct-3-yl]-4-(4-acetylpyridin-2-yloxy)-benzamide; N-[(3R)-1-azabicyclo[2.2.2]oct-3-yl]-4-(4-acetaminopyridin-2-yloxy)-benzamide; N-[(3R)-1-azabicyclo[2.2.2]oct-3-yl]-4-(4-cyanopyridin-2-yloxy)-benzamide; N-[(3R)-1-azabicyclo[2.2.2]oct-3-yl]-4-(4-morpholin-4-yl-pyridin-2-yloxy)-benzamide; N-[(3R)-1-azabicyclo[2.2.2]oct-3-yl]-4-(6-methylpyridin-2-yloxy)-benzamide; N-[(3R)-1-azabicyclo[2.2.2]oct-3-yl]-4-(6-chloropyridin-2-yloxy)-benzamide; N-[(3R)-1-azabicyclo[2.2.2]oct-3-yl]-4-(6-methoxypyridin-2-yloxy)-benzamide; N-[(3R)-1-azabicyclo[2.2.2]oct-3-yl]-4-(6-trifluoromethylpyridin-2-yloxy)-benzamide; N-[(3R)-1-azabicyclo[2.2.2]oct-3-yl]-4-(6-acetylpyridin-2-yloxy)-benzamide; N-[(3R)-1-azabicyclo[2.2.2]oct-3-yl]-4-(6-acetaminopyridin-2-yloxy)-benzamide; N-[(3R)-1-azabicyclo[2.2.2]oct-3-yl]-4-(6-cyanopyridin-2-yloxy)-benzamide; N-[(3R)-1-azabicyclo[2.2.2]oct-3-yl]-4-(6-morpholin-4-yl-pyridin-2-yloxy)-benzamide; N-[(3R)-1-azabicyclo[2.2.2]oct-3-yl]-4-(5-methylpyridin-3-yloxy)-benzamide; N-[(3R)-1-azabicyclo[2.2.2]oct-3-yl]-4-(5-chloropyridin-3-yloxy)-benzamide; N-[(3R)-1-azabicyclo[2.2.2]oct-3-yl]-4-(5-methoxypyridin-3-yloxy)-benzamide; N-[(3R)-1-azabicyclo[2.2.2]oct-3-yl]-4-(5-trifluoromethylpyridin-3-yloxy)-benzamide; N-[(3R)-1-azabicyclo[2.2.2]oct-3-yl]-4-(5-acetylpyridin-3-yloxy)-benzamide; N-[(3R)-1-azabicyclo[2.2.2]oct-3-yl]-4-(5-acetaminopyridin-3-yloxy)-benzamide; N-[(3R)-1-azabicyclo[2.2.2]oct-3-yl]-4-(5-cyanopyridin-3-yloxy)-benzamide; N-[(3R)-1-azabicyclo[2.2.2]oct-3-yl]-4-(5-morpholin-4-yl-pyridin-3-yloxy)-benzamide; N-[(3R)-1-azabicyclo[2.2.2]oct-3-yl]-4-(2-chloropyridin-3-yloxy)-benzamide; N-[(3R)-1-azabicyclo[2.2.2]oct-3-yl]-4-(4-chloropyridin-3-yloxy)-benzamide; N-[(3R)-1-azabicyclo[2.2.2]oct-3-yl]-4-(3-chloropyridin-4-yloxy)-benzamide; N-[(3R)-1-azabicyclo[2.2.2]oct-3-yl]-4-(3-chloropyridin-2-yloxy)-benzamide; N-[(3R)-1-azabicyclo[2.2.2]oct-3-yl]-4-(6-methylpyridin-3-ylsulfanyl)-benzamide; N-[(3R)-1-azabicyclo[2.2.2]oct-3-yl]-4-(6-chloropyridin-3-ylsulfanyl)-benzamide; N-[(3R)-1-azabicyclo[2.2.2]oct-3-yl]-4-(6-methoxypyridin-3-ylsulfanyl)-benzamide; N-[(3R)-1-azabicyclo[2.2.2]oct-3-yl]-4-(6-trifluoromethylpyridin-3-ylsulfanyl)-benzamide; N-[(3R)-1-azabicyclo[2.2.2]oct-3-yl]-4-(6-acetylpyridin-3-ylsulfanyl)-benzamide; N-[(3R)-1-azabicyclo[2.2.2]oct-3-yl]-4-(6-acetaminopyridin-3-ylsulfanyl)-benzamide; N-[(3R)-1-azabicyclo[2.2.2]oct-3-yl]-4-(6cyanopyridin-3-ylsulfanyl)-benzamide; N-[(3R)-1-azabicyclo[2.2.2]oct-3-yl]-4-(6-morpholin-4-yl-pyridin-3-ylsulfanyl)-benzamide; N-[(3R)-1-azabicyclo[2.2.2]oct-3-yl]-4-(2-methylpyridin-ylsulfanyl)-benzamide; N-[(3R)-1-azabicyclo[2.2.2]oct-3-yl]-4-(choropyridin-4-ylsulfanyl)-benzamide; N-[(3R)-1-azabicyclo[2.2.2]oct-3-yl]-4-(2-methoxypyridin-4-ylsulfanyl)-benzamide; N-[(3R)-1-azabicyclo[2.2.2]oct-3-yl]-4-(2-trifluoromethylpyridin-4-ylsulfanyl)-benzamide; N-[(3R)-1-azabicyclo[2.2.2]oct-3-yl]-4-(2-acetylpyridin-4-ylsulfanyl)-benzamide; N-[(3R)-1-azabicyclo[2.2.2]oct-3-yl]-4-(2-acetaminopyridin-4-ylsulfanyl)-benzamide; N-[(3R)-1-azabicyclo[2.2.2]oct-3-yl]-4-(2-cyanopyridin-4-ylsulfanyl)-benzamide; N-[(3R)-1-azabicyclo[2.2.2]oct-3-yl]-4-(2-morpholin-4-yl-pyridin-4-ylsulfanyl)-benzamide; N-[(3R)-1-azabicyclo[2.2.2]oct-3-yl]-4-(5-methylpyridin-2-ylsulfanyl)-benzamide; N-[(3R)-1-azabicyclo[2.2.2]oct-3-yl]-4-(5-chloropyridin-2-ylsulfanyl)-benzamide; N-[(3R)-1-azabicyclo[2.2.2]oct-3-yl]-4-(5-methoxypyridin-2-ylsulfanyl)-benzamide; N-[(3R)-1-azabicyclo[2.2.2]oct-3-yl]-4-(5-trifluoromethylpyridin-2-ylsulfanyl)-benzamide; N-[(3R)-1-azabicyclo[2.2.2]oct-3-yl]-4-(5-acetylpyridin-2-ylsulfanyl)-benzamide; N-[(3R)-1-azabicyclo[2.2.2]oct-3-yl]-4-(5-acetaminopyridin-2-ylsulfanyl)-benzamide; N-[(3R)-1-azabicyclo[2.2.2]oct-3-yl]-4-(5-cyanopyridin-2-ylsulfanyl)-benzamide; N-[(3R)-1-azabicyclo[2.2.2]oct-3-yl]-4-(5-morpholin-4-yl-pyridin-2-ylsulfanyl)-benzamide; N-[(3R)-1-azabicyclo[2.2.2]oct-3-yl]-4-(4-methylpyridin-2-ylsulfanyl)-benzamide; N-[(3R)-1-azabicyclo[2.2.2]oct-3-yl]-4-(4-chloropyridin-2-ylsulfanyl)-benzamide; N-[(3R)-1-azabicyclo[2.2.2]oct-3-yl]-4-(4-methoxypyridin-2-ylsulfanyl)-benzamide; N-[(3R)-1-azabicyclo[2.2.2]oct-3-yl]-4-(4-trifluoromethylpyridin-2-ylsulfanyl)-benzamide; N-[(3R)-1-azabicyclo[2.2.2]oct-3-yl]-4-(4-acetylpyridin-2-ylsulfanyl)-benzamide; N-[(3R)-1-azabicyclo[2.2.2]oct-3-yl]-4-(4-acetaminopyridin-2-ylsulfanyl)-benzamide; N-[(3R)-1-azabicyclo[2.2.2]oct-3-yl]-4-(4-cyanopyridin-2-ylsulfanyl)-benzamide; N-[(3R)-1-azabicyclo[2.2.2]oct-3-yl]-4-(4-morpholin-4-yl-pyridin-2-ylsulfanyl)-benzamide; N-[(3R)-1-azabicyclo[2.2.2]oct-3-yl]-4-(6-methylpyridin-2-ylsulfanyl)-benzamide; N-[(3R)-1-azabicyclo[2.2.2]oct-3-yl]-4-(6-chloropyridin-2-ylsulfanyl)-benzamide; N-[(3R)-1-azabicyclo[2.2.2]oct-3-yl]-4-(6-methoxypyridin-2-ylsulfanyl)-benzamide; N-[(3R)-1-azabicyclo[2.2.2]oct-3-yl]-4-(6-trifluororethylpyridin-2-ylsulfanyl)-benzamide; N-[(3R)-1-azabicyclo[2.2.2]oct-3-yl]-4-(6-acetylpyridin-2-ylsulfanyl)-benzamide; N-[(3R)-1-azabicyclo[2.2.2]oct-3-yl]-4-(6-acetaminopyridin-2-ylsulfanyl)-benzamide; N-[(3R)-1-azabicyclo[2.2.2]oct-3-yl]-4-(6-cyanopyridin-2-ylsulfanyl)-benzamide; N-[(3R)-1-azabicyclo[2.2.2]oct-3-yl]-4-(6-morpholin-4-yl-pyridin-2-ylsulfanyl)-benzamide; N-[(3R)-1-azabicyclo[2.2.2]oct-3-yl]-4-(5-methylpyridin-3-ylsulfanyl)-benzamide; N-[(3R)-1-azabicyclo[2.2.2]oct-3-yl]-4-(5-chloropyridin-3-ylsulfanyl)-benzamide; N-[(3R)-1-azabicyclo[2.2.2]oct-3-yl]-4-(5-methoxypyridin-3-ylsulfanyl)-benzamide; N-[(3R)-1-azabicyclo[2.2.2]oct-3-yl]-4-(5-trifluoromethylpyridin-3-ylsulfanyl)-benzamide; N-[(3R)-1-azabicyclo[2.2.2]oct-3-yl]-4-(5-acetylpyridin-3-ylsulfanyl)-benzamide; N-[(3R)-1-azabicyclo[2.2.2]oct-3-yl]-4-(5-acetaminopyridin-3-ylsulfanyl)-benzamide; N-[(3R)-1-azabicyclo[2.2.2]oct-3-yl]-4-(5-cyanopyridin-3-ylsulfanyl)-benzamide; N-[(3R)-1-azabicyclo[2.2.2]oct-3-yl]-4-(5-morpholin-4-yl-pyridin-3-ylsulfanyl)-benzamide; N-[(3R)-1-azabicyclo[2.2.2]oct-3-yl]-4-(2-chloropyridin-3-ylsulfanyl)-benzamide; N-[(3R)-1-azabicyclo[2.2.2]oct-3-yl]-4-(4-chloropyridin-3-ylsulfanyl)-benzamide; N-[(3R)-1-azabicyclo[2.2.2]oct-3-yl]-4-(3-chloropyridin-4-ylsulfanyl)-benzamide; N-[(3R)-1-azabicyclo[2.2.2]oct-3-yl]-4-(3-chloropyridin- 2-ylsulfanyl)-benzamide; N-[(2S,3R)-2-methyl-1-azabicyclo[2.2.2]oct-3-yl]-4-(4-aminophenoxy)-benzamide; N-[(2S,3R)-2-methyl-1-azabicyclo[2.2.2]oct-3-yl]-4-(3-aminophenoxy)-benzamide; N-[(2S,3R)-2-methyl-1-azabicyclo[2.2.2]oct-3-yl]-4-(2-aminophenoxy)-benzamide; N-[(2S,3R)-2-methyl-1-azabicyclo[2.2.2]oct-3-yl]-4-(4-methanesulfonylamino-phenoxy)-benzamide; N-[(2S,3R)-2-methyl-1-azabicyclo[2.2.2]oct-3-yl]-4-(3-methanesulfonylamino-phenoxy)-benzamide; N-[(2S,3R)-2-methyl-1-azabicyclo[2.2.2]oct-3-yl]-4-(2-methanesulfonylamino-phenoxy)-benzamide; N-[(2S,3R)-2-methyl-1-azabicyclo[2.2.2]oct-3-yl]-4-(4-acetoxyphenoxy)-benzamide; N-[(2S,3R)-2-methyl-1-azabicyclo[2.2.2]oct-3-yl]-4-(3-acetoxyphenoxy)-benzamide; N-[(2S,3R)-2-methyl-1-azabicyclo[2.2.2]oct-3-yl]-4-(2-acetoxyphenoxy)-benzamide; N-[(2S,3R)-2-methyl-1-azabicyclo[2.2.2]oct-3-yl]-4-(4-acetylphenoxy)-benzamide; N-[(2S,3R)-2-methyl-1-azabicyclo[2.2.2]oct-3-yl]-4-(3-acetylphenoxy)-benzamide; N-[(2S,3R)-2-methyl-1-azabicyclo[2.2.2]oct-3-yl]-4-(2-acetylphenoxy)-benzamide; N-[(2S,3R)-2-methyl-1-azabicyclo[2.2.2]oct-3-yl]-4-(4-carbamoylphenoxy)-benzamide; N-[(2S,3R)-2-methyl-1-azabicyclo[2.2.2]oct-3-yl]-4-(3-carbamoylphenoxy)-benzamide; N-[(2S,3R)-2-methyl-1-azabicyclo[2.2.2]oct-3-yl]-4-(2-carbamoylphenoxy)-benzamide; N-[(2S,3R)-2-methyl-1-azabicyclo[2.2.2]oct-3-yl]-4-(4-cyanophenoxy)-benzamide; N-[(2S,3R)-2-methyl-1-azabicyclo[2.2.2]oct-3-yl]-4-(3-cyanophenoxy)-benzamide; N-[(2S,3R)-2-methyl-1-azabicyclo[2.2.2]oct-3-yl]-4-(2-cyanophenoxy)-benzamide; N-[(2S,3R)-2-methyl-1-azabicyclo[2.2.2]oct-3-yl]-4-(4-sulfamoylphenoxy)-benzamide; N-[(2S,3R)-2-methyl-1-azabicyclo[2.2.2]oct-3-yl]-4-(3-sulfamoylphenoxy)-benzamide; N-[(2S,3R)-2-methyl-1-azabicyclo[2.2.2]oct-3-yl]-4-(2-sulfamoylphenoxy)-benzamide; N-[(2S,3R)-2-methyl-1-azabicyclo[2.2.2]oct-3-yl]-4-(thiophen-2-yloxy)-benzamide; N-[(2S,3R-)-2-methyl-1-azabicyclo[2.2.2]oct-3-yl]-4-(5-methylthiophen-2-yloxy)-benzamide; N-[(2S,3R)-2-methyl-1-azabicyclo[2.2.2]oct-3-yl]-4-(5-chlorothiophen-2-yloxy)-benzamide; N-[(2S,3R)-2-methyl-1-azabicyclo[2.2.2]oct-3-yl]-4-(5-methoxythiophen-2-yloxy)-benzamide; N-[(2S,3R)-2-methyl-1-azabicyclo[2.2.2]oct-3-yl]-4-(5-trifluoromethylthiophen-2-yloxy)-benzamide; N-[(2S,3R)-2-methyl-1-azabicyclo[2.2.2]oct-3-yl]-4-(5-acetylthiophen-2-yloxy)-benzamide; N-[(2S,3R)-2-methyl-1-azabicyclo[2.2.2]oct-3-yl]-4-(5-acetaminothiophen-2-yloxy)-benzamide; N-[(2S,3R)-2-methyl-1-azabicyclo[2.2.2]oct-3-yl]-4-(5-cyanothiophen-2-yloxy)-benzamide; N-[(2S,3R)-2-methyl-1-azabicyclo[2.2.2]oct-3-yl]-4-(5-morpholin-4-yl-thiophen-2-yloxy)-benzamide; N-[(2S,3R)-2-methyl-1-azabicyclo[2.2.2]oct-3-yl]-4-(4-methylthiophen-2-yloxy)-benzamide; N-[(2S,3R)-2-methyl-1-azabicyclo[2.2.2]oct-3-yl]-4-(4-chlorothiophen-2-yloxy)-benzamide; N-[(2S,3R)-2-methyl-1-azabicyclo[2.2.2]oct-3-yl]-4-(4-methoxythiophen-2-yloxy)-benzamide; N-[(2S,3R)-2-methyl-1-azabicyclo[2.2.2]oct-3-yl]-4-(4-trifluoromethylthiophen-2-yloxy)-benzamide; N-[(2S,3R)-2-methyl-1-azabicyclo[2.2.2]oct-3-yl]-4-(4-acetylthiophen-2-yloxy)-benzamide; N-[(2S,3R)-2-methyl-1-azabicyclo[2.2.2]oct-3-yl]-4-(4-acetaminothiophen-2-yloxy)-benzamide; N-[(2S,3R)-2-methyl-1-azabicyclo[2.2.2]oct-3-yl]-4-(4-cyanothiophen-2-yloxy)-benzamide; N-[(2S,3R)-2-methyl-1-azabicyclo[2.2.2]oct-3-yl]-4-(4-morpholin-4-yl-thiophen-2-yloxy)-benzamide; N-[(2S,3R)-2-methyl-1-azabicyclo[2.2.2]oct-3-yl]-4-(furan-2-yloxy)-benzamide; N-[(2S,3R)-2-methyl-1-azabicyclo[2.2.2]oct-3-yl]-4-(5-methylfuran-2-yloxy)-benzamide; N-[(2S,3R)-2-methyl-1-azabicyclo[2.2.2]oct-3-yl]-4-(5-chlorofuran-2-yloxy)-benzamide; N-[(2S,3R)-2-methyl-1-azabicyclo[2.2.2]oct-3-yl]-4-(5-methoxyfuran-2-yloxy)-benzamide; N-[(2S,3R)-2-methyl-1-azabicyclo[2.2.2]oct-3-yl]-4-(5-trifluoromethylfuran-2-yloxy)-benzamide; N-[(2S,3R)-2-methyl-1-azabicyclo[2.2.2]oct-3-yl]-4-(5-acetylfuran-2-yloxy)-benzamide; N-[(2S,3R)-2-methyl-1-azabicyclo[2.2.2]oct-3-yl]-4-(5-acetaminofuran-2-yloxy)-benzamide; N-[(2S,3R)-2-methyl-1-azabicyclo[2.2.2]oct-3-yl]-4-(5-cyanofuran-2-yloxy)-benzamide; N-[(2S,3R)-2-methyl-1-azabicyclo[2.2.2]oct-3-yl]-4-(5-morpholin-4-yl-furan-2-yloxy)-benzamide; N-[(2S,3R)-2-methyl-1-azabicyclo[2.2.2]oct-3-yl]-4-(4-methylfuran-2-yloxy)-benzamide; N-[(2S,3R)-2-methyl-1-azabicyclo[2.2.2]oct-3-yl]-4-(4-chlorofuran-2-yloxy)-benzamide; N-[(2S,3R)-2-methyl-1-azabicyclo[2.2.2]oct-3-yl]-4-(4-methoxyfuran-2-yloxy)-benzamide; N-[(2S,3R)-2-methyl-1-azabicyclo[2.2.2]oct-3-yl]-4-(4-trifluoromethylfuran-2-yloxy)-benzamide; N-[(2S,3R)-2-methyl-1-azabicyclo[2.2.2]oct-3-yl]-4-(4-acetylfuran-2-yloxy)-benzamide; N-[(2S,3R)-2-methyl-1-azabicyclo[2.2.2]oct-3-yl]-4-(4-acetaminofuran-2-yloxy)-benzamide; N-[(2S,3R)-2-methyl-1-azabicyclo[2.2.2]oct-3-yl]-4-(4-cyanofuran-2-yloxy)-benzamide; N-[(2S,3R)-2-methyl-1-azabicyclo[2.2.2]oct-3-yl]-4-(4-morpholin-4-yl-furan-2-yloxy)-benzamide; N-[(2S,3R)-2-methyl-1-azabicyclo[2.2.2]oct-3-yl]-4-(oxazol-2-yloxy)-benzamide; N-[(2S,3R)-2-methyl-1-azabicyclo[2.2.2]oct-3-yl]-4-(5-methyloxazol-2-yloxy)-benzamide; N-[(2S,3R)-2-methyl-1-azabicyclo[2.2.2]oct-3-yl]-4-(5-chlorooxazol-2-yloxy)-benzamide; N-[(2S,3R)-2-methyl-1-azabicyclo[2.2.2]oct-3-yl]-4-(5-methoxyoxazol-2-yloxy)-benzamide; N-[(2S,3R)-2-methyl-1-azabicyclo[2.2.2]oct-3-yl]-4-(5-trifluoromethyloxazol-2-yloxy)-benzamide; N-[(2S,3R)-2-methyl-1-azabicyclo[2.2.2]oct-3-yl]-4-(5-acetyloxazol-2-yloxy)-benzamide; N-[(2S,3R)-2-methyl-1-azabicyclo[2.2.2]oct-3-yl]-4-(5-acetaminooxazol-2-yloxy)-benzamide; N-[(2S,3R)-2-methyl-1-azabicyclo[2.2.2]oct-3-yl]-4-(5-cyanooxazol-2-yloxy)-benzamide; N-[(2S,3R)-2-methyl-1-azabicyclo[2.2.2]oct-3-yl]-4-(5-morpholin-4-yl-oxazol-2-yloxy)-benzamide; N-[(2S,3R)-2-methyl-1-azabicyclo[2.2.2]oct-3-yl]-4-(oxazol-2-yloxy)-benzamide; N-[(2S,3R)-2-methyl-1-azabicyclo[2.2.2]oct-3-yl]-4-(4-methyloxazol-2-yloxy)-benzamide; N-[(2S,3R)-2-methyl-1-azabicyclo[2.2.2]oct-3-yl]-4-(4-chlorooxazol-2-yloxy)-benzamide; N-[(2S,3R)-2-methyl-1-azabicyclo[2.2.2]oct-3-yl]-4-(4-methoxyoxazol-2-yloxy)-benzamide; N-[(2S,3R)-2-methyl-1-azabicyclo[2.2.2]oct-3-yl]-4-(4-trifluoromethyloxazol-2-yloxy)-benzamide; N-[(2S,3R)-2-methyl-1-azabicyclo[2.2.2]oct-3-yl]-4-(4-acetyloxazol-2-yloxy)-benzamide; N-[(2S,3R)-2-methyl-1-azabicyclo[2.2.2]oct-3-yl]-4-(4-acetaminooxazol-2-yloxy)-benzamide; N-[(2S,3R)-2-methyl-1-azabicyclo[2.2.2]oct-3-yl]-4-(4-cyanooxazol-2-yloxy)-benzamide; N-[(2S,3R)-2-methyl-1-azabicyclo[2.2.2]oct-3-yl]-4-(4-morpholin-4-yl-oxazol-2-yloxy)-benzamide; N-[(2S,3R)-2-methyl-1-azabicyclo[2.2.2]oct-3-yl]-4-(oxazol-5-yloxy)-benzamide; N-[(2S,3R)-2-methyl-1-azabicyclo[2.2.2]oct-3-yl]-4-(2-methyloxazol-5-yloxy)-benzamide; N-[(2S,3R)-2-methyl-1-azabicyclo[2.2.2]oct-3-yl]-4-(2-chlorooxazol-5-yloxy)-benzamide; N-[(2S,3R)-2-methyl-1-azabicyclo[2.2.2]oct-3-yl]-4-(2-methoxyoxazol-5- yloxy)-benzamide; N-[(2S,3R)-2-methyl-1-azabicyclo[2.2.2]oct-3-yl]-4-(2-trifluoromethyloxazol-5-yloxy)-benzamide; N-[(2S,3R)-2-methyl-1-azabicyclo[2.2.2]oct-3-yl]-4-(2-acetyloxazol-5-yloxy)-benzamide; N-[(2S,3R)-2-methyl-1-azabicyclo[2.2.2]oct-3-yl]-4-(2-acetaminooxazol-5-yloxy)-benzamide; N-[(2S,3R)-2-methyl-1-azabicyclo[2.2.2]oct-3-yl]-4-(2-cyanooxazol-5-yloxy)-benzamide; N-[(2S,3R)-2-methyl-1-azabicyclo[2.2.2]oct-3-yl]-4-(2-morpholin-4-yl-oxazol-5-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4-(5-methylthiazol-2-yloxy)-benzamide; N-[(2S,3R)-2-methyl-1-azabicyclo[2.2.2]oct-3-yl]-4-(5-chlorothiazol-2-yloxy)-benzamide; N-[(2S,3R)-2-methyl-1-azabicyclo[2.2.2]oct-3-yl]-4-(5-methoxythiazol-2-yloxy)-benzamide; N-[(2S,3R)-2-methyl-1-azabicyclo[2.2.2]oct-3-yl]-4-(5-trifluoromethylthiazol-2-yloxy)-benzamide; N-[(2S,3R)-2-methyl-1-azabicyclo[2.2.2]oct-3-yl]-4-(5-acetylthiazol-2-yloxy)-benzamide; N-[(2S,3R)-2-methyl-1-azabicyclo[2.2.2]oct-3-yl]-4-(5-acetaminothiazol-2-yloxy)-benzamide; N-[(2S,3R)-2-methyl-1-azabicyclo[2.2.2]oct-3-yl]-4-(5-cyanothiazol-2-yloxy)-benzamide; N-[(2S,3R)-2-methyl-1-azabicyclo[2.2.2]oct-3-yl]-4-(5-morpholin-4-yl-thiazol-2-yloxy)-benzamide; N-[(2S,3R)-2-methyl-1-azabicyclo[2.2.2]oct-3-yl]-4-(thiazol-2-yloxy)-benzamide; N-[(2S,3R)-2-methyl-1-azabicyclo[2.2.2]oct-3-yl]-4-(4-methylthiazol-2-yloxy)-benzamide; N-[(2S,3R)-2-methyl-1-azabicyclo[2.2.2]oct-3-yl]-4-(4-chlorothiazol-2-yloxy)-benzamide; N-[(2S,3R)-2-methyl-1-azabicyclo[2.2.2]oct-3-yl]-4-(4-methoxythiazol-2-yloxy)-benzamide; N-[(2S,3R)-2-methyl-1-azabicyclo[2.2.2]oct-3-yl]-4-(4-trifluoromethylthiazol-2-yloxy)-benzamide; N-[(2S,3R)-2-methyl-1-azabicyclo[2.2.2]oct-3-yl]-4-(4-acetylthiazol-2-yloxy)-benzamide; N-[(2S,3R) 2-methyl-1-azabicyclo[2.2.2]oct-3-yl]-4-(4-acetaminothiazol-2-yloxy)-benzamide; N-[(2S,3R)-2-methyl-1-azabicyclo[2.2.2]oct-3-yl]-4-(4-cyanothiazol-2-yloxy)-benzamide ; N-[(2S,3R)-2-methyl-1-azabicyclo[2.2.2]oct-3-yl]-4-(4-morpholin-4-yl-thiazol-2-yloxy)-benzamide; N-[(2S,3R)-2-methyl-1-azabicyclo[2.2.2]oct-3-yl]-4-(thiazol-5-yloxy)-benzamide; N-[(2S,3R)-2-methyl-1-azabicyclo[2.2.2]oct-3-yl]-4-(2-methylthiazol-5-yloxy)-benzamide; N-[(2S,3R)-2-methyl-1-azabicyclo[2.2.2]oct-3-yl]-4-(2-chlorothiazol-5-yloxy)-benzamide; N-[(2S,3R)-2-methyl-1-azabicyclo[2.2.2]oct-3-yl]-4-(2-methoxythiazol-5-yloxy)-benzamide; N-[(2S,3R)-2-methyl-1-azabicyclo[2.2.2]oct-3-yl]-4-(2-trifluoromethylthiazol-5-yloxy)-benzamide; N-[(2S,3R)-2-methyl-1-azabicyclo[2.2.2]oct-3-yl]-4-(2-acetylthiazol-5-yloxy)-benzamide; N-[(2S,3R)-2-methyl-1-azabicyclo[2.2.2]oct-3-yl]-4-(2-acetaminothiazol-5-yloxy)-benzamide; N-[(2S,3R)-2-methyl-1-azabicyclo[2.2.2]oct-3-yl]-4-(2-cyanothiazol-5-yloxy)-benzamide; N-[(2S,3R)-2-methyl-1-azabicyclo[2.2.2]oct-3-yl]-4-(2-morpholin-4-yl-thiazol-5-yloxy)-benzamide; N-[(2S,3R)-2-methyl-1-azabicyclo[2.2.2]oct-3-yl]-4-([1,3,4]oxadiazol-2-yloxy)-benzamide; N-[(2S,3R)-2-methyl-1-azabicyclo[2.2.2]oct-3-yl]-4-(5-methyl[1,3,4]oxadiazol-2-yloxy)-benzamide; N-[(2S,3R)-2-methyl-1-azabicyclo[2.2.2]oct-3-yl]-4-(5-chloro[1,3,4]oxadiazol-2-yloxy)-benzamide; N-[(2S,3R)-2-methyl-1-azabicyclo[2.2.2]oct-3-yl]-4-(5-methoxy[1,3,4]oxadiazol-2-yloxy)-benzamide; N-[(2S,3R)-2-methyl-1-azabicyclo[2.2.2]oct-3-yl]-4-(5-trifluoromethyl[1,3,4]oxadiazol-2-yloxy)-benzamide; N-[(2S,3R)-2-methyl-1-azabicyclo[2.2.2]oct-3-yl]-4-(5-acetyl[1,3,4]oxadiazol-2-yloxy)-benzamide; N-[(2S,3R)-2-methyl-1-azabicyclo[2.2.2]oct-3-yl]-4-(5-acetamino[1,3,4]oxadiazol-2-yloxy)-benzamide; N-[(2S,3R)-2-methyl-1-azabicyclo[2.2.2]oct-3-yl]-4-(5-cyano[1,3,4]oxadiazol-2-yloxy)-benzamide; N-[(2S,3R)-2-methyl-1-azabicyclo[2.2.2]oct-3-yl]-4-(5-morpholin-4-yl-[1,3,4]oxadiazol-2-yloxy)-benzamide; N-[(2S,3R)-2-methyl-1-azabicyclo[2.2.2]oct-3-yl]-4-([1,3,4]thiadiazol-2yloxy)-benzamide; N-[(2S,3R)-2-methyl-1-azabicyclo[2.2.2]oct-3-yl]-4-(5-methyl[1,3,4]thiadiazol-2-yloxy)-benzamide; N-[(2S,3R)-2-methyl-1-azabicyclo[2.2.2]oct-3-yl]-4-(5-chloro[1,3,4]thiadiazol-2-yloxy)-benzamide; N-[(2S,3R)-2-methyl-1-azabicyclo[2.2.2]oct-3-yl]-4-(5-methoxy[1,3,4]thiadiazol-2-yloxy)-benzamide; N-[(2S,3R)-2-methyl-1-azabicyclo[2.2.2]oct-3-yl]-4-(5-trifluoromethyl[1,3,4]thiadiazol-2-yloxy)-benzamide; N-[(2S,3R)-2-methyl-1-azabicyclo[2.2.2]oct-3-yl]-4-(5-acetyl[1,3,4]thiadiazol-2-yloxy)-benzamide; N-[(2S,3R)-2-methyl-1-azabicyclo[2.2.2]oct-3-yl]-4-(5-acetamino[1,3,4]thiadiazol-2-yloxy)-benzamide; N-[(2S,3R)-2-methyl-1-azabicyclo[2.2.2]oct-3-yl]-4-(5-cyano[1,3,4]thiadiazol-2-yloxy)-benzamide; N-[(2S,3R)-2-methyl-1-azabicyclo[2.2.2]oct-3-yl]-4-(5-morpholin-4-yl-[1,3,4]thiadiazol-2-yloxy)-benzamide; N-[(2S,3R)-2-methyl-1-azabicyclo[2.2.2]oct-3-yl]-4-(4-aminophenylsulfanyl)-benzamide; N-[(2S,3R)-2-methyl-1-azabicyclo[2.2.2]oct-3-yl]-4-(3-aminophenylsulfanyl)-benzamide; N-[(2S,3R)-2-methyl-1-azabicyclo[2.2.2]oct-3-yl]-4-(2-aminophenylsulfanyl)-benzamide; N-[(2S,3R)-2-methyl-1-azabicyclo[2.2.2]oct-3-yl]-4-(4-methanesulfonylamino-phenylsulfanyl)-benzamide; N-[(2S,3R)-2-methyl-1-azabicyclo[2.2.2]oct-3-yl]-4-(3-methanesulfonylamino-phenylsulfanyl)-benzamide; N-[(2S,3R)-2-methyl-1-azabicyclo[2.2.2]oct-3-yl]-4-(2-methanesulfonylamino-phenylsulfanyl)-benzamide; N-[(2S,3R)-2-methyl-1-azabicyclo[2.2.2]oct-3-yl]-4-(4-acetoxyphenylsulfanyl)-benzamide; N-[(2S,3R)-2-methyl-1-azabicyclo[2.2.2]oct-3-yl]-4-(3-acetoxyphenylsulfanyl)-benzamide; N-[(2S,3R)-2-methyl-1-azabicyclo[2.2.2]oct-3-yl]-4-(2-acetoxyphenylsulfanyl)-benzamide; N-[(2S,3R)-2-methyl-1-azabicyclo[2.2.2]oct-3-yl]-4-(4-acetylphenylsulfanyl)-benzamide; N-[(2S,3R)-2-methyl-1-azabicyclo[2.2.2]oct-3-yl]-4-(3-acetylphenylsulfanyl)-benzamide; N-[(2S,3R)-2-methyl-1-azabicyclo[2.2.2]oct-3-yl]-4-(2-acetylphenylsulfanyl)-benzamide; N-[(2S,3R)-2-methyl-1-azabicyclo[2.2.2]oct-3-yl]-4-(4-carbamoylphenylsulfanyl)-benzamide; N-[(2S,3R)-2-methyl-1-azabicyclo[2.2.2]oct-3-yl]-4-(3-carbamoylphenylsulfanyl)-benzamide; N-[(2S,3R)-2-methyl-1-azabicyclo[2.2.2]oct-3-yl]-4-(2-carbamoylphenylsulfanyl)-benzamide; N-[(2S,3R)-2-methyl-1-azabicyclo[2.2.2]oct-3-yl]-4-(4-cyanophenylsulfanyl)-benzamide; N-[(2S,3R)-2-methyl-1-azabicyclo[2.2.2]oct-3-yl]-4-(3-cyanophenylsulfanyl)-benzamide; N-[(2S,3R)-2-methyl-1-azabicyclo[2.2.2]oct-3-yl]4(2-cyanophenylsulfanyl)-benzamide; N-[(2S,3R)-2-methyl-1-azabicyclo[2.2.2]oct-3-yl]-4-(4-sulfamoylphenylsulfanyl)-benzamide; N-[(2S,3R)-2-methyl-1-azabicyclo[2.2.2]oct-3-yl]-4-(3-sulfamoylphenylsulfanyl)-benzamide; N-[(2S,3R)-2-methyl-1-azabicyclo[2.2.2]oct-3-yl]-4-(2-sulfamoylphenylsulfanyl)-benzamide; N-[(2S,3R)-2-methyl-1-azabicyclo[2.2.2]oct-3-yl]-4-(4-hydroxyphenylsulfanyl)-benzamide; N-[(2S,3R)-2-methyl-1-azabicyclo[2.2.2]oct-3-yl]-4-(3-hydroxyphenylsulfanyl)-benzamide; N-[(2S,3R)-2-methyl-1-azabicyclo[2.2.2]oct-3-yl]-4-(2- hydroxyphenylsulfanyl)-benzamide; N-[(2S,3R)-2-methyl-1-azabicyclo[2.2.2]oct-3-yl]-4-(4-acetamidophenylsulfanyl)-benzamide; N-[(2S,3R)-2-methyl-1-azabicyclo[2.2.2]oct-3-yl]-4-(3-acetamidophenylsulfanyl)-benzamide; N-[(2S,3R)-2-methyl-1-azabicyclo[2.2.2]oct-3-yl]-4-(2-acetamidophenylsulfanyl)-benzamide; N-[(2S,3R)-2-methyl-1-azabicyclo[2.2.2]oct-3-yl]-4-(thiophen-2-ylsulfanyl)-benzamide; N-[(2S,3R)-2-methyl-1-azabicyclo[2.2.2]oct-3-yl]-4-(5-methylthiophen-2-ylsulfanyl)-benzamide; N-[(2S,3R)-2-methyl-1-azabicyclo[2.2.2]oct-3-yl]-4-(5-chlorothiophen-2-ylsulfanyl)-benzamide; N-[(2S,3R)-2-methyl-1-azabicyclo[2.2.2]oct-3-yl]-4-(5-methoxythiophen-2-ylsulfanyl)-benzamide; N-[(2S,3R)-2-methyl-1-azabicyclo[2.2.2]oct-3-yl]-4-(5-trifluoromethylthiophen-2-ylsulfanyl)-benzamide; N-[(2S,3R)-2-methyl-1-azabicyclo[2.2.2]oct-3-yl]-4-(5-acetylthiophen-2-ylsulfanyl)-benzamide; N-[(2S,3R)-2-methyl-1-azabicyclo[2.2.2]oct-3-yl]-4-(5-acetaminothiophen-2-ylsulfanyl)-benzamide; N-[(2S,3R)-2-methyl-1-azabicyclo[2.2.2]oct-3-yl]-4-(5-cyanothiophen-2-ylsulfanyl)-benzamide; N-[(2S,3R)-2-methyl-1-azabicyclo[2.2.2]oct-3-yl]-4-(5-morpholin-4-yl-thiophen-2-ylsulfanyl)-benzamide; N-[(2S,3R)-2-methyl-1-azabicyclo[2.2.2]oct-3-yl]-4-(4-methylthiophen-2-ylsulfanyl)-benzamide; N-[(2S,3R)-2-methyl-1-azabicyclo[2.2.2]oct-3-yl]-4-(4-chlorothiophen-2-ylsulfanyl)-benzamide; N-[(2S,3R)-2-methyl-1-azabicyclo[2.2.2]oct-3-yl]-4-(4-methoxythiophen-2-ylsulfanyl)-benzamide; N-[(2S,3R)-2-methyl-1-azabicyclo[2.2.2]oct-3-yl]-4-(4-trifluoromethylthiophen-2-ylsulfanyl)-benzamide; N-[(2S,3R)-2-methyl-1-azabicyclo[2.2.2]oct-3-yl]-4-(4-acetylthiophen-2-benzamide; N-[(2S,3R)-2-methyl-1-azabicyclo[2.2.2]oct-3-yl]-4-(4-acetaminothiophen-2-ylsulfanyl)-benzamide; N-[(2S,3R)-2-methyl-1-azabicyclo[2.2.2]oct-3-yl]-4-(4-cyanothiophen-2-ylsulfanyl)-benzamide; N-[(2S,3R)-2-methyl-1-azabicyclo[2.2.2]oct-3-yl]-4-(4-morpholin-4-yl-thiophen-2-ylsulfanyl)-benzamide; N-[(2S,3R)-2-methyl-1-azabicyclo[2.2.2]oct-3-yl]-4-(furan-2-ylsulfanyl)-benzamide; N-[(2S,3R)-2-methyl-1-azabicyclo[2.2.2]oct-3-yl]-4-(5-methylfuran-2-ylsulfanyl)-benzamide; N-[(2S,3R)-2-methyl-1-azabicyclo[2.2.2]oct-3-yl]-4-(5-chlorofuran-2-ylsulfanyl)-benzamide; N-[(2S,3R)-2-methyl-1-azabicyclo[2.2.2]oct-3-yl]-4-(5-methoxyfuran-2-ylsulfanyl)-benzamide; N-[(2S,3R)-2-methyl-1-azabicyclo[2.2.2]oct-3-yl]-4-(5-trifluoromethylfuran-2-ylsulfanyl)-benzamide; N-[(2S,3R)-2-methyl-1-azabicyclo[2.2.2]oct-3-yl]-4-(5-acetylfuran-2-ylsulfanyl)-benzamide; N-[(2S,3R)-2-methyl-1-azabicyclo[2.2.2]oct-3-yl]-4-(5-acetaminofuran-2-ylsulfanyl)-benzamide; N-[(2S,3R)-2-methyl-1-azabicyclo[2.2.2]oct-3-yl]-4-(5-cyanofuran-2-ylsulfanyl)-benzamide; N-[(2S,3R)-2-methyl-1-azabicyclo[2.2.2]oct-3-yl]-4-(5-morpholin-4-yl-furan-2-ylsulfanyl)-benzamide; N-[(2S,3R)-2-methyl-1-azabicyclo[2.2.2]oct-3-yl]-4-(4-methylfuran-2-ylsulfanyl)-benzamide; N-[(2S,3R)-2-methyl-1-azabicyclo[2.2.2]oct-3-yl]-4-(4-chlorofuran-2-ylsulfanyl)-benzamide; N-[(2S,3R)-2-methyl-1-azabicyclo[2.2.2]oct-3-yl]-4-(4-methoxyfuran-2-ylsulfanyl)-benzamide; N-[(2S,3R)-2-methyl-1-azabicyclo[2.2.2]oct-3-yl]-4-(4-trifluoromethylfuran-2-ylsulfanyl)-benzamide; N-[(2S,3R)-2-methyl-1-azabicyclo[2.2.2]oct-3-yl]-4-(4-acetylfuran-2-ylsulfanyl)-benzamide; N-[(2S,3R)-2-methyl-1-azabicyclo[2.2.2]oct-3-yl]-4-(4-acetaminofuran-2-ylsulfanyl)-benzamide; N-[(2S,3R)-2-methyl-1-azabicyclo[2.2.2]oct-3-yl]-4-(4-cyanofuran-2-ylsulfanyl)-benzamide; N-[(2S,3R)-2-methyl-1-azabicyclo[2.2.2]oct-3-yl]-4-(4-morpholin-4-yl-furan-2-ylsulfanyl)-benzamide; N-[(2S,3R)-2-methyl-1-azabicyclo[2.2.2]oct-3-yl]-4-(oxazol-2-ylsulfanyl)-benzamide; N-[(2S,3R)-2-methyl-1-azabicyclo[2.2.2]oct-3-yl]-4-(5-methyloxazol-2-ylsulfanyl)-benzamide; N-[(2S,3R)-2-methyl-1-azabicyclo[2.2.2]oct-3-yl]-4-(5-chlorooxazol-2-ylsulfanyl)-benzamide; N-[(2S,3R)-2-methyl-1-azabicyclo[2.2.2]oct-3-yl]-4-(5-methoxyoxazol-2-ylsulfanyl)-benzamide; N-[(2S,3R)-2-methyl-1-azabicyclo[2.2.2]oct-3-yl]-4-(5-trifluoromethyloxazol-2-ylsulfanyl)-benzamide; N-[(2S,3R)-2-methyl-1-azabicyclo[2.2.2]oct-3-yl]-4-(5-acetyloxazol-2-ylsulfanyl)-benzamide; N-[(2S,3R)-2-methyl-1-azabicyclo[2.2.2]oct-3-yl]-4-(5-acetaminooxazol-2-ylsulfanyl)-benzamide; N-[(2S,3R)-2-methyl-1-azabicyclo[2.2.2]oct-3-yl]-4-(5-cyanooxazol-2-ylsulfanyl)-benzamide; N-[(2S,3R)-2-methyl-1-azabicyclo[2.2.2]oct-3-yl]-4-(5-morpholin-4-yl-oxazol-2-ylsulfanyl)-benzamide; N-[(2S,3R)-2-methyl-1-azabicyclo[2.2.2]oct-3-yl]-4-(oxazol-2-ylsulfanyl)-benzamide; N-[(2S,3R)-2-methyl-1-azabicyclo[2.2.2]oct-3-yl]-4-(4-methyloxazol-2-ylsulfanyl)-benzamide; N-[(2S,3R)-2-methyl-1-azabicyclo[2.2.2]oct-3-yl]-4-(4-chlorooxazol-2-ylsulfanyl)-benzamide; N-[(2S,3R)-2-methyl-1-azabicyclo[2.2.2]oct-3-yl]-4-(4-methoxyoxazol-2-ylsulfanyl)-benzamide; N-[(2S,3R)-2-methyl-1-azabicyclo[2.2.2]oct-3-yl]-4-(4-trifluoromethyloxazol-2-ylsulfanyl)-benzamide; N-[(2S,3R)-2-methyl-1-azabicyclo[2.2.2]oct-3-yl]-4-(4-acetyloxazol-2-ylsulfanyl)-benzamide; N-[(2S,3R)-2-methyl-azabicyclo[2.2.2]oct-3-yl]-4-(4-acetaminooxazol-2-ylsulfanyl)-benzamide; N-[(2S,3R)-2-methyl-1-azabicyclo[2.2.2]oct-3-yl]-4-(4-cyanooxazol-2-ylsulfanyl)-benzamide; N-[(2S,3R)-2-methyl-1-azabicyclo[2.2.2]oct-3-yl]-4-(4-morpholin-4-yl-oxazol-2-ylsulfanyl)-benzamide; N-[(2S,3R)-2-methyl-1-azabicyclo[2.2.2]oct-3-yl]-4-(oxazol-5-ylsulfanyl)-benzamide; N-[(2S,3R)-2-methyl-1-azabicyclo[2.2.2]oct-3-yl]-4-(2-methyloxazol-5-ylsulfanyl)-benzamide; N-[(2S,3R)-2-methyl-1-azabicyclo[2.2.2]oct-3-yl]-4-(2-chlorooxazol-5-ylsulfanyl)-benzamide; N-[(2S,3R)-2-methyl-1-azabicyclo[2.2.2]oct-3-yl]-4-(2-methoxyoxazol-5-ylsulfanyl)-benzamide; N-[(2S,3R)-2-methyl-1-azabicyclo[2.2.2]oct-3-yl]-4-(2-trifluoromethyloxazol-5-ylsulfanyl)-benzamide; N-[(2S,3R)-2-methyl-1-azabicyclo[2.2.2]oct-3-yl]-4-(2-acetyloxazol-5-ylsulfanyl)-benzamide; N-[(2S,3R)-2-methyl-1-azabicyclo[2.2.2]oct-3-yl]-4-(2-acetaminooxazol-5-ylsulfanyl)-benzamide; N-[(2S,3R)-2-methyl-1-azabicyclo[2.2.2]oct-3-yl]-4-(2-cyanooxazol-5-ylsulfanyl)-benzamide; N-[(2S,3R)-2-methyl-1-azabicyclo[2.2.2]oct-3-yl]-4-(2-morpholin-4-yl-oxazol-5-ylsulfanyl)-benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(5-methylthiazol-2-ylsulfanyl)-benzamide; N-[(2S,3R)-2-methyl-1-azabicyclo[2.2.2]oct-3-yl]-4-(5-chlorothiazol-2-ylsulfanyl)-benzamide; N-[(2S,3R)-2-methyl-1-azabicyclo[2.2.2]oct-3-yl]-4-(5-methoxythiazol-2-ylsulfanyl)-benzamide; N-[(2S,3R)-2-methyl-1-azabicyclo[2.2.2]oct-3-yl]-4-(5-trifluoromethylthiazol-2-ylsulfanyl)-benzamide; N-[(2S, 3R)-2-methyl-1-azabicyclo[2.2.2]oct-3-yl]-4-(5-acetylthiazol-2-ylsulfanyl)-benzamide; N-[(2S,3R)-2-methyl-1-azabicyclo[2.2.2]oct-3-yl]-4-(5-acetaminothiazol-2-ylsulfanyl)-benzamide; N-[(2S,3R)-2-methyl-1-azabicyclo[2.2.2]oct-3-yl]-4-(5-cyanothiazol-2-ylsulfanyl)-benzamide; N-[(2S,3R)-2-methyl-1-azabicyclo[2.2.2]oct-3-yl]-4-(5-morpholin-4-yl-thiazol-2-ylsulfanyl)-benzamide; N-[(2S,3R)-2-methyl-1-azabicyclo[2.2.2]oct-3-yl]-4-(thiazol-2-ylsulfanyl)-benzamide; N-[(2S,3R)-2-methyl-1-azabicyclo[2.2.2]oct-3-yl]-4-(4-methylthiazol-2-ylsulfanyl)-benzamide; N-[(2S,3R)-2-methyl-1-azabicyclo[2.2.2]oct-3-yl]-4-(4-chlorothiazol-2-ylsulfanyl)-benzamide; N-[(2S,3R)-2-methyl-1-azabicyclo[2.2.2]oct-3-yl]-4-(4-methoxythiazol-2-ylsulfanyl)-benzamide; N-[(2S,3R)-2-methyl-1-azabicyclo[2.2.2]oct-3-yl]-4-(4-trifluoromethylthiazol-2-ylsulfanyl)-benzamide; N-[(2S,3R)-2-methyl-1-azabicyclo[2.2.2]oct-3-yl]-4-(4-acetylthiazol-2-ylsulfanyl)-benzamide; N-[(2S,3R)-2-methyl-1-azabicyclo[2.2.2]oct-3-yl-4-(4-acetaminothiazol-2-ylsulfanyl)-benzamide; N-[(2S,3R)-2-methyl-1-azabicyclo[2.2.2]oct-3-yl]-4-(4-cyanothiazol-2-ylsulfanyl)-benzamide; N-(2S,3R)-2-methyl-1-azabicyclo[2.2.2]oct-3-yl]-4-(4-morpholin-4-yl-thiazol-2-ylsulfanyl)-benzamide; N-[(2S,3R)-2-methyl-1-azabicyclo[2.2.2]oct-3-yl]-4-(thiazol-5-ylsulfanyl)-benzamide; N-[(2S,3R)-2-methyl-1-azabicyclo[2.2.2]oct-3-yl]-4-(2-methylthiazol-5-ylsulfanyl)-benzamide; N-[(2S,3R)-2-methyl-1-azabicyclo[2.2.2]oct-3-yl]-4-(2-chlorothiazol-5-ylsulfanyl)-benzamide; N-[(2S,3R)-2-methyl-1-azabicyclo[2.2.2]oct-3-yl]-4-(2-methoxythiazol-5-ylsulfanyl)-benzamide; N-[(2S,3R)-2-methyl-1-azabicyclo[2.2.2]oct-3-yl]-4-(2-trifluoromethylthiazol-5-ylsulfanyl)-benzamide; N-[(2S,3R)-2-methyl-1-azabicyclo[2.2.2]oct-3-yl]-4-(2-acetylthiazol-5-ylsulfanyl)-benzamide; N-[(2S,3R)-2-methyl-1-azabicyclo[2.2.2]oct-3-yl]-4-(2-acetaminothiazol-5-ylsulfanyl)-benzamide; N-[(2S,3R)-2-methyl-1-azabicyclo[2.2.2]oct-3-yl]-4-(2-cyanothiazol-5-ylsulfanyl)-benzamide; N-[(2S,3R)-2-methyl-1-azabicyclo[2.2.2]oct-3-yl]-4-(2-morpholin-4-yl-thiazol-5-ylsulfanyl)-benzamide; N-[(2S,3R)-2-methyl-1-azabicyclo[2.2.2]oct-3-yl]-4-([1,3,4]oxadiazol-2-ylsulfanyl)-benzamide; N-[(2S,3R)-2-methyl-1-azabicyclo[2.2.2]oct-3-yl]-4-(5-methyl[1,3,4]oxadiazol-2-ylsulfanyl)-benzamide; N-[(2S,3R)-2-methyl-1-azabicyclo[2.2.2]oct-3-yl]-4-(5-chloro[1,3,4]oxadiazol-2-ylsulfanyl)-benzamide; N-[(2S,3R)-2-methyl-1-azabicyclo[2.2.2]oct-3-yl]-4-(5-methoxy[1,3,4]oxadiazol-2-ylsulfanyl)-benzamide; N-[(2S,3R)-2-methyl-1-azabicyclo[2.2.2]oct-3-yl]-4-(5-trifluoromethyl[1,3,4]oxadiazol-2-ylsulfanyl)-benzamide; N-[(2S,3R)-2-methyl-1-azabicyclo[2.2.2]oct-3-yl]-4-(5-acetyl[1,3,4]oxadiazol-2-ylsulfanyl)-benzamide; N-[(2S,3R)-2-methyl-1-azabicyclo[2.2.2]oct-3-yl]-4-(5-acetamino[1,3,4]oxadiazo-2-ylsulfanyl)-benzamide; N-[(2S,3R)-2-methyl-1-azabicyclo[2.2.2]oct-3-yl]-4-(5-cyano[1,3,4]oxadiazol-2-ylsulfanyl)-benzamide; N-[(2S,3R)-2-methyl-1-azabicyclo[2.2.2]oct-3-yl]-4-(5-morpholin-4-yl-[1,3,4]oxadiazol-2-ylsulfanyl)-benzamide; N-[(2S,3R)-2-methyl-1-azabicyclo[2.2.2]oct-3-yl]-4-([1,3,4]thiadiazol-2-ylsulfanyl)-benzamide; N-[(2S,3R)-2-methyl-1-azabicyclo[2.2.2]oct-3-yl]-4-(5-methyl[1,3,4]thiadiazol-2-ylsulfanyl)-benzamide; N-[(2S,3R)-2-methyl-1-azabicyclo[2.2.2]oct-3-yl]-4-(5-chloro[1,3,4]thiadizole-2-ylsulfanyl)-benzamide; N-[(2S,3R)-2-methyl-1-azabicyclo[2.2.2]oct-3-yl]-4-(5-trifluoromethyl[1,3,4]thiadiazol-2-ylsulfanyl)-benzamide; N-[(2S,3R)-2-methyl-1-azabicyclo[2.2.2]oct-3-yl]-4-(5-acetyl[1,3,4]thiadiazol-2-ylsulfanyl)-benzamide; N-[(2S,3R)-2-methyl-1-azabicyclo[2.2.2]oct-3-yl]-4-(5-acetamino[1,3,4]thiadiazol-2-ylsulfanyl)-benzamide; N-[(2S,3R)-2-methyl-1-azabicyclo[2.2.2]oct-3-yl]-4-(5-cyano[1,3,4]thiadiazol-2-ylsulfanyl)-benzamide; N-[(2S,3R)-2-methyl-1-azabicyclo[2.2.2]oct-3-yl]-4-(5-morpholin-4-yl-[1,3,4]thiadiazol-2-ylsulfanyl)-benzamide; N-[(2S,3R)-2-methyl-1-azabicyclo[2.2.2]oct-3-yl]-4-(pyrrol-2-yloxy)-benzamide; N-[(2S,3R)-2-methyl-1-azabicyclo[2.2.2]oct-3-yl]-4-(5-methylpyrrol-2-yloxy)-benzamide; N-[(2S,3R)-2-methyl-1-azabicyclo[2.2.2]oct-3-yl]-4-(5-chloropyrrol-2-yloxy)-benzamide; N-[(2S,3R)-2-methyl-1-azabicyclo[2.2.2]oct-3-yl]-4-(5-methoxypyrrol-2-yloxy)-benzamide; N-[(2S,3R)-2-methyl-1-azabicyclo[2.2.2]oct-3-yl]-4-(5-trifluoromethylpyrrol-2-yloxy)-benzamide; N-[(2S,3R)-2-methyl-1-azabicyclo[2.2.2]oct-3-yl]-4-(5-acetylpyrrol-2-yloxy)-benzamide; N-[(2S,3R)-2-methyl-1-azabicyclo[2.2.2]oct-3-yl]-4-(5-acetaminopyrrol-2-yloxy)-benzamide; N-[(2S,3R)-2-methyl-1-azabicyclo[2.2.2]oct-3-yl]-4-(5-cyanopyrrol-2-yloxy)-benzamide; N-[(2S,3R)-2-methyl-1-azabicyclo[2.2.2]oct-3-yl]-4-(5-morpholin-4-yl-pyrrol-2-yloxy)-benzamide; N-[(2S,3R)-2-methyl-1-azabicyclo[2.2.2]oct-3-yl]-4-(3H-imidazol-4-yloxy)-benzamide; N-[(2S,3R)-2-methyl-1-azabicyclo[2.2.2]oct-3-yl]-4-(2-methyl-3H-imidazol-4-yloxy)-benzamide; N-[(2S,3R)-2-methyl-1-azabicyclo[2.2.2]oct-3-yl]-4-(2-chloro-3H-imidazol4-yloxy)-benzamide; N-[(2S,3R)-2-methyl-1-azabicyclo[2.2.2]oct-3-yl]-4-(2-methoxy-3H-imidazol-4-yloxy)-benzamide; N-[(2S,3R)-2-methyl-1-azabicyclo[2.2.2]oct-3-yl]-4-(2-trifluoromethyl-3H-imidazol-4-yloxy)-benzamide; N-[(2S,3R)-2-methyl-1-azabicyclo[2.2.2]oct-3-yl]-4-(2-acetyl-3H-imidazol-4-yloxy)-benzamide; N-[(2S,3R)-2-methyl-1-azabicyclo[2.2.2]oct-3-yl]-4-(2-acetamino-3H-imidazol-4-yloxy)-benzamide; N-[(2S,3R)-2-methyl-1-azabicyclo[2.2.2]oct-3-yl]-4-(2-cyano-3H-imidazol-4-yloxy)-benzamide; N-[(2S,3R)-2-methyl-1-azabicyclo[2.2.2]oct-3-yl]-4-(2-morpholin-4-yl-3H-imidazol-4-yloxy)-benzamide; N-[(2S,3R)-2-methyl-1-azabicyclo[2.2.2]oct-3-yl]-4-(isoxazol-2-yloxy)-benzamide; N-[(2S,3R)-2-methyl-1-azabicyclo[2.2.2]oct-3-yl]-4-(5-methylisoxazol-3-yloxy)-benzamide; N-[(2S,3R)-2-methyl-1-azabicyclo[2.2.2]oct-3-yl]-4-(5-chloroisoxazol-3-yloxy)-benzamide; N-[(2S,3R)-2-methyl-1-azabicyclo[2.2.2]oct-3-yl]-4-(5-methoxyisoxazol-3-yloxy)-benzamide; N-[(2S,3R)-2-methyl-1-azabicyclo[2.2.2]oct-3-yl]-4-(5-trifluoromethylisoxazol-3-yloxy)-benzamide; N-[(2S,3R)-2-methyl-1-azabicyclo[2.2.2]oct-3-yl]-4-(5-acetylisoxazol-3-yloxy)-benzamide; N-[(2S,3R)-2-methyl-1-azabicyclo[2.2.2]oct-3-yl]-4-(5-acetaminoisoxazol-3-yloxy)-benzamide; N-[(2S,3R)-2-methyl-1-azabicyclo[2.2.2]oct-3-yl]-4-(5-cyanoisoxazol-3-yloxy)-benzamide; N-[(2S,3R)-2-methyl-1-azabicyclo[2.2.2]oct-3-yl]-4-(5-morpholin-4-yl-isoxazol-3-yloxy)-benzamide; N-[(2S,3R)-2-methyl-1-azabicyclo[2.2.2]oct-3-yl]-4-(isothiazol-2-yloxy)-benzamide; N-[(2S,3R)-2-methyl-1-azabicyclo[2.2.2]oct-3-yl]-4-(5-methylisothiazol-3-yloxy)-benzamide; N-[(2S,3R)-2-methyl-1-azabicyclo[2.2.2]oct-3-yl]-4-(5-chloroisothiazol-3-yloxy)-benzamide; N-[(2S,3R)-2-methyl-1-azabicyclo[2.2.2]oct-3-yl]-4-(5-methoxyisothiazol-3-yloxy)-benzamide; N-[(2S,3R)-2- methyl-1-azabicyclo[2.2.2]oct-3-yl]-4-(5-trifluoromethylisothiazol-3-yloxy)-benzamide; N-[(2S,3R)-2-methyl-1-azabicyclo[2.2.2]oct-3-yl]-4-(5-acetylisothiazol-3-yloxy)-benzamide; N-[(2S,3R)-2-methyl-1-azabicyclo[2.2.2]oct-3-yl]-4-(5-acetaminoisothiazol-3-yloxy)-benzamide; N-[(2S,3R)-2-methyl-1-azabicyclo[2.2.2]oct-3-yl]-4-(5-cyanoisothiazol-3-yloxy)-benzamide; N-[(2S,3R)-2-methyl-1-azabicyclo[2.2.2]oct-3-yl]-4-(5-morpholin-4-yl-isothiazol-3-yloxy)-benzamide; N-[(2S,3R)-2-methyl-1-azabicyclo[2.2.2]oct-3-yl]-4-(pyrrol-2-ylsulfanyl)-benzamide; N-[(2S,3R)-2-methyl-1-azabicyclo[2.2.2]oct-3-yl]-4-(5-methylpyrrol-2-ylsulfanyl)-benzamide; N-[(2S,3R)-2-methyl-1-azabicyclo[2.2.2]oct-3-yl]-4-(5-chloropyrrol-2-ylsulfanyl)-benzamide; N-[(2S,3R)-2-methyl-1-azabicyclo[2.2.2]oct-3-yl]-4-(5-methoxypyrrol-2-ylsulfanyl)-benzamide; N-[(2S,3R)-2-methyl-1-azabicyclo[2.2.2]oct-3-yl]-4-(5-trifluoromethylpyrrol-2-ylsulfanyl)-benzamide; N-[(2S,3R)-2-methyl-1-azabicyclo[2.2.2]oct-3-yl]-4-(5-acetylpyrrol-2-ylsulfanyl)-benzamide; N-[(2S,3R)-2-methyl-1-azabicyclo[2.2.2]oct-3-yl]-4-(5-acetaminopyrrol-2-ylsulfanyl)-benzamide; N-[(2S,3R)-2-methyl-1-azabicyclo[2.2.2]oct-3-yl]-4-(5-cyanopyrrol-2-ylsulfanyl)-benzamide; N-[(2S,3R)-2-methyl-1-azabicyclo[2.2.2]oct-3-yl]-4-(5-morpholin-4-yl-pyrrol-2-ylsulfanyl)-benzamide; N-[(2S,3R)-2-methyl-1-azabicyclo[2.2.2]oct-3-yl]-4-(3H-imidazol-4-ylsulfanyl)-benzamide; N-[(2S,3R)-2-methyl-1-azabicyclo[2.2.2]oct-3-yl]-4-(2-methyl-3H-imidazol-4-ylsulfanyl)-benzamide; N-[(2S,3R)-2-methyl-1-azabicyclo[2.2.2]oct-3-yl]-4-(2-chloro-3H-imidazol-4-ylsulfanyl)-benzamide; N-[(2S,3R)-2-methyl-1-azabicyclo[2.2.2]oct-3-yl]-4-(2-methoxy-3H-imidazol-4-ylsulfanyl)-benzamide; N-[(2S,3R)-2-methyl-1-azabicyclo[2.2.2]oct-3-yl]-4-(2-trifluoromethyl-3H-imidazol-4-ylsulfanyl)-benzamide; N-[(2S,3R)-2-methyl-1-azabicyclo[2.2.2]oct-3-yl]-4-(2-acetyl-3H-imidazol-4-ylsulfanyl)-benzamide; N-[(2S,3R)-2-methyl-1-azabicyclo[2.2.2]oct-3-yl]-4-(2-acetamino-3H-imidazol-4-ylsulfanyl)-benzamide; N-[(2S,3R)-2-methyl-1-azabicyclo[2.2.2]oct-3-yl]-4-(2-cyano-3H-imidazol-4-ylsulfanyl)-benzamide; N-[(2S,3R)-2-methyl-1-azabicyclo[2.2.2]oct-3-yl]-4-(2-morpholin-4-yl-3H-imidazol-4-ylsulfanyl)-benzamide; N-[(2S,3R)-2-methyl-1-azabicyclo[2.2.2]oct-3-yl]-4-(isoxazol-2-ylsulfanyl)-benzamide; N-[(2S,3R)-2-methyl-1-azabicyclo[2.2.2]oct-3-yl]-4-(5-methylisoxazol-3-ylsulfanyl)-benzamide; N-[(2S,3R)-2-methyl-1-azabicyclo[2.2.2]oct-3-yl]-4-(5-chloroisoxazol-3-ylsulfanyl)-benzamide; N-[(2S,3R)-2-methyl-1-azabicyclo[2.2.2]oct-3-yl]-4-(5-methoxyisoxazol-3-ylsulfanyl)-benzamide; N-[(2S,3R)-2-methyl-1-azabicyclo[2.2.2]oct-3-yl]-4-(5-trifluoromethylisoxazol-3-ylsulfanyl)-benzamide; N-[(2S,3R)-2-methyl-1-azabicyclo[2.2.2]oct-3-yl]-4-(5-acetylisoxazol-3-ylsulfanyl)-benzamide; N-[(2S,3R)-2-methyl-1-azabicyclo[2.2.2]oct-3-yl]-4-(5-acetaminoisoxazol-3-ylsulfanyl)-benzamide; N-[(2S,3R)-2-methyl-1-azabicyclo[2.2.2]oct-3-yl]-4-(5-cyanoisoxazol-3-ylsulfanyl)-benzamide; N-[(2S,3R)-2-methyl-1-azabicyclo[2.2.2]oct-3-yl]-4-(5-morpholin-4-yl-isoxazol-3-ylsulfanyl)-benzamide; N-[(2S,3R)-2-methyl-1-azabicyclo[2.2.2]oct-3-yl]-4-(isothiazol-2-ylsulfanyl)-benzamide; N-[(2S,3R)-2-methyl-1-azabicyclo[2.2.2]oct-3-yl]-4-(5-methylisothiazol-3-ylsulfanyl)-benzamide; N-[(2S,3R)-2-methyl-1-azabicyclo[2.2.2]oct-3-yl]-4-(5-chloroisothiazol-3-ylsulfanyl)-benzamide; N-[(2S,3R)-2-methyl-1-azabicyclo[2.2.2]oct-3-yl]-4-(5-methoxyisothiazol-3-ylsulfanyl)-benzamide; N-[(2S,3R)-2-methyl-1-azabicyclo[2.2.2]oct-3-yl]-4-(5-trifluoromethylisothiazol-3-ylsulfanyl)-benzamide; N-[(2S,3R)-2-methyl-1-azabicyclo[2.2.2]oct-3-yl]-4-(5-acetylisothiazol-3-ylsulfanyl)-benzamide; N-[(2S,3R)-2-methyl-1-azabicyclo[2.2.2]oct-3-yl]-4-(5-acetaminoisothiazol-3-ylsulfanyl)-benzamide; N-[(2S,3R)-2-methyl-1-azabicyclo[2.2.2]oct-3-yl]-4-(5-cyanoisothiazol-3-ylsulfanyl)-benzamide; N-[(2S,3R)-2-methyl-1-azabicyclo[2.2.2]oct-3-yl]-4-(5-morpholin-4-yl-isothiazol-3-ylsulfanyl)-benzamide; N-[(2S,3R)-2-methyl-1-azabicyclo[2.2.2]oct-3-yl]-4-(6-methylpyridin-3-yloxy)-benzamide; N-[(2S,3R)-2-methyl-1-azabicyclo[2.2.2]oct-3-yl]-4-(6-chloropyridin-3-yloxy)-benzamide; N-[(2S,3R)-2-methyl-1-azabicyclo[2.2.2]oct-3-yl]-4-(6-methoxypyridin-3-yloxy)-benzamide; N-[(2S,3R)-2-methyl-1-azabicyclo[2.2.2]oct-3-yl]-4-(6-trifluoromethylpyridin-3-yloxy)-benzamide; N-[(2S,3R)-2-methyl-1-azabicyclo[2.2.2]oct-3-yl]-4-(6-acetylpyridin-3-yloxy)-benzamide; N-[(2S,3R)-2-methyl-1-azabicyclo[2.2.2]oct-3-yl]-4-(6-acetaminopyridin-3-yloxy)-benzamide; N-[(2S,3R)-2-methyl-1-azabicyclo[2.2.2]oct-3-yl]-4-(6-cyanopyridin-3-yloxy)-benzamide; N-[(2S,3R)-2-methyl-1-azabicyclo[2.2.2]oct-3-yl]-4-(6-morpholin-4-yl-pyridin-3-yloxy)-benzamide; N-[(2S,3R)-2-methyl-1-azabicyclo[2.2.2]oct-3-yl]-4-(2-methylpyridin-4-yloxy)-benzamide; N-[(2S,3R)-2-methyl-1-azabicyclo[2.2.2]oct-3-yl]-4-(2-chloropyridin-4-yloxy)-benzamide; N-[(2S,3R)-2-methyl-1-azabicyclo[2.2.2]oct-3-yl]-4-(2-methoxypyridin-4-yloxy)-benzamide; N-[(2S,3R)-2-methyl-1-azabicyclo[2.2.2]oct-3-yl]-4-(2-trifluoromethylpyridin-4-yloxy)-benzamide; N-[(2S,3R)-2-methyl-1-azabicyclo[2.2.2]oct-3-yl]-4-(2-acetylpyridin-4-yloxy)-benzamide; N-[(2S,3R)-2-methyl-1-azabicyclo[2.2.2]oct-3-yl]-4-(2-acetaminopyridin-4-yloxy)-benzamide; N-[(2S,3R)-2-methyl-1-azabicyclo[2.2.2]oct-3-yl]-4-(2-cyanopyridin-4-yloxy)-benzamide; N-[(2S,3R)-2-methyl-1-azabicyclo[2.2.2]oct-3-yl]-4-(2-morpholin-4-yl-pyridin-4-yloxy)-benzamide; N-[(2S,3R)-2-methyl-1-azabicyclo[2.2.2]oct-3-yl]-4-(5-methylpyridin-2-yloxy)-benzamide; N-[(2S,3R)-2-methyl-1-azabicyclo[2.2.2]oct-3-yl]-4-(5-chloropyridin-2-yloxy)-benzamide; N-[(2S,3R)-2-methyl-1-azabicyclo[2.2.2]oct-3-yl]-4-(5-methoxypyridin-2-yloxy)-benzamide; N-[(2S,3R)-2-methyl-1-azabicyclo[2.2.2]oct-3-yl]-4-(5-trifluoromethylpyridin-2-yloxy)-benzamide; N-[(2S,3R)-2-methyl-1-azabicyclo[2.2.2]oct-3-yl]-4-(5-acetylpyridin-2-yloxy)-benzamide; N-[(2S,3R)-2-methyl-1-azabicyclo[2.2.2]oct-3-yl]-4-(5-acetaminopyridin-2-yloxy)-benzamide; N-[(2S,3R)-2-methyl-1-azabicyclo[2.2.2]oct-3-yl]-4-(5-cyanopyridin-2-yloxy)-benzamide; N-[(2S,3R)-2-methyl-1-azabicyclo[2.2.2]oct-3-yl]-4-(5-morpholin-4-yl-pyridin-2-yloxy)-benzamide; N-[(2S,3R)-2-methyl-1-azabicyclo[2.2.2]oct-3-yl]-4-(4-methylpyridin-2-yloxy)-benzamide; N-[(2S,3R)-2-methyl-1-azabicyclo[2.2.2]oct-3-yl]-4-(4-chloropyridin-2-yloxy)-benzamide; N-[(2S,3R)-2-methyl-1-azabicyclo[2.2.2]oct-3-yl]-4-(4-methoxypyridin-2-yloxy)-benzamide; N-[(2S,3R)-2-methyl-1-azabicyclo[2.2.2]oct-3-yl]-4-(4-trifluoromethylpyridin-2-yloxy)-benzamide; N-[(2S,3R)-2-methyl-1-azabicyclo[2.2.2]oct-3-yl]-4-(4-acetylpyridin-2-yloxy)-benzamide; N-[(2S,3R)-2-methyl-1-azabicyclo[2.2.2]oct-3-yl]-4-(4-acetaminopyridin-2-yloxy)-benzamide; N-[(2S,3R)-2-methyl-1-azabicyclo[2.2.2]oct-3-yl]-4-(4-cyanopyridin-2-yloxy)-benzamide; N-[(2S,3R)-2-methyl-1-azabicyclo[2.2.2]oct-3-yl]-4-(4- morpholin-4-yl-pyridin-2-yloxy)-benzamide; N-[(2S,3R)-2-methyl-1-azabicyclo[2.2.2]oct-3-yl]-4-(6-methylpyridin-2-yloxy)-benzamide; N-[(2S,3R)-2-methyl-1-azabicyclo[2.2.2]oct-3-yl]-4-(6-chloropyridin-2-yloxy)-benzamide; N-[(2S,3R)-2-methyl-1-azabicyclo[2.2.2]oct-3-yl]-4-(6-methoxypyridin-2-yloxy)-benzamide; N-[(2S,3R)-2-methyl-1-azabicyclo[2.2.2]oct-3-yl]-4-(6-trifluoromethylpyridin-2-yloxy)-benzamide; N-[(2S,3R)-2-methyl-1-azabicyclo[2.2.2]oct-3-yl]-4-(6-acetylpyridin-2-yloxy)-benzamide; N-[(2S,3R)-2-methyl-1-azabicyclo[2.2.2]oct-3-yl]-4-(6-acetaminopyridin-2-yloxy)-benzamide; N-[(2S,3R)-2-methyl-1-azabicyclo[2.2.2]oct-3-yl]-4-(6-cyanopyridin-2-yloxy)-benzamide; N-[(2S,3R)-2-methyl-1-azabicyclo[2.2.2]oct-3-yl]-4-(6-morpholin-4-pyridin-2-yloxy)-benzamide; N-[(2S,3R)-2-methyl-1-azabicyclo[2.2.2]oct-3-yl]-4-(5-methylpyridin-3-yloxy)-benzamide; N-[(2S,3R)-2-methyl-1-azabicyclo[2.2.2]oct-3-yl]-4-(5-chloropyridin-3-yloxy)-benzamide; N-[(2S,3R)-2-methyl-1-azabicyclo[2.2.2]oct-3-yl]-4-(5-methoxypyridin-3-yloxy)-benzamide; N-[(2S,3R)-2-methyl-1-azabicyclo[2.2.2]oct-3-yl]-4-(5-trifluoromethylpyridin-3-yloxy)-benzamide; N-[(2S,3R)-2-methyl-1-azabicyclo[2.2.2]oct-3-yl]-4-(5-acetylpyridin-3-yloxy)-benzamide; N-[(2S,3R)-2-methyl-1-azabicyclo[2.2.2]oct-3-yl]-4-(5-acetaminopyridin-3-yloxy)-benzamide; N-[(2S,3R)-2-methyl-1-azabicyclo[2.2.2]oct-3-yl]-4-(5-cyanopyridin-3-yloxy)-benzamide; N-[(2S,3R)-2-methyl-1-azabicyclo[2.2.2]oct-3-yl]-4-(5-morpholin-4-yl-pyridin-3-yloxy)-benzamide; N-[(2S,3R)-2-methyl-1-azabicyclo[2.2.2]oct-3-yl]-4-(2-chloropyridin-3-yloxy)-benzamide; N-[(2S,3R)-2-methyl-1-azabicyclo[2.2.2]oct-3-yl]-4-(4-chloropyridin-3-yloxy)-benzamide; N-[(2S,3R)-2-methyl-1-azabicyclo[2.2.2]oct-3-yl]-4-(3-chloropyridin-4-yloxy)-benzamide; N-[(2S,3R)-2-methyl-1-azabicyclo[2.2.2]oct-3-yl]-4-(3-chloropyridin-2-yloxy)-benzamide; N-[(2S,3R)-2-methyl-1-azabicyclo[2.2.2]oct-3-yl]-4-(6-methylpyridin-3-ylsulfanyl)-benzamide; N-[(2S,3R)-2-methyl-1-azabicyclo[2.2.2]oct-3-yl]-4-(6-chloropyridin-3-ylsulfanyl)-benzamide; N-[(2S,3R)-2-methyl-1-azabicyclo[2.2.2]oct-3-yl]-4-(6-methoxypyridin-3-ylsulfanyl)-benzamide; N-[(2S,3R)-2-methyl-1-azabicyclo[2.2.2]oct-3-yl]-4-(6-trifluoromethylpyridin-3-ylsulfanyl)-benzamide; N-[(2S,3R)-2-methyl-1-azabicyclo[2.2.2]oct-3-yl]-4-(6-acetylpyridin-3-ylsulfanyl)-benzamide; N-[(2S,3R)-2-methyl-1-azabicyclo[2.2.2]oct-3-yl]-4-(6-acetaminopyridin-3-ylsulfanyl)-benzamide; N-[(2S,3R)-2-methyl-1-azabicyclo[2.2.2]oct-3-yl]-4-(6-cyanopyridin-3-ylsulfanyl)-benzamide; N-[(2S,3R)-2-methyl-1-azabicyclo[2.2.2]oct-3-yl]-4-(6-morpholin-4-yl-pyridin-3-ylsulfanyl)-benzamide; N-[(2S,3R)-2-methyl-1-azabicyclo[2.2.2]oct-3-yl]-4-(2-methylpyridin-4-ylsulfanyl)-benzamide; N-[(2S,3R)-2-methyl-1-azabicyclo[2.2.2]oct-3-yl]-4-(2-chloropyridin-4-ylsulfanyl)-benzamide; N-[(2S,3R)-2-methyl-1-azabicyclo[2.2.2]oct-3-yl]-4-(2-methoxypyridin-4-ylsulfanyl)-benzamide; N-[(2S,3R)-2-methyl-1-azabicyclo[2.2.2]oct-3-yl]-4-(2-trifluoromethylpyridin-4-ylsulfanyl)-benzamide; N-[(2S,3R)-2-methyl-1-azabicyclo[2.2.2]oct-3-yl]-4-(2-acetylpyridin-4-ylsulfanyl)-benzamide; N-[(2S,3R)-2-methyl-1-azabicyclo[2.2.2]oct-3-yl]-4-(2-acetaminopyridin-4-ylsulfanyl)-benzamide; N-[(2S,3R)-2-methyl-1-azabicyclo[2.2.2]oct-3-yl]-4-(2-cyanopyridin-4-ylsulfanyl)-benzamide; N-[(2S,3R)-2-methyl-1-azabicyclo[2.2.2]oct-3-yl]-4-(2-morpholin-4-yl-pyridin-4-ylsulfanyl)-benzamide; N-[(2S,3R)-2-methyl-1-azabicyclo[2.2.2]oct-3-yl]-4-(5-methylpyridin-2-ylsulfanyl)-benzamide; N-[(2S,3R)-2-methyl-1-azabicyclo[2.2.2]oct-3-yl]-4-(5-chloropyridin-2-ylsulfanyl)-benzamide; N-[(2S,3R)-2-methyl-1-azabicyclo[2.2.2]oct-3-yl]-4-(5-methoxypyridin-2-ylsulfanyl)-benzamide; N-[(2S,3R)-2-methyl-1-azabicyclo[2.2.2]oct-3-yl]-4-(5-trifluoromethylpyridin-2-ylsulfanyl)-benzamide; N-[(2S,3R)-2-methyl-1-azabicyclo[2.2.2]oct-3-yl]-4-(5-acetylpyridin-2-ylsulfanyl)-benzamide; N-[(2S,3R)-2-methyl-1-azabicyclo[2.2.2]oct-3-yl]-4-(5-acetaminopyridin-2-ylsulfanyl)-benzamide; N-[(2S,3R)-2-methyl-1-azabicyclo[2.2.2]oct-3-yl]-4-(5-cyanopyridin-2-ylsulfanyl)-benzamide; N-[(2S,3R)-2-methyl-1-azabicyclo[2.2.2]oct-3-yl]-4-(5-morpholin-4-yl-pyridin-2-ylsulfanyl)-benzamide; N-[(2S,3R)-2-methyl-1-azabicyclo[2.2.2]oct-3-yl]-4-(4-methylpyridin-2-ylsulfanyl)-benzamide; N-[(2S,3R)-2-methyl-1-azabicyclo[2.2.2]oct-3-yl]-4-(4-chloropyridin-2-ylsulfanyl)-benzamide; N-[(2S,3R)-2-methyl-1-azabicyclo[2.2.2]oct-3-yl]-4-(4-methoxypyridin-2-ylsulfanyl)-benzamide; N-[(2S,3R)-2-methyl-1-azabicyclo[2.2.2]oct-3-yl]-4-(4-trifluoromethylpyridin-2-ylsulfanyl)-benzamide; N-[(2S,3R)-2-methyl-1-azabicyclo[2.2.2]oct-3-yl]-4-(4-acetylpyridin-2-ylsulfanyl)-benzamide; N-[(2S,3R)-2-methyl-1-azabicyclo[2.2.2]oct-3-yl]-4-(4-acetaminopyridin-2-ylsulfanyl)-benzamide; N-[(2S,3R)-2-methyl-1-azabicyclo[2.2.2]oct-3-yl]-4-(4-cyanopyridin-2-ylsulfanyl)-benzamide; N-[(2S,3R)-2-methyl-1-azabicyclo[2.2.2]oct-3-yl]-4-(4-morpholin-4-yl-pyridin-2-ylsulfanyl)-benzamide; N-[(2S,3R)-2-methyl-1-azabicyclo[2.2.2]oct-3-yl]-4-(6-methylpyridin-2-ylsulfanyl)-benzamide; N-[(2S,3R)-2-methyl-1-azabicyclo[2.2.2]oct-3-yl]-4-(6-chloropyridin-2-ylsulfanyl)-benzamide; N-[(2S,3R)-2-methyl-1-azabicyclo[2.2.2]oct-3-yl]-4-(6-methoxypyridin-2-ylsulfanyl)-benzamide; N-[(2S,3R)-2-methyl-1-azabicyclo[2.2.2]oct-3-yl]-4-(6-trifluoromethylpyridin-2-ylsulfanyl)-benzamide; N-[(2S,3R)-2-methyl-1-azabicyclo[2.2.2]oct-3-yl]-4-(6-acetylpyridin-2-ylsulfanyl)-benzamide; N-[(2S,3R)-2-methyl-1-azabicyclo[2.2.2]oct-3-yl]-4-(6-acetaminopyridin-2-ylsulfanyl)-benzamide; N-[(2S,3R)-2-methyl-1-azabicyclo[2.2.2]oct-3-yl]-4-(6-cyanopyridin-2-ylsulfanyl)-benzamide; N-[(2S,3R)-2-methyl-1-azabicyclo[2.2.2]oct-3-yl]-4-(6-morpholin-4-yl-pyridin-2-ylsulfanyl)-benzamide; N-[(2S,3R)-2-methyl-1-azabicyclo[2.2.2]oct-3-yl]-4-(5-methylpyridin-3-ylsulfanyl)-benzamide; N-[(2S,3R)-2-methyl-1-azabicyclo[2.2.2]oct-3-yl]-4-(5-chloropyridin-3-ylsulfanyl)-benzamide; N-[(2S,3R)-2-methyl-1-azabicyclo[2.2.2]oct-3-yl]-4-(5-methoxypyridin-3-ylsulfanyl)-benzamide; N-[(2S,3R)-2-methyl-1-azabicyclo[2.2.2]oct-3-yl]-4-(5-trifluoromethylpyridin-3-ylsulfanyl)-benzamide; N-[(2S,3R)-2-methyl-1-azabicyclo[2.2.2]oct-3-yl]-4-(5-acetylpyridin-3-ylsulfanyl)-benzamide; N-[(2S,3R)-2-methyl-1-azabicyclo[2.2.2]oct-3-yl]-4-(5-acetaminopyridin-3-ylsulfanyl)-benzamide; N-[(2S,3R)-2-methyl-1-azabicyclo[2.2.2]oct-3-yl]-4(5-cyanopyridin-3-ylsulfanyl)-benzamide; N-[(2S,3R)-2-methyl-1-azabicyclo[2.2.2]oct-3-yl]-4-(5-morpholin-4-yl-pyridin-3-ylsulfanyl)-benzamide; N-[(2S,3R)-2-methyl-1-azabicyclo[2.2.2]oct-3-yl]-4-(2-chloropyridin-3-ylsulfanyl)-benzamide; N-[(2S,3R)-2-methyl-1- azabicyclo[2.2.2]oct-3-yl]-4-(4-chloropyridin-3-ylsulfanyl)-benzamide; N-[(2S,3R)-2-methyl-1-azabicyclo[2.2.2]oct-3-yl]-4-(3-chloropyridin-4-ylsulfanyl)-benzamide; N-[(2S,3R)-2-methyl-1-azabicyclo[2.2.2]oct-3-yl]-4-(3-chloropyridin-2-ylsulfanyl)-benzamide; or pharmaceutically acceptable salts thereof.

29. A method for treating a disease or condition in a mammal, wherein the α7 nicotinic acetylcholine receptor is implicated comprising administering to a mammal a therapeutically effective amount of compound(s) according to claim 1.

30. The method according to claim 29, wherein the disease or condition is schizophrenia, or psychosis.

31. The method according to claim 30, wherein said compound(s) is(are) administered rectally, topically, orally, sublingually, or parenterally.

32. The method according to claim 30, wherein said compound(s) is(are) administered from about 0.001 to about 100 mg/kg of body weight of said mammal per day.

33. The method according to claim 30, wherein said compound(s) is(are) administered from about 0.1 to about 50 mg/kg of body weight of said mammal per day.

34. A method for treating a disease or condition in a mammal, wherein the α7 nicotinic acetylcholine receptor is implicated comprising administering to a mammal a therapeutically effective amount of compound(s) according to claim 5.

35. The method according to claim 34, wherein the disease or condition is schizophrenia, or psychosis.

36. The method according to claim 35, wherein said compound(s) is(are) administered rectally, topically, orally, sublingually, or parenterally.

37. The method according to claim 35, wherein said compound(s) is(are) administered from about 0.001 to about 100 mg/kg of body weight of said mammal per day.

38. The method according to claim 35, wherein said compound(s) is(are) administered from about 0.1 to about 50 mg/kg of body weight of said mammal per day.

39. A method for treating a disease or condition in a mammal, wherein the α7 nicotinic acetylcholine receptor is implicated comprising administering to a mammal a therapeutically effective amount of compound(s) according to claim 11.

40. The method according to claim 39, wherein the disease or condition is schizophrenia, or psychosis.

41. The method according to claim 40, wherein said compound(s) is(are) administered rectally, topically, orally, sublingually, or parenterally.

42. The method according to claim 40, wherein said compound(s) is(are) administered from about 0.001 to about 100 mg/kg of body weight of said mammal per day.

43. The method according to claim 40, wherein said compound(s) is(are) administered from about 0.1 to about 50 mg/kg of body weight of said mammal per day.

44. A method for treating a disease or condition in a mammal, wherein the α7 nicotinic acetylcholine receptor is implicated comprising administering to a mammal a therapeutically effective amount of compound(s) according to claim 12.

45. The method according to claim 44, wherein the disease or condition is schizophrenia, or psychosis.

46. The method according to claim 45, wherein said compound(s) is(are) administered rectally, topically, orally, sublingually, or parenterally.

47. The method according to claim 45, wherein said compound(s) is(are) administered from about 0.001 to about 100 mg/kg of body weight of said mammal per day.

48. The method according to claim 45, wherein said compound(s) is(are) administered from about 0.1 to about 50 mg/kg of body weight of said mammal per day.

49. A method for treating a disease or condition in a mammal, wherein the α7 nicotinic acetylcholine receptor is implicated comprising administering to a mammal a therapeutically effective amount of compound(s) according to claim 13.

50. The method according to claim 49, wherein the disease or condition is schizophrenia, or psychosis.

51. The method according to claim 50, wherein said compound(s) is(are) administered rectally, topically, orally, sublingually, or parenterally.

52. The method according to claim 50, wherein said compound(s) is(are) administered from about 0.001 to about 100 mg/kg of body weight of said mammal per day.

53. The method according to claim 50, wherein said compound(s) is(are) administered from about 0.1 to about 50 mg/kg of body weight of said mammal per day.

54. A method for treating a disease or condition in a mammal, wherein the α7 nicotinic acetylcholine receptor is implicated comprising administering to a mammal a therapeutically effective amount of compound(s) according to claim 14.

55. The method according to claim 54, wherein the disease or condition is schizophrenia, or psychosis.

56. The method according to claim 55, wherein said compound(s) is(are) administered rectally, topically, orally, sublingually, or parenterally.

57. The method according to claim 55, wherein said compound(s) is(are) administered from about 0.001 to about 100 mg/kg of body weight of said mammal per day.

58. The method according to claim 55, wherein said compound(s) is(are) administered from about 0.1 to about 50 mg/kg of body weight of said mammal per day.

59. A method for treating a disease or condition in a mammal, wherein the α7 nicotinic acetylcholine receptor is implicated comprising administering to a mammal a therapeutically effective amount of compound(s) according to claim 15.

60. The method according to claim 59, wherein the disease or condition is schizophrenia, or psychosis.

61. The method according to claim 60, wherein said compound(s) is(are) administered rectally, topically, orally, sublingually, or parenterally.

62. The method according to claim 60, wherein said compound(s) is(are) administered from about 0.001 to about 100 mg/kg of body weight of said mammal per day.

63. The method according to claim 60, wherein said compound(s) is(are) administered from about 0.1 to about 50 mg/kg of body weight of said mammal per day.

64. A method for treating a disease or condition in a mammal, wherein the α7 nicotinic acetylcholine receptor is implicated comprising administering to a mammal a therapeutically effective amount of compound(s) according to claim 21.

65. The method according to claim 64, wherein the disease or condition is schizophrenia, or psychosis.

66. The method according to claim 65, wherein said compound(s) is(are) administered rectally, topically, orally, sublingually, or parenterally.

67. The method according to claim 65, wherein said compound(s) is(are) administered from about 0.001 to about 100 mg/kg of body weight of said mammal per day.

68. The method according to claim 65, wherein said compound(s) is(are) administered from about 0.1 to about 50 mg/kg of body weight of said mammal per day.

69. A method for treating a disease or condition in a mammal, wherein the α7 nicotinic acetylcholine receptor is implicated comprising administering to a mammal a therapeutically effective amount of compound(s) according to claim 22.

70. The method according to claim 69, wherein the disease or condition is schizophrenia, or psychosis.

71. The method according to claim 70, wherein said compound(s) is(are) administered rectally, topically, orally, sublingually, or parenterally.

72. The method according to claim 70, wherein said compound(s) is(are) administered from about 0.001 to about 100 mg/kg of body weight of said mammal per day.

73. The method according to claim 70, wherein said compound(s) is(are) administered from about 0.1 to about 50 mg/kg of body weight of said mammal per day.

74. A method for treating a disease or condition in a mammal, wherein the α7 nicotinic acetylcholine receptor is implicated comprising administering to a mammal a therapeutically effective amount of compound(s) according to claim 23.

75. The method according to claim 74, wherein the disease or condition is schizophrenia, or psychosis.

76. The method according to claim 75, wherein said compound(s) is(are) administered rectally, topically, orally, sublingually, or parenterally.

77. The method according to claim 75, wherein said compound(s) is(are) administered from about 0.001 to about 100 mg/kg of body weight of said mammal per day.

78. The method according to claim 75, wherein said compound(s) is(are) administered from about 0.1 to about 50 mg/kg of body weight of said mammal per day.

79. A method for treating a disease or condition in a mammal, wherein the α7 nicotinic acetylcholine receptor is implicated comprising administering to a mammal a therapeutically effective amount of compound(s) according to claim 24.

80. The method according to claim 79, wherein the disease or condition is schizophrenia, or psychosis.

81. The method according to claim 80, wherein said compound(s) is(are) administered rectally, topically, orally, sublingually, or parenterally.

82. The method according to claim 80, wherein said compound(s) is(are) administered from about 0.001 to about 100 mg/kg of body weight of said mammal per day.

83. The method according to claim 80, wherein said compound(s) is(are) administered from about 0.1 to about 50 mg/kg of body weight of said mammal per day.

84. A method for treating a disease or condition in a mammal, wherein the α7 nicotinic acetylcholine receptor is implicated comprising administering to a mammal a therapeutically effective amount of compound(s) according to claim 25.

85. The method according to claim 84, wherein the disease or condition is schizophrenia, or psychosis.

86. The method according to claim 85, wherein said compound(s) is(are) administered rectally, topically, orally, sublingually, or parenterally.

87. The method according to claim 85, wherein said compound(s) is(are) administered from about 0.001 to about 100 mg/kg of body weight of said mammal per day.

88. The method according to claim 85, wherein said compound(s) is(are) administered from about 0.1 to about 50 mg/kg of body weight of said mammal per day.

89. A method for treating a disease or condition in a mammal, wherein the α7 nicotinic acetylcholine receptor is implicated comprising administering to a mammal a therapeutically effective amount of compound(s) according to claim 26.

90. The method according to claim 89, wherein the disease or condition is schizophrenia, or psychosis.

91. The method according to claim 90, wherein said compound(s) is(are) administered rectally, topically, orally, sublingually, or parenterally.

92. The method according to claim 90, wherein said compound(s) is(are) administered from about 0.001 to about 100 mg/kg of body weight of said mammal per day.

93. The method according to claim 90, wherein said compound(s) is(are) administered from about 0.1 to about 50 mg/kg of body weight of said mammal per day.

94. A method for treating a disease or condition in a mammal, wherein the α7 nicotinic acetylcholine receptor is implicated comprising administering to a mammal a therapeutically effective amount of compound(s) according to claim 27.

95. The method according to claim 94, wherein the disease or condition is schizophrenia, or psychosis.

96. The method according to claim 95, wherein said compound(s) is(are) administered rectally, topically, orally, sublingually, or parenterally.

97. The method according to claim 95, wherein said compound(s) is(are) administered from about 0.001 to about 100 mg/kg of body weight of said mammal per day.

98. The method according to claim 95, wherein said compound(s) is(are) administered from about 0.1 to about 50 mg/kg of body weight of said mammal per day.

99. A method for treating a disease or condition in a mammal, wherein the α7 nicotinic acetylcholine receptor is implicated comprising administering to a mammal a therapeutically effective amount of compound(s) according to claim 28.

100. The method according to claim 99, wherein the disease or condition is schizophrenia, or psychosis.

101. The method according to claim 100, wherein said compound(s) is(are) administered rectally, topically, orally, sublingually, or parenterally.

102. The method according to claim 100, wherein said compound(s) is(are) administered from about 0.001 to about 100 mg/kg of body weight of said mammal per day.

103. The method according to claim 100, wherein said compound(s) is(are) administered from about 0.1 to about 50 mg/kg of body weight of said mammal per day.

104. A pharmaceutical composition comprising compound(s) according to claim 1, or a pharmaceutically acceptable salt thereof, and a pharmaceutically acceptable carrier.

105. A pharmaceutical composition comprising compound(s) according to claim 5, or a pharmaceutically acceptable salt thereof, and a pharmaceutically acceptable carrier.

106. A pharmaceutical composition comprising compound(s) according to claim 11, or a pharmaceutically acceptable salt thereof, and a pharmaceutically acceptable carrier.

107. A pharmaceutical composition comprising compound(s) according to claim 12, or a pharmaceutically acceptable salt thereof, and a pharmaceutically acceptable carrier.

108. A pharmaceutical composition comprising compound(s) according to claim 13, or a pharmaceutically acceptable salt thereof, and a pharmaceutically acceptable carrier.

109. A pharmaceutical composition comprising compound(s) according to claim 14, or a pharmaceutically acceptable salt thereof, and a pharmaceutically acceptable carrier.

110. A pharmaceutical composition comprising compound(s) according to claim 15, or a pharmaceutically acceptable salt thereof, and a pharmaceutically acceptable carrier.

111. A pharmaceutical composition comprising compound(s) according to claim 21, or a pharmaceutically acceptable salt thereof, and a pharmaceutically acceptable carrier.

112. A pharmaceutical composition comprising compound(s) according to claim 22, or a pharmaceutically acceptable salt thereof, and a pharmaceutically acceptable carrier.

113. A pharmaceutical composition comprising compound(s) according to claim 23, or a pharmaceutically acceptable salt thereof, and a pharmaceutically acceptable carrier.

114. A pharmaceutical composition comprising compound(s) according to claim 24, or a pharmaceutically acceptable salt thereof, and a pharmaceutically acceptable carrier.

115. A pharmaceutical composition comprising compound(s) according to claim 25, or a pharmaceutically acceptable salt thereof, and a pharmaceutically acceptable carrier.

116. A pharmaceutical composition comprising compound(s) according to claim 26, or a pharmaceutically acceptable salt thereof, and a pharmaceutically acceptable carrier.

117. A pharmaceutical composition comprising compound(s) according to claim 27, or a pharmaceutically acceptable salt thereof, and a pharmaceutically acceptable carrier.

118. A pharmaceutical composition comprising compound(s) according to claim 28, or a pharmaceutically acceptable salt thereof, and a pharmaceutically acceptable carrier.

* * * * *